(12) United States Patent
Atkins et al.

(10) Patent No.: US 11,241,044 B2
(45) Date of Patent: Feb. 8, 2022

(54) AIRFLOW MANAGEMENT FOR VAPORIZER DEVICE

(71) Applicant: JUUL Labs, Inc., San Francisco, CA (US)

(72) Inventors: Ariel Atkins, San Francisco, CA (US); Adam Bowen, San Mateo, CA (US); Steven Christensen, Burlingame, CA (US); Nicholas J. Hatton, Oakland, CA (US); Esteban Leon Duque, Berkeley, CA (US); James Monsees, San Francisco, CA (US); Christopher James Rosser, Cambridge (GB); Andrew J. Stratton, Royston (GB)

(73) Assignee: JUUL Labs, Inc., San Francisco, CA (US)

( * ) Notice: Subject to any disclaimer, the term of this patent is extended or adjusted under 35 U.S.C. 154(b) by 0 days.

(21) Appl. No.: 16/520,149

(22) Filed: Jul. 23, 2019

(65) Prior Publication Data

US 2020/0022417 A1    Jan. 23, 2020

Related U.S. Application Data

(60) Provisional application No. 62/702,320, filed on Jul. 23, 2018.

(51) Int. Cl.
| | | |
|---|---|---|
| A24F 40/485 | (2020.01) |
| F15D 1/02 | (2006.01) |
| G01L 13/00 | (2006.01) |
| G05D 16/04 | (2006.01) |
| A24F 40/10 | (2020.01) |
| A24F 40/42 | (2020.01) |
| A24B 15/167 | (2020.01) |

(52) U.S. Cl.
CPC ............ *A24F 40/485* (2020.01); *A24F 40/10* (2020.01); *A24F 40/42* (2020.01); *F15D 1/02* (2013.01); *G01L 13/00* (2013.01); *G05D 16/04* (2013.01); *A24B 15/167* (2016.11)

(58) Field of Classification Search
CPC ........ A24F 47/08; A24F 40/50; A24F 40/485; A24F 40/40; A24F 40/53; A24F 47/008
See application file for complete search history.

(56) References Cited

U.S. PATENT DOCUMENTS

| | | |
|---|---|---|
| 4,947,874 A | 8/1990 | Brooks et al. |
| 4,947,875 A | 8/1990 | Brooks et al. |
| 5,381,509 A | 1/1995 | Mills |

(Continued)

FOREIGN PATENT DOCUMENTS

| | | |
|---|---|---|
| AT | 507187 A4 | 3/2010 |
| CA | 2768122 C | 11/2014 |

(Continued)

*Primary Examiner* — Michael J Felton
*Assistant Examiner* — Katherine A Will
(74) *Attorney, Agent, or Firm* — Mintz Levin Cohn Ferris Glovsky and Popeo, P.C.

(57) ABSTRACT

A vaporization device includes a cartridge having a reservoir that holds a vaporizable material, a heating element, and a wicking element that can draw the vaporizable material to the heating element to be vaporized. The wicking element can include two ends in contact with the reservoir. The cartridge can include an airflow control feature for controlling airflow in the cartridge.

17 Claims, 13 Drawing Sheets

(56) References Cited

U.S. PATENT DOCUMENTS

| | | |
|---|---|---|
| 5,646,666 A | 7/1997 | Cowger et al. |
| 6,155,268 A | 12/2000 | Takeuchi |
| 6,322,268 B1 | 11/2001 | Kaufmann et al. |
| 6,516,796 B1 | 2/2003 | Cox et al. |
| 6,606,998 B1 | 8/2003 | Gold |
| 7,793,861 B2 | 9/2010 | Bankers et al. |
| 7,802,569 B2 | 9/2010 | Yeates et al. |
| 8,365,742 B2 | 2/2013 | Hon |
| 8,485,180 B2 | 7/2013 | Smutney et al. |
| 8,528,569 B1 | 9/2013 | Newton |
| 8,733,345 B2 | 5/2014 | Siller |
| 8,833,364 B2 | 9/2014 | Buchberger |
| 8,881,737 B2 | 11/2014 | Collett et al. |
| 9,220,302 B2 | 12/2015 | DePiano et al. |
| 9,277,770 B2 | 3/2016 | DePiano et al. |
| 9,308,336 B2 | 4/2016 | Newton |
| 9,510,623 B2 | 12/2016 | Tucker et al. |
| 9,549,573 B2 | 1/2017 | Monsees et al. |
| 9,609,893 B2 | 4/2017 | Novak, III et al. |
| 9,623,205 B2 | 4/2017 | Buchberger |
| 9,648,908 B1 | 5/2017 | Rinehart et al. |
| 9,681,688 B1 | 6/2017 | Rinehart et al. |
| 9,806,549 B2 | 10/2017 | Liberti et al. |
| 9,814,265 B2 | 11/2017 | Rinker et al. |
| 9,839,238 B2 | 12/2017 | Worm et al. |
| 9,913,493 B2 | 3/2018 | Worm et al. |
| 9,918,496 B2 | 3/2018 | Kane et al. |
| 9,936,733 B2 | 4/2018 | Ampolini et al. |
| 9,955,726 B2 | 5/2018 | Brinkley et al. |
| 9,999,250 B2 | 6/2018 | Minskoff et al. |
| 10,004,259 B2 | 6/2018 | Sebastian et al. |
| 10,034,988 B2 | 7/2018 | Wensley et al. |
| 10,039,323 B2 | 8/2018 | Schuler et al. |
| 10,045,562 B2 | 8/2018 | Buchberger |
| 10,045,568 B2 | 8/2018 | Monsees et al. |
| 10,058,129 B2 | 8/2018 | Monsees et al. |
| 10,085,481 B2 | 10/2018 | Verleur et al. |
| 10,085,485 B2 | 10/2018 | Hunt et al. |
| 10,104,915 B2 | 10/2018 | Bowen et al. |
| 10,130,123 B2 | 11/2018 | Hatton et al. |
| 10,131,532 B2 | 11/2018 | Murison et al. |
| 10,159,282 B2 | 12/2018 | Monsees et al. |
| 10,188,148 B2 | 1/2019 | Althorpe et al. |
| 10,194,693 B2 | 2/2019 | Wensley et al. |
| 10,206,429 B2 | 2/2019 | Davis et al. |
| 10,278,427 B2 | 5/2019 | Buchberger |
| 10,285,444 B2 | 5/2019 | Clemens et al. |
| 10,292,435 B2 | 5/2019 | Qiu |
| 10,314,340 B2 | 6/2019 | Davis et al. |
| 10,383,367 B2 | 8/2019 | Rasmussen et al. |
| 10,383,368 B2 | 8/2019 | Larson |
| 10,405,579 B2 | 9/2019 | Collett et al. |
| 10,412,996 B2 | 9/2019 | Bright et al. |
| 10,631,576 B1 | 4/2020 | Chen et al. |
| 2001/0032643 A1 | 10/2001 | Hochrainer et al. |
| 2002/0142291 A1 | 10/2002 | Bauer et al. |
| 2003/0215335 A1 | 11/2003 | Crivelli |
| 2004/0089314 A1* | 5/2004 | Felter ............... A24F 47/008 131/194 |
| 2005/0067503 A1 | 3/2005 | Katase |
| 2006/0093977 A1 | 5/2006 | Pellizzari et al. |
| 2007/0079889 A1 | 4/2007 | Lindsay et al. |
| 2008/0029095 A1 | 2/2008 | Esser |
| 2009/0255534 A1 | 10/2009 | Paterno |
| 2009/0324206 A1 | 12/2009 | Young et al. |
| 2011/0094523 A1* | 4/2011 | Thorens ............... H05B 1/0202 131/194 |
| 2011/0226236 A1 | 9/2011 | Buchberger |
| 2012/0111346 A1 | 5/2012 | Rinker et al. |
| 2013/0042865 A1 | 2/2013 | Monsees et al. |
| 2013/0213418 A1 | 8/2013 | Tucker et al. |
| 2013/0327327 A1 | 12/2013 | Edwards et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0144429 A1 | 5/2014 | Wensley et al. |
| 2014/0190496 A1 | 7/2014 | Wensley et al. |
| 2014/0253144 A1 | 9/2014 | Novak, III et al. |
| 2014/0261486 A1 | 9/2014 | Potter et al. |
| 2014/0261487 A1 | 9/2014 | Chapman et al. |
| 2014/0261488 A1 | 9/2014 | Tucker |
| 2014/0261491 A1 | 9/2014 | Hawes |
| 2014/0261492 A1 | 9/2014 | Kane et al. |
| 2014/0270729 A1 | 9/2014 | DePiano et al. |
| 2014/0283855 A1 | 9/2014 | Hawes et al. |
| 2015/0020823 A1 | 1/2015 | Lipowicz et al. |
| 2015/0020825 A1 | 1/2015 | Galloway et al. |
| 2015/0027456 A1 | 1/2015 | Janardhan et al. |
| 2015/0027473 A1 | 1/2015 | Graf |
| 2015/0047662 A1 | 2/2015 | Hopps |
| 2015/0128969 A1 | 5/2015 | Chapman et al. |
| 2015/0136158 A1 | 5/2015 | Stevens et al. |
| 2015/0144145 A1 | 5/2015 | Chang et al. |
| 2015/0201674 A1 | 7/2015 | Dooly et al. |
| 2015/0208731 A1 | 7/2015 | Malamud et al. |
| 2015/0216233 A1 | 8/2015 | Sears et al. |
| 2015/0216237 A1 | 8/2015 | Wensley et al. |
| 2015/0223522 A1 | 8/2015 | Ampolini et al. |
| 2015/0224268 A1 | 8/2015 | Henry et al. |
| 2015/0245659 A1 | 9/2015 | DePiano et al. |
| 2015/0245669 A1 | 9/2015 | Cadieux et al. |
| 2015/0257445 A1 | 9/2015 | Henry, Jr. et al. |
| 2015/0257447 A1 | 9/2015 | Sullivan |
| 2015/0258289 A1 | 9/2015 | Henry, Jr. et al. |
| 2015/0282527 A1 | 10/2015 | Henry, Jr. |
| 2015/0313275 A1 | 11/2015 | Anderson et al. |
| 2015/0313282 A1 | 11/2015 | Ademe et al. |
| 2015/0320116 A1 | 11/2015 | Bleloch et al. |
| 2015/0327596 A1 | 11/2015 | Alarcon et al. |
| 2015/0335070 A1 | 11/2015 | Sears et al. |
| 2016/0007653 A1 | 1/2016 | Tu |
| 2016/0018347 A1 | 1/2016 | Drbal et al. |
| 2016/0021931 A1 | 1/2016 | Hawes et al. |
| 2016/0029697 A1 | 2/2016 | Shafer |
| 2016/0058071 A1 | 3/2016 | Hearn |
| 2016/0109115 A1 | 4/2016 | Lipowicz |
| 2016/0143361 A1 | 5/2016 | Juster et al. |
| 2016/0150828 A1 | 6/2016 | Goldstein et al. |
| 2016/0206000 A1 | 7/2016 | Lord et al. |
| 2016/0213065 A1* | 7/2016 | Wensley ............... H05B 3/46 |
| 2016/0219933 A1 | 8/2016 | Henry, Jr. et al. |
| 2016/0255876 A1* | 9/2016 | Rostami ............... A24F 47/008 |
| 2016/0261021 A1 | 9/2016 | Marion et al. |
| 2016/0262453 A1 | 9/2016 | Ampolini et al. |
| 2016/0262454 A1 | 9/2016 | Sears et al. |
| 2016/0286865 A1 | 10/2016 | King et al. |
| 2016/0309783 A1 | 10/2016 | Hopps et al. |
| 2016/0325858 A1 | 11/2016 | Ampolini et al. |
| 2016/0331030 A1 | 11/2016 | Ampolini et al. |
| 2016/0331033 A1 | 11/2016 | Hopps et al. |
| 2016/0331034 A1 | 11/2016 | Cameron |
| 2016/0331035 A1 | 11/2016 | Cameron |
| 2016/0338408 A1 | 11/2016 | Guenther, Jr. et al. |
| 2016/0345632 A1 | 12/2016 | Lipowicz |
| 2016/0366947 A1 | 12/2016 | Monsees et al. |
| 2016/0374399 A1 | 12/2016 | Monsees et al. |
| 2017/0013880 A1 | 1/2017 | O'Brien et al. |
| 2017/0020191 A1 | 1/2017 | Lamb et al. |
| 2017/0023952 A1 | 1/2017 | Henry, Jr. et al. |
| 2017/0027227 A1 | 2/2017 | Lipowicz |
| 2017/0035115 A1 | 2/2017 | Monsees et al. |
| 2017/0042245 A1 | 2/2017 | Buchberger et al. |
| 2017/0043910 A1 | 2/2017 | Hopps et al. |
| 2017/0045150 A1* | 2/2017 | Marsh ............... H02J 7/00 |
| 2017/0045994 A1 | 2/2017 | Murison et al. |
| 2017/0079322 A1 | 3/2017 | Li et al. |
| 2017/0095005 A1 | 4/2017 | Monsees et al. |
| 2017/0099877 A1 | 4/2017 | Worm et al. |
| 2017/0105455 A1 | 4/2017 | Qiu |
| 2017/0112194 A1 | 4/2017 | Sur et al. |
| 2017/0112196 A1 | 4/2017 | Sur et al. |
| 2017/0119052 A1 | 5/2017 | Williams et al. |
| 2017/0119053 A1 | 5/2017 | Henry, Jr. et al. |
| 2017/0127722 A1 | 5/2017 | Davis et al. |

(56) References Cited

U.S. PATENT DOCUMENTS

| | | |
|---|---|---|
| 2017/0135399 A1 | 5/2017 | Gavrielov et al. |
| 2017/0143038 A1 | 5/2017 | Dickens |
| 2017/0156398 A1 | 6/2017 | Sur et al. |
| 2017/0181223 A1 | 6/2017 | Sur et al. |
| 2017/0181471 A1 | 6/2017 | Phillips et al. |
| 2017/0188626 A1 | 7/2017 | Davis et al. |
| 2017/0188627 A1 | 7/2017 | Sur |
| 2017/0188629 A1 | 7/2017 | Dickens et al. |
| 2017/0202266 A1 | 7/2017 | Sur |
| 2017/0208863 A1 | 7/2017 | Davis et al. |
| 2017/0238617 A1 | 8/2017 | Scatterday |
| 2017/0251718 A1 | 9/2017 | Armoush et al. |
| 2017/0251721 A1 | 9/2017 | Rostami et al. |
| 2017/0251723 A1 | 9/2017 | Kobal et al. |
| 2017/0251724 A1 | 9/2017 | Lamb et al. |
| 2017/0258143 A1 | 9/2017 | Lederer |
| 2017/0273355 A1 | 9/2017 | Rogers et al. |
| 2017/0273360 A1 | 9/2017 | Brinkley et al. |
| 2017/0280767 A1 | 10/2017 | Li et al. |
| 2017/0290371 A1 | 10/2017 | Davis et al. |
| 2017/0294804 A1 | 10/2017 | Sur |
| 2017/0333650 A1 | 11/2017 | Buchberger et al. |
| 2017/0360093 A1 | 12/2017 | Fernando |
| 2017/0367402 A1 | 12/2017 | Lau et al. |
| 2017/0367407 A1 | 12/2017 | Althorpe et al. |
| 2018/0020728 A1 | 1/2018 | Alarcon et al. |
| 2018/0042305 A1* | 2/2018 | Hogwood ............ A24F 47/008 |
| 2018/0077967 A1 | 3/2018 | Hatton et al. |
| 2018/0160733 A1 | 6/2018 | Leadley et al. |
| 2018/0177240 A1 | 6/2018 | Duque et al. |
| 2018/0184722 A1 | 7/2018 | Murison et al. |
| 2018/0199627 A1 | 7/2018 | Bowen et al. |
| 2018/0220707 A1* | 8/2018 | Biel .................. A61M 15/06 |
| 2018/0296777 A1* | 10/2018 | Terry .................. A61M 11/042 |
| 2019/0001077 A1 | 1/2019 | Xu et al. |
| 2019/0124982 A1 | 5/2019 | Atkins et al. |
| 2019/0200674 A1 | 7/2019 | Tucker et al. |
| 2019/0261688 A1* | 8/2019 | Qiu .................... H05B 1/0227 |
| 2019/0373953 A1 | 12/2019 | Atkins et al. |
| 2019/0387797 A1 | 12/2019 | Christensen et al. |
| 2020/0000143 A1 | 1/2020 | Anderson et al. |
| 2020/0022417 A1 | 1/2020 | Atkins et al. |
| 2020/0077707 A1 | 3/2020 | Alston et al. |
| 2020/0107585 A1 | 4/2020 | Atkins et al. |
| 2020/0114094 A1 | 4/2020 | Atkins et al. |
| 2020/0128874 A1 | 4/2020 | Atkins et al. |

FOREIGN PATENT DOCUMENTS

| | | |
|---|---|---|
| CA | 2883143 C | 7/2017 |
| CA | 2935072 C | 5/2018 |
| CA | 2949516 C | 6/2019 |
| CN | 1491525 A | 4/2004 |
| CN | 100589726 C | 2/2010 |
| CN | 102326869 A | 1/2012 |
| CN | 103237469 A | 8/2013 |
| CN | 105476069 A | 4/2016 |
| CN | 105963833 A | 9/2016 |
| CN | 207011686 U | 2/2018 |
| CN | 108158039 A | 6/2018 |
| CN | 109259313 A | 1/2019 |
| CN | 105919164 B | 3/2019 |
| DE | 102017123869 B4 | 5/2019 |
| EP | 0358114 A2 | 3/1990 |
| EP | 2967154 A1 | 1/2016 |
| EP | 3097803 A1 | 11/2016 |
| EP | 3143882 A2 | 3/2017 |
| EP | 3143884 A3 | 4/2017 |
| EP | 3165102 A3 | 8/2017 |
| EP | 3232834 B1 | 4/2019 |
| JP | 2012506263 A | 3/2012 |
| JP | 2015-504653 A | 2/2015 |
| JP | 2015-198985 A | 11/2015 |
| JP | 2018-509158 A | 4/2018 |
| JP | 2018-523976 A | 8/2018 |
| KR | 2009/0010954 A | 1/2009 |
| KR | 101430282 B1 | 8/2014 |
| KR | 20150046318 A | 4/2015 |
| KR | 20180083424 A | 7/2018 |
| KR | 101957819 B1 | 3/2019 |
| KR | 20190057399 A | 5/2019 |
| WO | WO-9501137 A1 | 1/1995 |
| WO | WO-2008077271 A1 | 7/2008 |
| WO | WO-2012026963 A2 | 3/2012 |
| WO | WO-2012059726 A2 | 5/2012 |
| WO | WO-2014/071329 A1 | 5/2014 |
| WO | WO-2016019353 A1 | 2/2016 |
| WO | WO-2016028544 A1 | 2/2016 |
| WO | WO-2016041209 A1 | 3/2016 |
| WO | WO-2016058139 A1 | 4/2016 |
| WO | WO-2016/079155 A1 | 5/2016 |
| WO | WO-2016079151 A1 | 5/2016 |
| WO | WO-2016127468 A1 | 8/2016 |
| WO | WO-2016128562 A1 | 8/2016 |
| WO | WO-2016145072 A1 | 9/2016 |
| WO | WO-2016193336 A1 | 12/2016 |
| WO | WO-2017011419 A1 | 1/2017 |
| WO | WO-2017016323 A1 | 2/2017 |
| WO | WO-2017036819 A1 | 3/2017 |
| WO | WO-2017036828 A1 | 3/2017 |
| WO | WO-2017036879 A1 | 3/2017 |
| WO | WO-2017046363 A1 | 3/2017 |
| WO | WO-2017064051 A1 | 4/2017 |
| WO | WO-2017064324 A1 | 4/2017 |
| WO | WO-2017072277 A1 | 5/2017 |
| WO | WO-2017082728 A1 | 5/2017 |
| WO | WO-2017085240 A1 | 5/2017 |
| WO | WO-2017093535 A1 | 6/2017 |
| WO | WO-2017108268 A1 | 6/2017 |
| WO | WO-2017122196 A1 | 7/2017 |
| WO | WO-2017137554 A1 | 8/2017 |
| WO | WO-2017153270 A1 | 9/2017 |
| WO | WO-2017163052 A1 | 9/2017 |
| WO | WO-2017207416 A1 | 12/2017 |
| WO | WO-2017207419 A1 | 12/2017 |
| WO | WO-2018057957 A1 | 3/2018 |
| WO | WO-2018087738 A1 | 5/2018 |
| WO | WO-2018138688 A1 | 8/2018 |
| WO | WO-2019173923 A1 | 9/2019 |
| WO | WO-2019232086 A1 | 12/2019 |

* cited by examiner

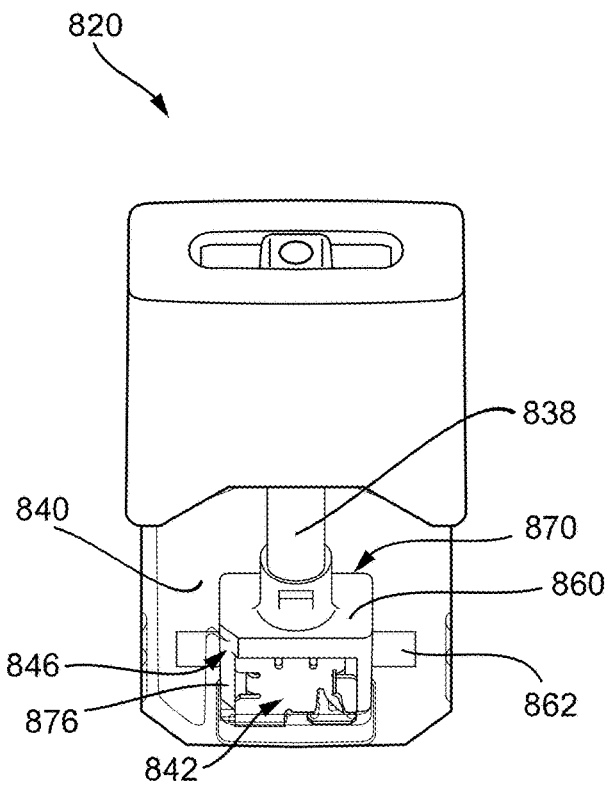
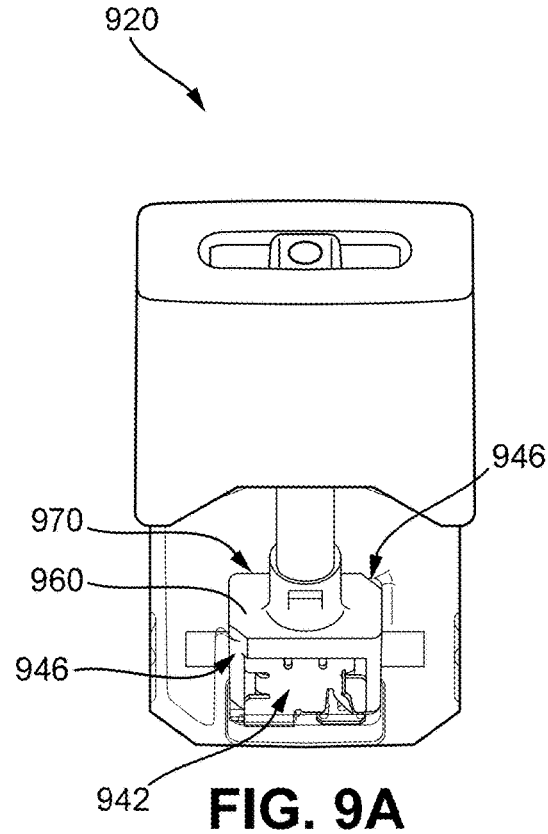
FIG. 8A
FIG. 9A
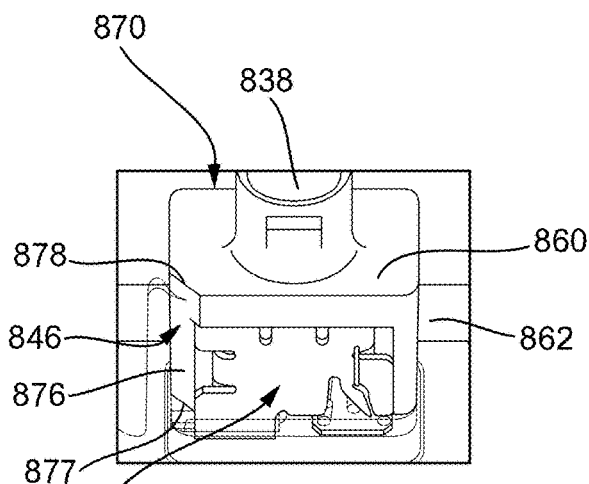
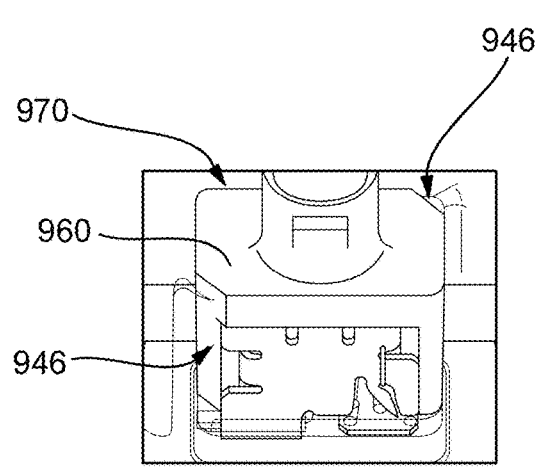
FIG. 8B
FIG. 9B

AIRFLOW MANAGEMENT FOR VAPORIZER DEVICE

CROSS REFERENCE

The present application claims priority to U.S. Provisional Patent Application No. 62/702,320 entitled "Airflow Management for Vaporizer Device" filed Jul. 23, 2018, which is hereby incorporated by reference in its entirety.

TECHNICAL FIELD

The subject matter described herein relates to vaporizer devices, including portable vaporizer devices for generating an inhalable aerosol from one or more vaporizable materials.

BACKGROUND

Vaporizer devices, which can also be referred to as vaporizers, electronic vaporizer devices or e-vaporizer devices, can be used for delivery of an aerosol (or "vapor") containing one or more active ingredients by inhalation of the aerosol by a user of the vaporizing device. For example, electronic nicotine delivery systems (ENDS) include a class of vaporizer devices that are battery powered and that may be used to simulate the experience of smoking, but without burning of tobacco or other substances.

In use of a vaporizer device, the user inhales an aerosol, commonly called vapor, which may be generated by a heating element that vaporizes (e.g., causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a separable part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

A typical approach by which a vaporizer device generates an inhalable aerosol from a vaporizable material involves heating the vaporizable material in a vaporization chamber (or a heater chamber) to cause the vaporizable material to be converted to the gas (or vapor) phase. A vaporization chamber generally refers to an area or volume in the vaporizer device within which a heat source (e.g., conductive, convective, and/or radiative) causes heating of a vaporizable material to produce a mixture of air and vaporized vaporizable to form a vapor for inhalation by a user of the vaporization device.

In some vaporizer device embodiments, the vaporizable material can be drawn out of a reservoir or reservoir chamber and into the vaporization chamber via a wicking element (a wick). Such drawing of the vaporizable material into the vaporization chamber can be due, at least in part, to capillary action provided by the wick, which pulls the vaporizable material along the wick in the direction of the vaporization chamber. However, as vaporizable material is drawn out of the reservoir, the pressure inside the reservoir is reduced, thereby creating a vacuum and acting against the capillary action. This can reduce the effectiveness of the wick to draw the vaporizable material into the vaporization chamber, thereby reducing the effectiveness of the vaporization device to vaporize a desired amount of vaporizable material, such as when a user takes a puff on the vaporizer device. Furthermore, the vacuum created in the reservoir can ultimately result in the inability to draw all of the vaporizable material into the vaporization chamber, thereby wasting vaporizable material. As such, improved vaporization devices and/or vaporization cartridges that improve upon or overcome these issues is desired.

The term vaporizer device, as used herein consistent with the current subject matter, generally refers to portable, self-contained, devices that are convenient for personal use. Typically, such devices are controlled by one or more switches, buttons, touch sensitive devices, or other user input functionality or the like (which can be referred to generally as controls) on the vaporizer, although a number of devices that may wirelessly communicate with an external controller (e.g., a smartphone, a smart watch, other wearable electronic devices, etc.) have recently become available. Control, in this context, refers generally to an ability to influence one or more of a variety of operating parameters, which may include without limitation any of causing the heater to be turned on and/or off, adjusting a minimum and/or maximum temperature to which the heater is heated during operation, various games or other interactive features that a user might access on a device, and/or other operations.

SUMMARY

In certain aspects of the current subject matter, challenges associated with the presence of liquid vaporizable materials in or near certain susceptible components of an electronic vaporizer device may be addressed by inclusion of one or more of the features described herein or comparable/equivalent approaches as would be understood by one of ordinary skill in the art. Aspects of the current subject matter relate to methods and system for managing airflow in a vaporizer device.

In one aspect, an embodiment of a cartridge for a vaporizer device is described. The cartridge may include a reservoir chamber defined by a reservoir barrier. The reservoir chamber may be configured to contain a liquid vaporizable material. The cartridge may further include a vaporization chamber in fluid communication with the reservoir chamber and include a wicking element configured to draw the liquid vaporizable material from the reservoir chamber to the vaporization chamber to be vaporized by a heating element. The cartridge may further include an airflow passageway that extends through the vaporization chamber and an airflow control feature for controlling a reservoir pressure in the reservoir chamber.

In some variations, one or more of the following features may optionally be included in any feasible combination. The airflow control feature can include a fluid passageway extending between the reservoir chamber and the airflow passageway. The diameter of the fluid passageway may be sized to allow a surface tension of the liquid vaporizable material to prevent passage of the liquid vaporizable material through the fluid passageway when the reservoir pressure is approximately the same as a second pressure along the airflow passageway. The diameter may be sized to allow the surface tension of the liquid vaporizable material to be disrupted when the reservoir pressure is less than the second pressure along the airflow passageway thereby allowing a volume of air to pass through the airflow control feature and into the reservoir chamber.

In some embodiments, the airflow control feature may include a check valve or a duck bill valve. The airflow control feature may include a coating including a venting material extending over an opening of the fluid passageway. The coating may include a polytetrafluoroethylene (PTFE) material. The airflow control feature may include one or more of a septum, a valve, and a pump. The airflow control feature may include a vent passageway extending along at least one side of a wick housing containing the vaporization chamber, and the vent passageway may extend between the reservoir chamber and the vaporization chamber. The airflow control feature may include a vent passageway extending through a wick housing containing the vaporization chamber, and the vent passageway may extend between the reservoir chamber and the vaporization chamber.

In some embodiments, the cartridge may further include a pressure sensor configured to sense a pressure along the airflow passageway. The cartridge may further include a secondary passageway configured to draw air through a part of the cartridge, and the secondary passageway may be configured to merge with the airflow passageway downstream from the vaporization chamber. The cartridge may further include a pressure-sensing passageway that extends between an outlet of the cartridge and a pressure sensor, and the pressure-sensing passageway may be separate from the airflow passageway.

The cartridge may further include an inlet positioned along a first side of the cartridge and an outlet positioned along a second side of the cartridge. The airflow pathway may extend between the inlet and outlet, and the inlet and outlet may be positioned along the first side and second side, respectively, such that the inlet and outlet are open when the cartridge is inserted in a vaporizer device body in a first position and are closed when the cartridge is inserted in the vaporizer device body in a second position. The wicking element may include a flat configuration including at least one pair of opposing sides that extend parallel to each other.

In another interrelated aspect of the current subject matter, a method includes allowing airflow to pass through a vaporization chamber of a vaporizer device thereby combining the airflow with an aerosol formed in the vaporization chamber. The aerosol may be formed by vaporizing a liquid vaporizable material drawn from a porous wick extending between the vaporization chamber and a reservoir chamber containing the liquid vaporizable material. The method may further include drawing the liquid vaporizable material along the porous wick from the reservoir chamber to the vaporization chamber thereby creating a first pressure in the reservoir chamber that is less than a second pressure in an area outside of the reservoir chamber. In addition, the method may include disrupting a surface tension of the liquid vaporizable material along a vent passageway extending between the reservoir chamber and the area outside of the reservoir chamber thereby allowing a volume of air to pass into the reservoir chamber from the vent passageway. Additionally, the method may include increasing the first pressure in the reservoir chamber such that the first pressure is approximately equal to the second pressure.

In some embodiments, the method may further include preventing, as a result of the first pressure being approximately equal to the second pressure, the passage of fluid along the vent passageway. The preventing may be controlled by the fluid tension of the vaporizable fluid. The vaporizable fluid may include at least one of the liquid vaporizable material and air. The airflow control feature may include a vent passageway extending through a wick housing that contains the vaporization chamber. The airflow control feature may include a fluid passageway extending between the reservoir chamber and an airflow passageway.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 8A shows a top perspective view of another embodiment of a venting vaporization chamber element including a vent passageway that is defined in part by a chamfered corner of a wick housing;

FIG. 8B illustrates a partial view of the cartridge of FIG. 8A showing the wick housing and vent;

FIG. 9A shows a top perspective view of another embodiment of a venting vaporization chamber element including two vent passageways that are each defined in part by a chamfered corner of a wick housing;

FIG. 9B illustrates a partial view of the cartridge of FIG. 9A showing the wick housing and vents;

When practical, similar reference numbers denote similar structures, features, or elements.

DETAILED DESCRIPTION

Figure 1A:
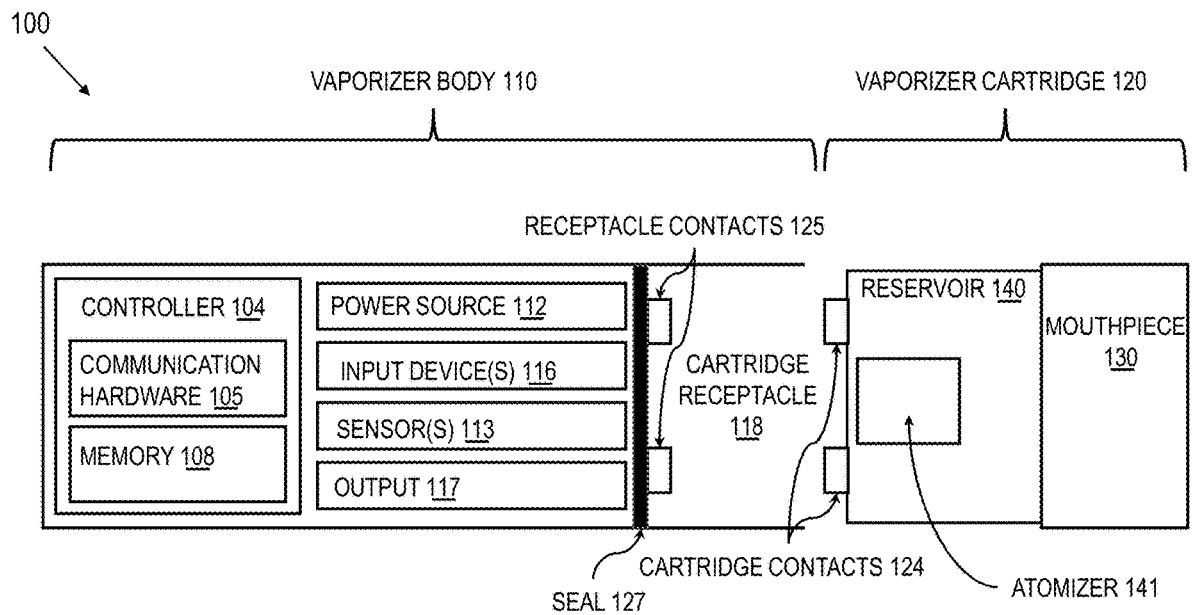
FIG. 1A shows a first embodiment of a vaporizer system including a vaporizer device having a cartridge and a vaporizer device body consistent with implementations of the current subject matter.

Implementations of the current subject matter include devices relating to vaporizing of one or more materials for inhalation by a user. The term "vaporizer" is used generically in the following description to refer to a vaporizer device. Examples of vaporizers consistent with implementations of the current subject matter include electronic vaporizers, or the like. Such vaporizers are generally portable, hand-held devices that heat a vaporizable material to provide an inhalable dose of the material.

The vaporizable material used with a vaporizer may optionally be provided within a cartridge (e.g., a part of the vaporizer that contains the vaporizable material in a reservoir or other container and that can be refillable when empty or disposable in favor of a new cartridge containing additional vaporizable material of a same or different type). A vaporizer may be a cartridge-using vaporizer, a cartridgeless vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material.

In various implementations, a vaporizer may be configured for use with liquid vaporizable material (e.g., a carrier solution in which an active and/or inactive ingredient(s) are suspended or held in solution or a neat liquid form of the vaporizable material itself) or a solid vaporizable material. A solid vaporizable material may include a plant material that emits some part of the plant material as the vaporizable material (e.g., such that some part of the plant material remains as waste after the vaporizable material is emitted for inhalation by a user) or optionally can be a solid form of the vaporizable material itself (e.g., a "wax") such that all of the solid material can eventually be vaporized for inhalation. A liquid vaporizable material can likewise be capable of being completely vaporized or can include some part of the liquid material that remains after all of the material suitable for inhalation has been consumed.

FIGS. 1A-1F illustrate an example vaporizer 100 including a vaporizer body 110 and vaporizer cartridge 120, any of which can include features therein consistent with implementations of the current subject matter. Referring to the block diagram of FIG. 1A, a vaporizer 100 typically includes a power source 112 (such as a battery which may be a rechargeable battery), and a controller 104 (e.g., a processor, circuitry, etc. capable of executing logic) for controlling delivery of heat to an atomizer 141 to cause a vaporizable material to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e. formation of condensed phase particles may be very limited).

Vaporizers for use with liquid vaporizable materials (e.g., neat liquids, suspensions, solutions, mixtures, etc.) typically include an atomizer 141 in which a wicking element (also referred to herein as a wick (not shown in FIG. 1A), which can include any material capable of causing fluid motion by capillary pressure) conveys an amount of a liquid vaporizable material to a part of the atomizer that includes a heating element (also not shown in FIG. 1A). The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described below), and air may, in some implementations of the current subject matter, return to the reservoir through the wick to at least partially equalize pressure in the reservoir. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward from walls of an oven).

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 130 of the vaporizer to cause air to flow from an air inlet, along an airflow path that passes an atomizer (e.g., wicking element and heating element), optionally through one or more condensation areas or chambers, to an air outlet in the mouthpiece. Incoming air passing along the airflow path passes over, through, etc. the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 130 for inhalation by a user).

Activation of the heating element may be caused by automatic detection of the puff based on one or more of signals generated by one or more sensors 113, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, a capacitive lip sensor of the vaporizer; in response to detection of interaction of a user with one or more input devices 116 (e.g., buttons or other tactile control devices of the vaporizer 100), receipt of signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer 100, and can include its own communication hardware, which can establish a wireless communication channel with the communication hardware 105 of the vaporizer 100. For example, a computing device used as part of a vaporizer system may include a general-purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors 113) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 127 to separate an airflow path from other parts of the vaporizer. The seal 127, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 127 may also separate parts of one or more electrical connections between a vaporizer body 110 and a vaporizer cartridge 120. Such arrangements of a seal 127 in a vaporizer 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 127 can also result in a user inhaling air that has passed over parts of the vaporizer device containing or constructed of materials that may not be desirable to be inhaled.

A general class of vaporizers that have recently gained popularity includes a vaporizer body 110 that includes a controller 104, a power source 112 (e.g., battery), one more sensors 113, charging contacts, a seal 127, and a cartridge receptacle 118 configured to receive a vaporizer cartridge 120 for coupling with the vaporizer body through one or more of a variety of attachment structures. In some examples, vaporizer cartridge 120 includes a reservoir 140 for containing a liquid vaporizable material and a mouthpiece 130 for delivering an inhalable dose to a user. The vaporizer cartridge can include an atomizer 141 having a wicking element and a heating element, or alternatively, one or both of the wicking element and the heating element can be part of the vaporizer body. In implementations in which any part of the atomizer 141 (e.g., heating element and/or wicking element) is part of the vaporizer body, the vaporizer can be configured to supply liquid vaporizer material from a reservoir in the vaporizer cartridge to the atomizer part(s) included in the vaporizer body.

Cartridge-based configurations for vaporizers that generate an inhalable dose of a non-liquid vaporizable material via heating of a non-liquid vaporizable material are also within the scope of the current subject matter. For example, a vaporizer cartridge may include a mass of a plant material that is processed and formed to have direct contact with parts of one or more resistive heating elements, and such a vaporizer cartridge may be configured to be coupled mechanically and electrically to a vaporizer body the includes a processor, a power source, and electrical contacts for connecting to corresponding cartridge contacts for completing a circuit with the one or more resistive heating elements.

In vaporizers in which the power source 112 is part of a vaporizer body 110 and a heating element is disposed in a vaporizer cartridge 120 configured to couple with the vaporizer body 110, the vaporizer 100 may include electrical connection features (e.g., means for completing a circuit) for completing a circuit that includes the controller 104 (e.g., a printed circuit board, a microcontroller, or the like), the power source, and the heating element. These features may include at least two contacts on a bottom surface of the vaporizer cartridge 120 (referred to herein as cartridge contacts 124) and at least two contacts disposed near a base of the cartridge receptacle (referred to herein as receptacle contacts 125) of the vaporizer 100 such that the cartridge contacts 124 and the receptacle contacts 125 make electrical connections when the vaporizer cartridge 120 is inserted into and coupled with the cartridge receptacle 118. The circuit completed by these electrical connections can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the at least two cartridge contacts and the at least two receptacle contacts can be configured to electrically connect in either of at least two orientations. In other words, one or more circuits necessary for operation of the vaporizer can be completed by insertion of a vaporizer cartridge 120 in the cartridge receptacle 118 in a first rotational orientation (around an axis along which the end of the vaporizer cartridge having the cartridge is inserted into the cartridge receptacle 118 of the vaporizer body 110) such that a first cartridge contact of the at least two cartridge contacts 124 is electrically connected to a first receptacle contact of the at least two receptacle contacts 125 and a second cartridge contact of the at least two cartridge contacts 124 is electrically connected to a second receptacle contact of the at least two receptacle contacts 125. Furthermore, the one or more circuits necessary for operation of the vaporizer can be completed by insertion of a vaporizer cartridge 120 in the cartridge receptacle 118 in a second rotational orientation such that the first cartridge contact of the at least two cartridge contacts 124 is electrically connected to the second receptacle contact of the at least two receptacle contacts 125 and the second cartridge contact of the at least two cartridge contacts 124 is electrically connected to the first receptacle contact of the at least two receptacle contacts 125. This feature of a vaporizer cartridge 120 being reversible insertable into a cartridge receptacle 118 of the vaporizer body 110 is described further below.

In one example of an attachment structure for coupling a vaporizer cartridge 120 to a vaporizer body, the vaporizer body 110 includes a detent (e.g., a dimple, protrusion, etc.) protruding inwardly from an inner surface the cartridge receptacle 118. One or more exterior surfaces of the vaporizer cartridge 120 can include corresponding recesses (not shown in FIG. 1A) that can fit and/or otherwise snap over such detents when an end of the vaporizer cartridge 120 inserted into the cartridge receptacle 118 on the vaporizer body 110. When the vaporizer cartridge 120 and the vaporizer body 110 are coupled (e.g., by insertion of an end of the vaporizer cartridge 120 into the cartridge receptacle 118 of the vaporizer body 110, the detent into the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118.

Further to the discussion above about the electrical connections between a vaporizer cartridge and a vaporizer body being reversible such that at least two rotational orientations of the vaporizer cartridge in the cartridge receptacle are possible, in some vaporizers the shape of the vaporizer cartridge, or at least a shape of the end of the vaporizer cartridge that is configured for insertion into the cartridge receptacle may have rotational symmetry of at least order two. In other words, the vaporizer cartridge or at least the insertable end of the vaporizer cartridge may be symmetric upon a rotation of 180° around an axis along which the vaporizer cartridge is inserted into the cartridge receptacle. In such a configuration, the circuitry of the vaporizer may support identical operation regardless of which symmetrical orientation of the vaporizer cartridge occurs.

In some examples, the vaporizer cartridge, or at least an end of the vaporizer cartridge configured for insertion in the cartridge receptacle may have a non-circular cross section transverse to the axis along which the vaporizer cartridge is inserted into the cartridge receptacle. For example, the non-circular cross section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross section referred to herein.

The at least two cartridge contacts and the at least two receptacle contacts can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge and the vaporizer body. The electrical contacts may optionally be gold-plated, and/or can include other materials.

Figure 1B:
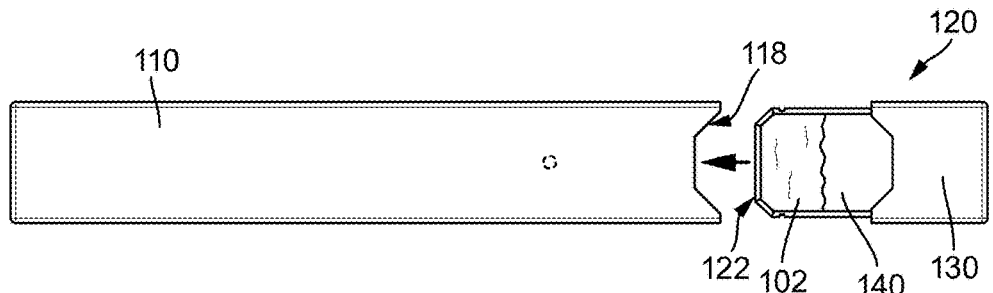
FIG. 1B illustrates a top view of an embodiment of the vaporizer device of FIG. 1A showing a cartridge separated from a vaporizer device body.
Figure 1C:
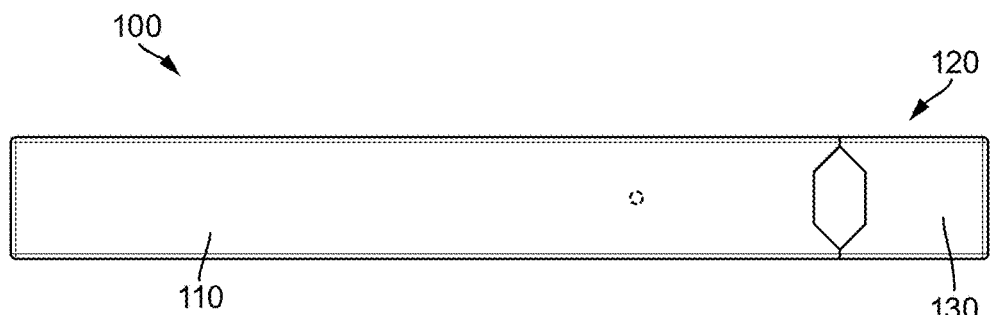
FIG. 1C illustrates a top view of the vaporizer device of FIG. 1B with the cartridge inserted into a cartridge receptacle of the vaporizer device body.
Figure 1D:
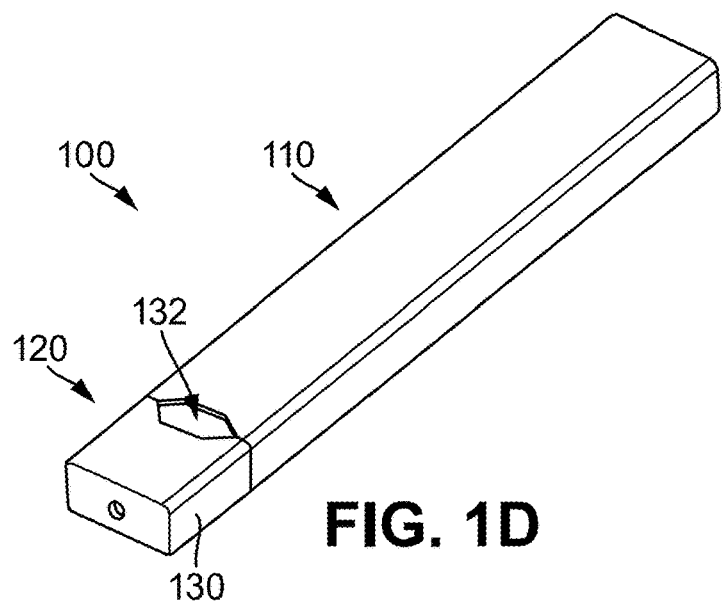
FIG. 1D shows a perspective view of the vaporizer device of FIG. 1B.

FIGS. 1B-1D illustrate an embodiment of the vaporizer body 110 having a cartridge receptacle 118 into which the vaporizer cartridge 120 may be releasably inserted. FIGS. 1B and 1C show top views of the vaporizer 100 illustrating the cartridge being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 may be configured such that the window 132 remains visible when insertably received by a cartridge receptacle 118 of the vaporizer body 110. For example, in one exemplary configuration, the window 132 may be disposed between a bottom edge of the mouthpiece 130 and a top edge of the vaporizer body 110 when the vaporizer cartridge 120 is coupled with the cartridge receptacle 118.

Figure 1E:
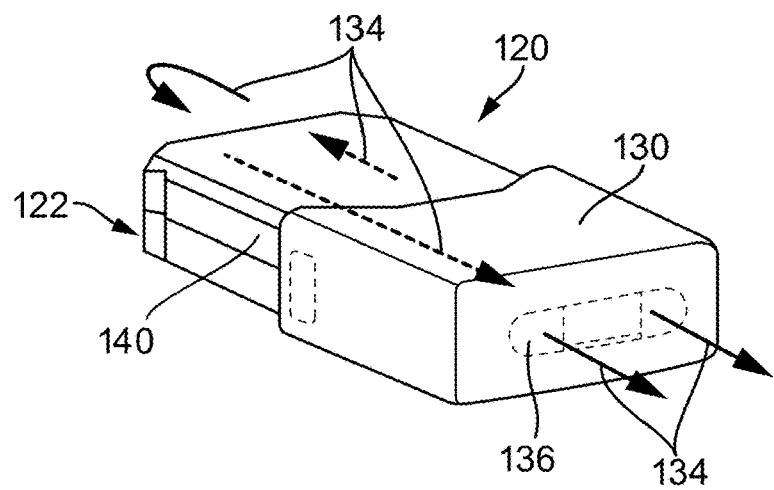
FIG. 1E shows a perspective view of the cartridge of the vaporizer device of FIG. 1B.

FIG. 1E illustrates an example airflow path 134 created during a puff by a user on the vaporizer 100. The airflow path 134 can direct air to a vaporization chamber 150 (see, for example, FIG. 1F) contained in a wick housing where the air is combined with inhalable aerosol for delivery to a user via a mouthpiece 130, which can also be part of the vaporizer cartridge 120. For example, when a user puffs on the vaporizer, the airflow path 134 may pass between an outer surface of the vaporizer cartridge 120 (e.g., the window 132) and an inner surface of a cartridge receptacle 118 on the vaporizer body 110. Air can then be drawn into an insertable end 122 of the cartridge, through the vaporization chamber that includes or contains the heating element and wick, and out through an outlet 136 of the mouthpiece 130 for delivery of the inhalable aerosol to a user.

Figure 1F:
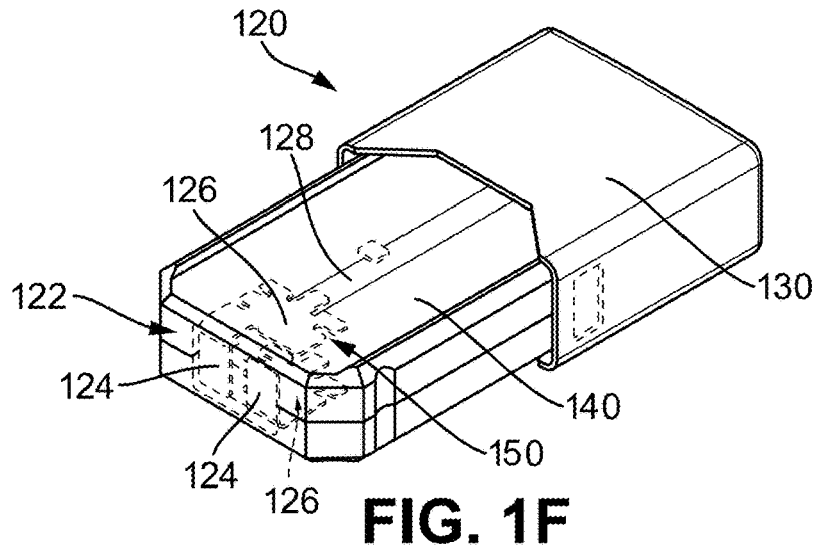
FIG. 1F shows another perspective view of the cartridge of FIG. 1E.

FIG. 1F shows additional features that may be included in a vaporizer cartridge 120 consistent with the current subject matter. For example, the vaporizer cartridge 120 can include a plurality of cartridge contacts (such as cartridge contacts 124) disposed on the insertable end 122, which is configured to be inserted into the cartridge receptacle 118 of a vaporizer body 110. The cartridge contacts 124 can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows a cannula 128 within the vaporizer cartridge 120 that defines part of the airflow path 134 between the heating chamber formed between the conductive structure 126 and the mouthpiece 130.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite an end that includes the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128) and through one or more outlets (such as outlet 136) formed in the mouthpiece 130.

As mentioned above, pulling of vaporizable material from the reservoir can create a vacuum in the reservoir, and such vacuum can reduce or prevent the capillary action provided by the wick. This can reduce the effectiveness of the wick to draw the vaporizable material into the vaporization chamber, thereby reducing the effectiveness of the vaporization device to vaporize a desired amount of vaporizable material, such as when a user takes a puff on the vaporizer device. Furthermore, the vacuum created in the reservoir can ultimately result in the inability to draw all of the vaporizable material into the vaporization chamber, thereby wasting vaporizable material. Various features and devices are described below that improve upon or overcome these issues. For example, various features are described herein for controlling airflow in a vaporizer device, which may provide advantages and improvements relative to existing approaches, while also introducing additional benefits as described herein.

The vaporizer devices and/or cartridges described herein include one or more features that control and improve airflow in the vaporization device and/or cartridge, thereby improving the efficiency and effectiveness of vaporizing the vaporizable material by the vaporizer device.

Figure 2A:
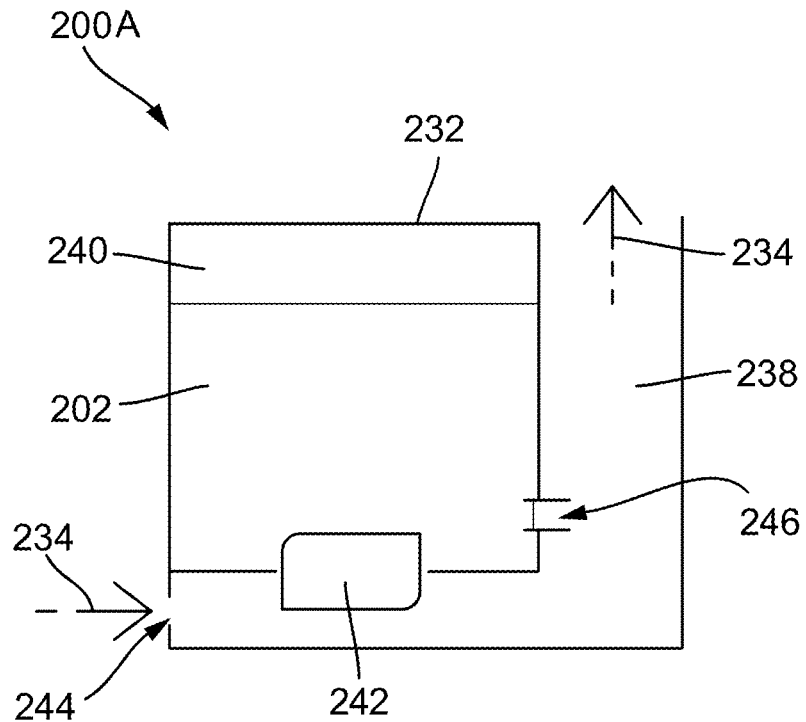
FIG. 2A illustrates a diagram of a first embodiment of a reservoir system configured for a vaporizer cartridge and/or vaporizer device for improving airflow in the vaporizer device.
Figure 2B:
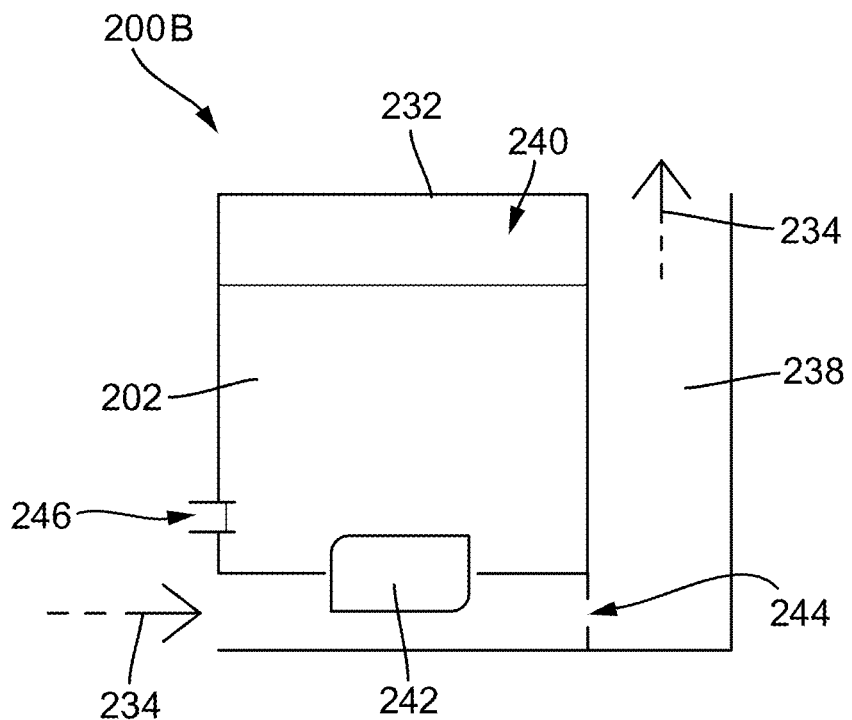
FIG. 2B illustrates a diagram of a second embodiment of a reservoir system configured for a vaporizer cartridge and/or vaporizer device for improving airflow in the vaporizer device.

FIGS. 2A and 2B illustrate diagrams of first and second embodiments, respectively, of a reservoir system 200a, 200b configured for a vaporizer cartridge (such as vaporizer cartridge 120) and/or vaporizer device (such as vaporizer 100) for improving airflow in the vaporizer device. More specifically, the reservoir systems 200a, 200b illustrated in FIGS. 2A and 2B improve the regulation of pressure within the reservoir 240 such that a vacuum created in the reservoir 240 is relieved after a user puffs on the vaporizer device. This allows the capillary action of the porous material (e.g., a wick) associated with the reservoir 240 and vaporization chamber 242 to continue to effectively draw vaporizable material 202 from the reservoir 240 into the vaporization chamber 242 after each puff.

As shown in FIGS. 2A and 2B, the reservoir systems 200a, 200b include a reservoir 240 configured to contain a vaporizable material 202. The reservoir 240 is sealed on all sides by reservoir walls 232 except for through a wick that extends between the reservoir and the vaporization chamber 242. A heating element or heater may be contained within the vaporization chamber 242 and coupled to the wick. The wick is configured to provide the capillary action that draws the vaporizable material 202 from the reservoir 240 to the vaporization chamber 242 to be vaporized into aerosol by the heater. The aerosol is then combined with airflow 234 traveling along an airflow passageway 238 of the vaporization device for inhalation by a user.

The reservoir systems 200a, 200b also include an airflow restrictor 244 that restricts the passage of airflow 234 along the airflow passageway 238 of the vaporizer device, such as when a user puffs on the vaporization device. The restriction of airflow 234 caused by the airflow restrictor 244 can allow a vacuum to be formed along a part of the airflow passageway 238 downstream from the airflow restrictor 244. The vacuum created along the airflow passageway 238 can assist with drawing aerosol formed in the vaporization chamber 242 along the airflow passageway 238 for inhalation by a user. At least one airflow restrictor 244 can be included in each of the reservoir systems 200a, 200b and the airflow restrictor 244 can include any number of features for restricting airflow along the airflow passageway 238.

As shown in FIGS. 2A and 2B, each of the reservoir systems 200a, 200b can also include a vent 246 that can be configured to selectively allow the passage of air into the reservoir 240 for increasing the pressure within the reservoir 240, such as to relieve the reservoir 240 from negative pressure (vacuum) resulting from the vaporizable material 202 being drawn out of the reservoir 240, as discussed above. At least one vent 246 can be associated with the reservoir 240. The vent 246 can be an active or passive valve and the vent 246 and can include any number of features for allowing air to pass into the reservoir 240 to relieve negative pressure created in the reservoir 240. Various embodiments of vents and vent configurations (e.g., embodiments of wick housings including one or more vents) are described in greater detail below.

For example, an embodiment of the vent 246 can include a passageway that extends between the reservoir 240 and the airflow passageway 238 and includes a diameter that is sized such that a fluid tension of the vaporizable material 202 prevents the vaporizable material 202 from passing through the passageway when the pressure is equalized across the vent 246 (e.g., the pressure in the reservoir 240 is approximately the same as the pressure in the airflow passageway 238). However, the diameter of the vent passageway can be sized such that a vacuum pressure created in the reservoir 240 disrupts the surface tension of the vaporizable material 202 along the vent passageway, thereby allowing a volume of air to pass from the airflow passageway 238 to the reservoir 240 and relieve the vacuum pressure. Once the volume of air is added to the reservoir 240, the pressure is again equalized across the vent 246, thereby allowing the surface tension of the vaporizable material 202 to prevent air from entering in the reservoir 240, as well as preventing the vaporizable material from leaking out of the reservoir 240 through the vent passageway. Additionally, the vent passageway can include a length that, in addition to the diameter, defines a volume of fluid that can be passed through the vent when a pressure differential is experienced across the vent. For example, dimensions of the vent passageway diameter can include approximately 0.3 mm to 0.6 mm, and can also include diameters having a dimension that is approximately 0.1 mm to 2 mm. The material of the vent passageway can also assist with controlling the vent, such as determining a contact angle between the walls of the vent passageway and the vaporization material. The contact angle can have an effect on the surface tension created by the vaporization material and thus effect the threshold pressure differential that can be created across the vent before a volume of fluid is allowed to pass through the vent, such as described above. The vent passageway can include a variety of shapes/sizes and configurations that are within the scope of this disclosure. Additionally, various embodiments of cartridges and parts of cartridges that include one or more of a variety of venting features are described in greater detail below.

Positioning of the vent 246 (e.g., a passive vent) and the airflow restrictor 244 relative to the vaporization chamber 242 assists with effective functioning of the reservoir systems 200a, 200b. For example, improper positioning of either the vent 246 or the airflow restrictor 244 can result in unwanted leaking of the vaporizable material 202 from the reservoir 240. The present disclosure addresses effective positioning of the vent 246 and airflow restrictor 244 relative to the vaporization chamber 242 (containing the wick). For example, a small or no pressure differential between a passive vent and the wick can result in an effective reservoir system for relieving vacuum pressure in the reservoir and resulting in effective capillary action of the wick while preventing leaking. Configurations of the reservoir system having effective positioning of the vent and airflow restrictor relative to the vaporization chamber is described in greater detail below.

As shown in FIG. 2A, the airflow restrictor 244 is positioned upstream from the vaporization chamber 242 along the airflow passageway 238 and the vent 246 is positioned along the reservoir 240 such that it provides fluid communication between the reservoir 240 and a part of the airflow passageway 238 that is downstream from the vaporization chamber 242. As such, when a user puffs on the vaporization device, a negative pressure is created downstream from the airflow restrictor 244 such that the vaporization chamber 242 experiences negative pressure. Similarly, a side of the vent 246 in communication with the airflow passageway 238 also experiences the negative pressure. As such, a small to no amount of pressure differential is created between the vent 246 and the vaporization chamber 242 during the puff (e.g., when the user draws in or sucks in air from the vaporization device). However, after the puff the capillary action of the wick will draw vaporizable material 202 from the reservoir 240 to the vaporization chamber 242 to replenish the vaporizable material 202 that was vaporized and inhaled as a result of the previous puff. As a result, a vacuum or negative pressure will be created in the reservoir 240. A pressure differential will then occur between the reservoir 240 and the airflow passageway 238. As discussed above, the vent 246 can be configured such that a pressure differential (e.g., a threshold pressure difference) between the reservoir 240 and the airflow passageway 238 allows a volume of air to pass from the airflow passageway 238 into the reservoir 240 thereby relieving the vacuum in the reservoir 240 and returning to an equalized pressure across the vent 246 and a stable reservoir system 200a.

In another embodiment, as shown in FIG. 2B, the airflow restrictor 244 is positioned downstream from the vaporization chamber 242 along the airflow passageway 238 and the vent 246 is positioned along the reservoir 240 such that it provides fluid communication between the reservoir 240 and a part of the airflow passageway 238 that is upstream from the vaporization chamber 242. As such, when a user puffs on the vaporization device, the vaporization chamber 242 and vent 246 experience little to no suction or negative pressure as a result of the puff, thus resulting in little to no pressure differential between the vaporization chamber 242 and the vent 246. Similar to the case in FIG. 2A, the pressure differential created across the vent 246 will be a result of the capillary action of the wick drawing vaporizable material 202 to the vaporization chamber 242 after the puff. As a result, a vacuum or negative pressure will be created in the reservoir 240. A pressure differential will then occur across the vent 246. As discussed above, the vent 246 can be configured such that a pressure differential (e.g., a threshold pressure difference) between the reservoir and the airflow passageway or atmosphere allows a volume of air to pass into the reservoir thereby relieving the vacuum in the reservoir. This allows the pressure to be equalized across the vent and the reservoir system 200b to be stabilized.

The vent 246 can include various configurations and features and can be positioned in a variety of positions along the cartridge, such as to achieve various results. For example, one or more vents 246 can be positioned adjacent or forming a part of the vaporization chamber or wick housing. In such a configuration, the one or more vents can provide fluid (e.g., air) communication between the reservoir and the vaporization chamber (through which airflow passes through when a user puffs on the vaporizer and is thus part of the airflow pathway). Similarly, as described above, a vent placed adjacent or forming a part of the vaporization chamber or wick housing can allow air from inside the vaporization chamber to travel into the reservoir via the vent to increase the pressure inside the reservoir thereby effectively relieving the vacuum pressure created as a result of the vaporization fluid being drawn into the vaporization chamber. As such, relief of the vacuum pressure allows for continued efficient and effective capillary action of the vaporization fluid into the vaporization chamber via the wick for creating inhalable vapor during subsequent puffs on the vaporization device by a user. The below provides various example embodiments of a venting vaporization chamber element that includes a wick housing (that houses the vaporization chamber) and at least one vent coupled to or forming a part of the wick housing for achieving the above effective venting of the reservoir.

Figure 3A:
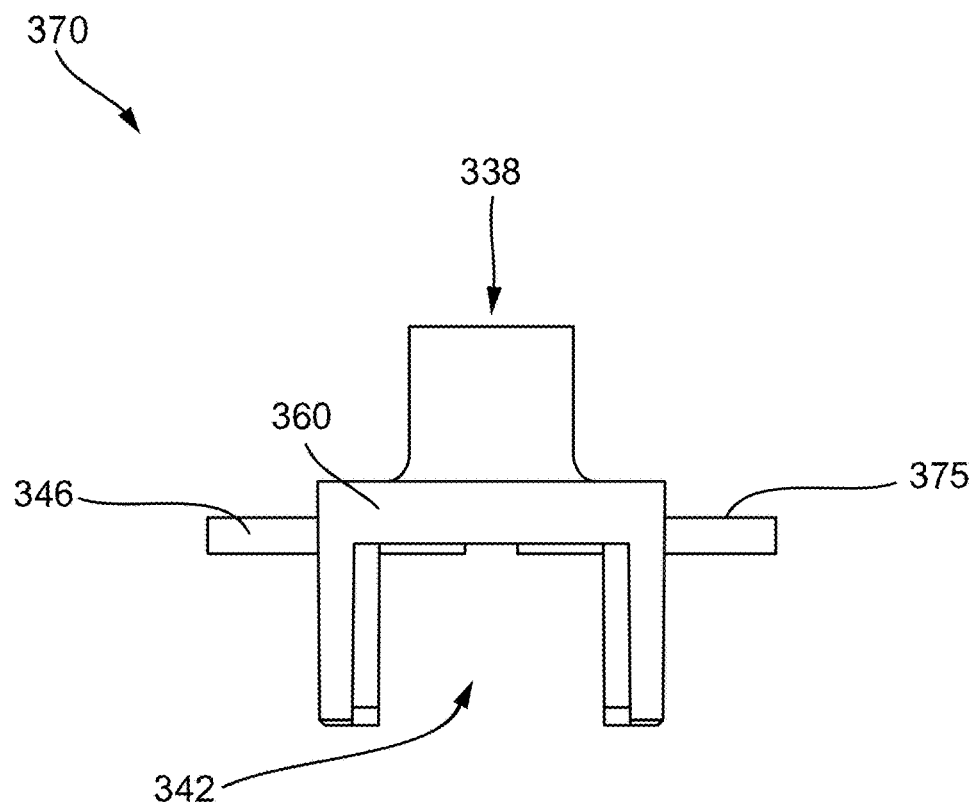
FIG. 3A shows a front view of an embodiment of a venting vaporization chamber element including a tubing vent coupled to a wick housing.
Figure 3B:
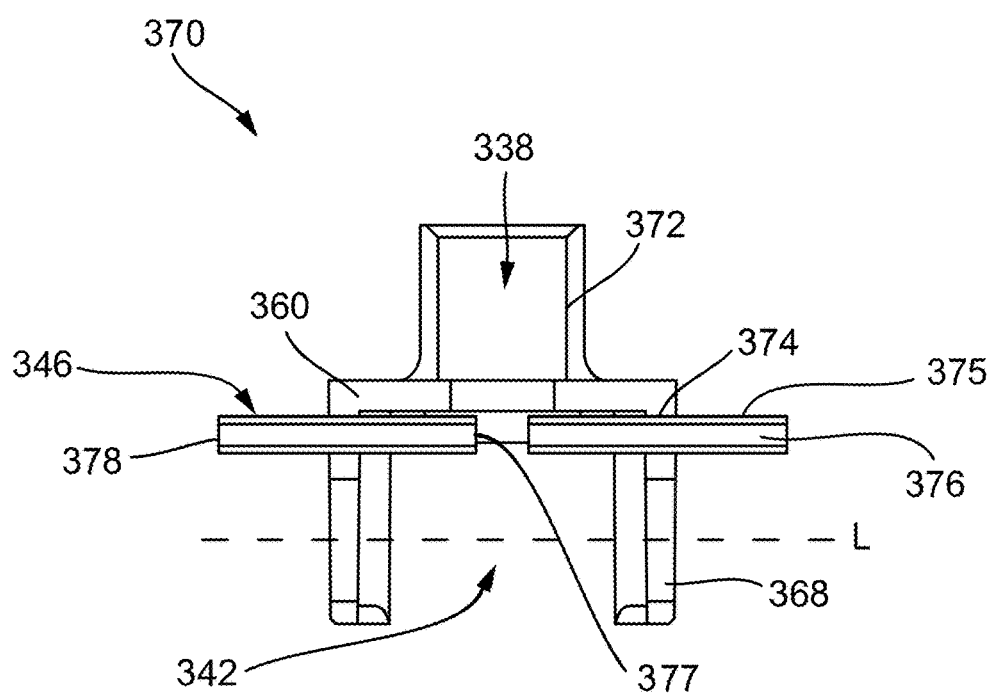
FIG. 3B illustrates a front cross-sectional view of the venting vaporization chamber element of FIG. 3A.

FIGS. 3A and 3B show an embodiment of a venting vaporization chamber element 370. The venting vaporization chamber element 370 includes a wick housing 360 and an embodiment of a vent 346 that includes a vent passageway 376 formed by a tubing 375 extending through and coupled to a part of the wick housing 360, as shown in FIG. 3A. At least one vent 346 can be included in the venting vaporization chamber element 370, such as two vents 346 positioned on opposing sides of the wick housing 360, as shown in FIGS. 3A and 3B. The wick housing 360 is configured to contain at least a part of the vaporization chamber 342, which can include a wick and heating element coupled to the wick, as described above. For example, the wick housing 360 includes at least one wick passageway 368 that allows a wick to extend (e.g., along longitudinal axis L) between the vaporization chamber 342 and reservoir, thereby allowing the wick to draw vaporizable material from the reservoir into the vaporization chamber 342.

The wick housing 360 also includes a part of the airflow passageway 338, including an airflow coupling element 372 configured to couple (e.g., by press fitting, or the like) a cannula thereto for forming another part of the airflow passageway 338. As such, when a user puffs on the vaporizer device, airflow is passed along the airflow passageway 338, including through the vaporization chamber 342 where it combines with aerosol formed by the heating element vaporizing the vaporizable material saturating the wick. As described above, after the puff when the capillary action of the wick draws vaporizable material from the reservoir to the vaporization chamber 342 thereby creating a vacuum in the reservoir, the vent 346 can allow a volume of air to travel from the vaporization chamber 342 (or airflow passageway 338) to the reservoir thereby relieving the vacuum in the reservoir and equalizing the pressure between the vaporization chamber 342 and the reservoir.

The tubing 375 forming the vent passageway 376 of the vent 346 can include a first end 377 positioned adjacent to or within the airflow passageway 338 or vaporization chamber 342 and a second end 378 disposed within the reservoir. The tubing 375 can include a variety of shapes and sizes for achieving the venting of the reservoir. As discussed above, the vent passageway 376 can be configured (e.g., have a diameter) such that the surface tension of the vaporizable material prevents leakage of the vaporizable material into the vaporization chamber but allows disruption of the surface tension to allow a volume of air to pass through the vent passageway and into the reservoir once a threshold pressure differential is reached across the vent (e.g., a vacuum is formed in the reservoir). The tubing 375 of the vent can be made out of one or more of a variety of different materials, such as various metals and/or plastics.

Figure 4A:
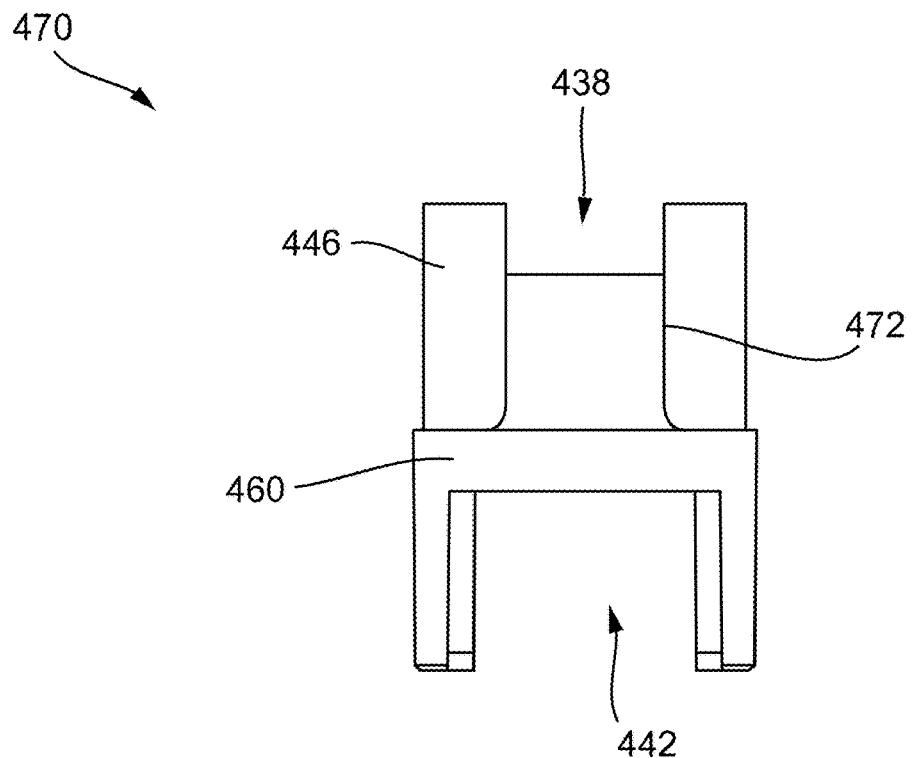
FIG. 4A shows a front view of another embodiment of a venting vaporization chamber element including a channel extending through a wick housing.
Figure 4B:
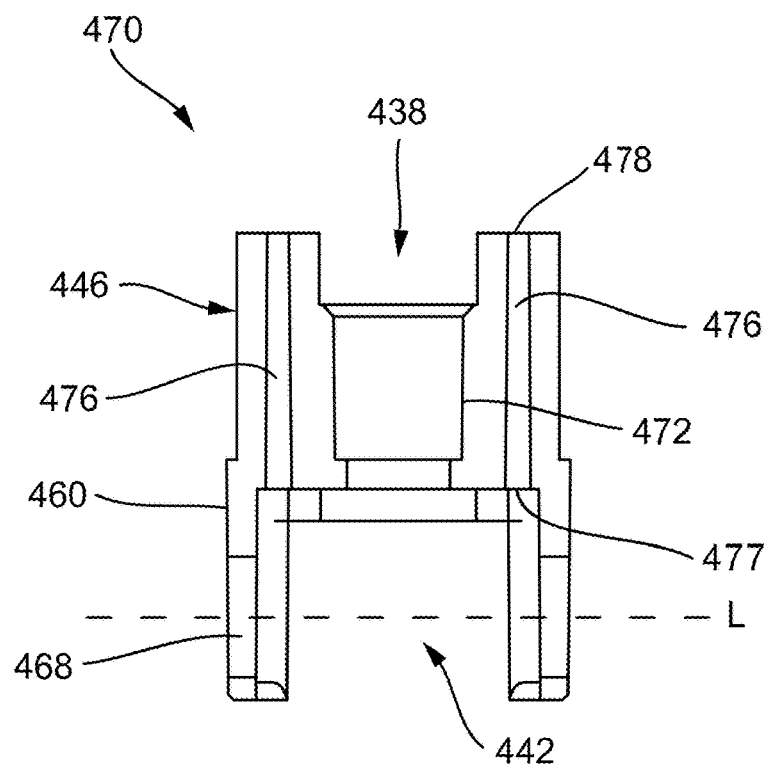
FIG. 4B illustrates a front cross-sectional view of the venting vaporization chamber element of FIG. 4A.

FIGS. 4A and 4B show another embodiment of a venting vaporization chamber element 470 including a wick housing 460 and another embodiment of a vent 446. The vent 446 illustrated in FIGS. 4A and 4B include at least one vent passageway 476 extending through the wick housing 460, such as two vent passageways molded into the wick housing 460 and extending parallel to the airflow coupling element 472. As shown in FIG. 4B, a first end 477 of the vent passageway 476 may be positioned adjacent to the airflow passageway 438 and vaporization chamber 442, and a second end 478 of the vent passageway 476 may be in communication with the reservoir. As discussed above, the wick housing 460 is configured to contain at least a part of the vaporization chamber 442, which can include a wick and heating element coupled to the wick. For example, the wick housing 460 includes at least one wick passageway 468 that allows a wick to extend (e.g., along longitudinal axis L) between the vaporization chamber 442 and reservoir, thereby allowing the wick to draw vaporizable material from the reservoir into the vaporization chamber 442. The wick housing 460 also includes a part of the airflow passageway 438, including an airflow coupling element 372 configured to couple (e.g., by press fitting, or the like) a cannula thereto for forming another part of the airflow passageway 438. As such, the vent 346 can allow a volume of air to travel from the vaporization chamber 442 (or airflow passageway 438) to the reservoir thereby relieving the vacuum in the reservoir and equalizing the pressure between the vaporization chamber and the reservoir, as described above. The vent passageway 476 can include a variety of shapes and sized, including any described herein.

Figure 5A:
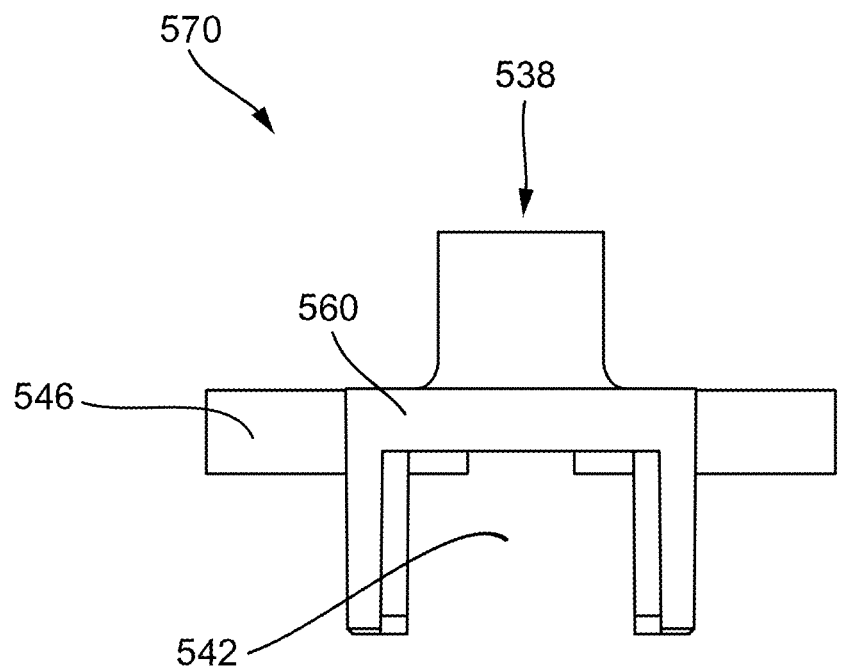
FIG. 5A shows a front view of yet another embodiment of a venting vaporization chamber element including a channel extending through a wick housing.
Figure 5B:
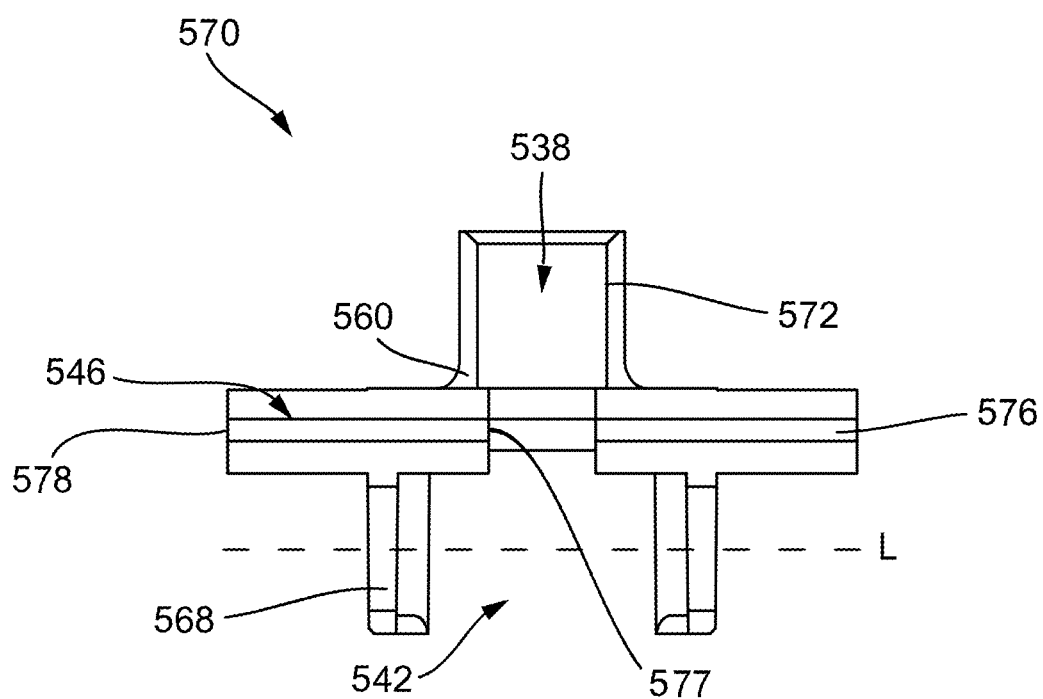
FIG. 5B illustrates a front cross-sectional view of the venting vaporization chamber element of FIG. 5A.

FIGS. 5A and 5B show yet another embodiment of a venting vaporization chamber element 570 including a wick housing 560 and another embodiment of a vent 546. The vent 546 illustrated in FIGS. 5A and 5B include at least one vent passageway 576 molded into and extending through the wick housing 560, such as two vent passageways 576 extending parallel to the longitudinal axis L of the wick passageways 568. As shown in FIG. 5B, a first end 577 of the vent passageway 576 is positioned adjacent to or in communication with the airflow passageway 538 and vaporization chamber 542, and a second end 578 of the vent passageway 576 is in communication with the reservoir.

After the puff when the capillary action of the wick draws vaporizable material from the reservoir to the vaporization chamber 542 thereby creating a vacuum in the reservoir, the vent 546 can allow a volume of air to travel from the vaporization chamber 542 (or airflow passageway 538) to the reservoir thereby relieving the vacuum in the reservoir and equalizing the pressure between the vaporization chamber 542 and the reservoir. The vent passageway 567 can include a variety of shapes and sizes, including any described herein.

Figure 6A:
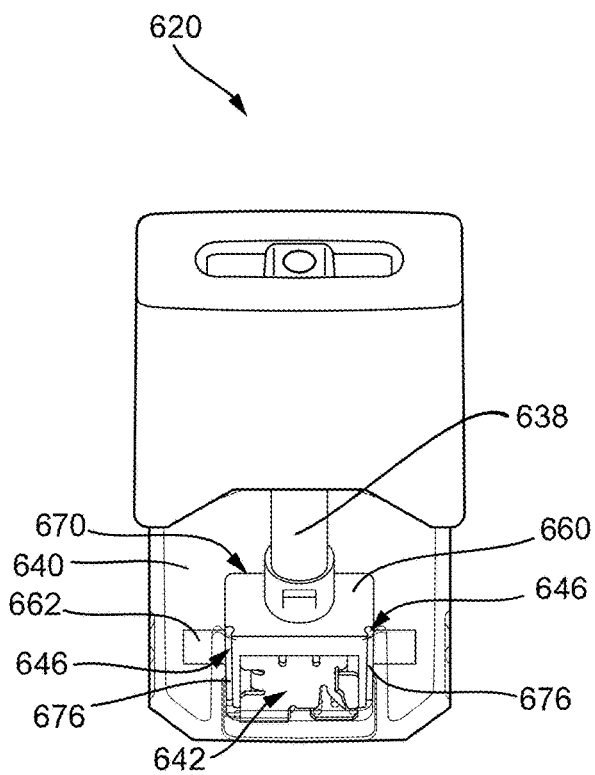
FIG. 6A shows a top perspective view of another embodiment of a venting vaporization chamber element including two vent passageways that are each defined in part by a channel extending along a front side of a wick housing.
Figure 7A:
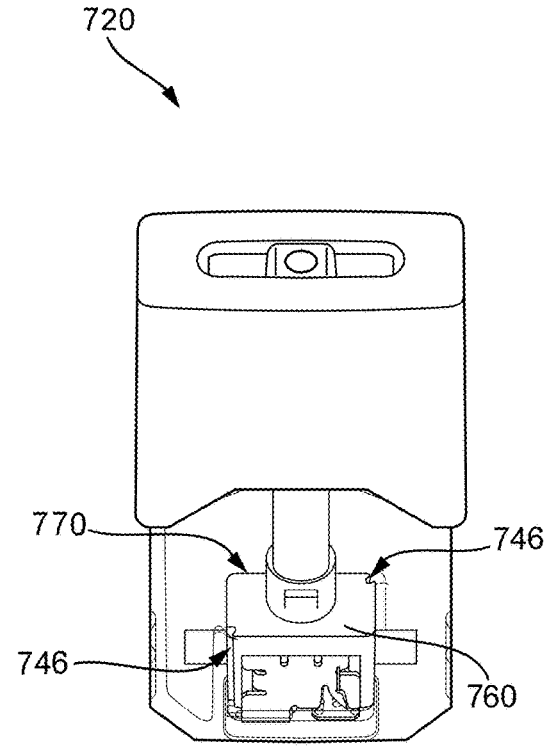
FIG. 7A shows a top perspective view of another embodiment of a venting vaporization chamber element including two vent passageways that are each defined in part by a channel extending along a side of a wick housing.
Figure 6B:
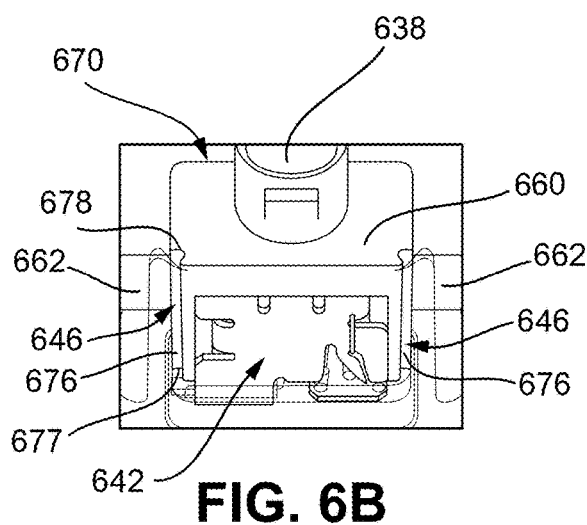
FIG. 6B illustrates a partial view of the cartridge of FIG. 6A showing the wick housing and vents.
Figure 7B:
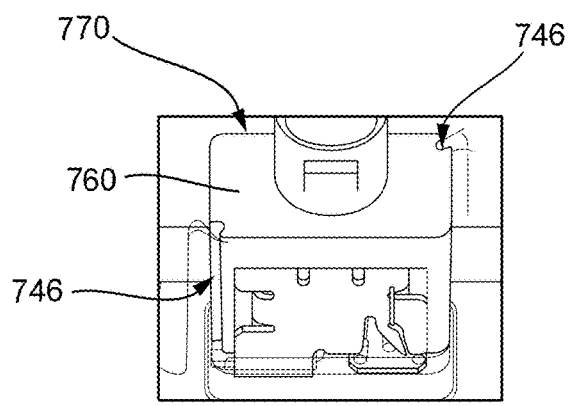
FIG. 7B illustrates a partial view of the cartridge of FIG. 7A showing the wick housing and vents.

FIGS. 6A and 6B show an embodiment of a cartridge 620 including an embodiment of a venting vaporization chamber element 670. The venting vaporization chamber element 670 can include a wick housing 660 and an embodiment of a vent 646. The vent 646 illustrated in FIGS. 6A and 6B includes at least one vent passageway 676 extending along an outer surface (e.g., along one or more sides) of the wick housing 660. As shown in FIG. 6B, the vent passageway 676 can include a channel (e.g., U-shaped) extending along an outer corner of the wick housing 660. Furthermore, the vent passageway 676 may be defined between an inner wall or feature of the reservoir 640. As such, the vent passageway 676 extends between and is defined, at least in part, by the channel extending along the wick housing and an inner wall of the reservoir 640. As shown in FIG. 6B, a first end 677 of the vent passageway 576 is positioned adjacent to or in communication with the airflow passageway 638 and vaporization chamber 642, and a second end 678 of the vent passageway 676 is in communication with the reservoir. FIGS. 6A and 6B illustrate the vent passageway 676 positioned along opposing front corners of the wick housing. FIGS. 7A and 7B illustrate another embodiment of the cartridge 720 including a venting vaporization chamber element 770 similar to the venting vaporization chamber element 670 of FIGS. 6A and 6B but with the vent 746 positioned along diagonal corners of the wick housing 760.

Similar to as discussed above, when a user puffs on the vaporizer device, airflow is passed along the airflow passageway 638 and through the vaporization chamber 642 of the cartridge 620 (or, similarly, cartridge 720) where it combines with aerosol (e.g., formed by the heating element vaporizing the vaporizable material saturating the wick 662). After the puff when the capillary action of the wick 662 draws vaporizable material from the reservoir 640 to the vaporization chamber 642 thereby creating a vacuum in the reservoir 640, the vent 646 can allow a volume of air to travel from the vaporization chamber 642 (or airflow passageway 638) to the reservoir 640 thereby relieving the vacuum in the reservoir 640 and equalizing the pressure between the vaporization chamber 642 and the reservoir 640. The vent passageway 667 can include a variety of shapes and sizes, including any described herein. For example, the vent passageway 667 can include a diameter that is sized such that a surface tension of the vaporizable material contained in the reservoir prevents passage of fluid (e.g., vaporizable material or air) unless a threshold pressure differential is created across the vent, such as when a vacuum is created in the reservoir, as discussed above.

FIGS. 8A and 8B show another embodiment of a venting vaporization chamber element 870 of a cartridge 820 that is similar to the venting vaporization chamber element 670 illustrated in FIGS. 6A and 6B such that the wick housing 860 includes at least one venting passageway 876 extending along an outer surface (e.g., along one or more sides) of the wick housing 860. As shown in FIG. 8B, the wick housing 860 includes a chamfered corner or edge that at least partly defines the vent passageway 876. Furthermore, the vent passageway 876 can be defined between an inner wall or feature of the reservoir 840. As such, the vent passageway 876 extends between and is defined, at least in part, by the chamfered corner or edge of the wick housing 860 and an inner wall of the reservoir 840. As shown in FIG. 8B, a first end 877 of the vent passageway 876 is positioned adjacent to or in communication with the airflow passageway 838 and vaporization chamber 842, and a second end 878 of the vent passageway 876 is in communication with the reservoir 840. FIGS. 8A and 8B illustrate the vent passageway 876 positioned along a front corner of the wick housing 860. FIGS. 9A and 9B illustrate another embodiment of the cartridge 920 including a venting vaporization chamber element 970 similar to the venting vaporization chamber element 870 of FIGS. 8A and 8B but with the vent 946 positioned along diagonal corners of the wick housing 960.

Similar to as discussed above, when a user puffs on the vaporizer device, airflow is passed along the airflow passageway 838 and through the vaporization chamber 842 of the cartridge 820 (or, similarly, cartridge 920) where it combines with aerosol (e.g., formed by the heating element vaporizing the vaporizable material saturating the wick 862). After the puff when the capillary action of the wick 862 draws vaporizable material from the reservoir 840 to the vaporization chamber 842 thereby creating a vacuum in the reservoir 840, the vent 846 can allow a volume of air to travel from the vaporization chamber 842 (or airflow passageway 838) to the reservoir 840 thereby relieving the vacuum in the reservoir and equalizing the pressure between the vaporization chamber 842 and the reservoir. The vent passageway 867 can include a variety of shapes and sizes, including any described herein.

Figure 10:
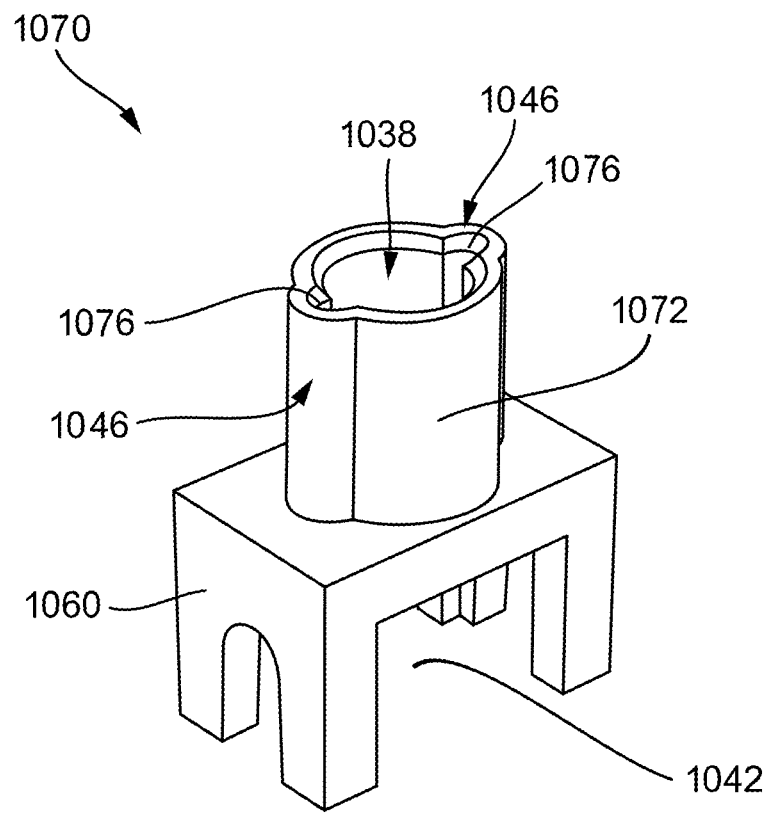
FIG. 10 shows another embodiment of a venting vaporization chamber element including at least one molded vent joined with and extending parallel to the airflow passageway.

FIG. 10 shows another embodiment of a venting vaporization chamber element 1070 including a wick housing 1060 and another embodiment of a vent 1046. The vent 1046 illustrated in FIG. 10 includes two vent passageways 1076 molded into the wick housing 1060. Additionally, the vent passageways 1076 extend parallel to and merge with the airflow coupling element 1072 configured to couple (e.g., by press fitting, or the like) a cannula thereto for forming another part of the airflow passageway 1038. As such, when the cannula is coupled to the airflow coupling element 1072, the vent passageways 1076 can extend along the side of the cannula and extend between the reservoir and vaporization chamber 1042.

Figure 11:
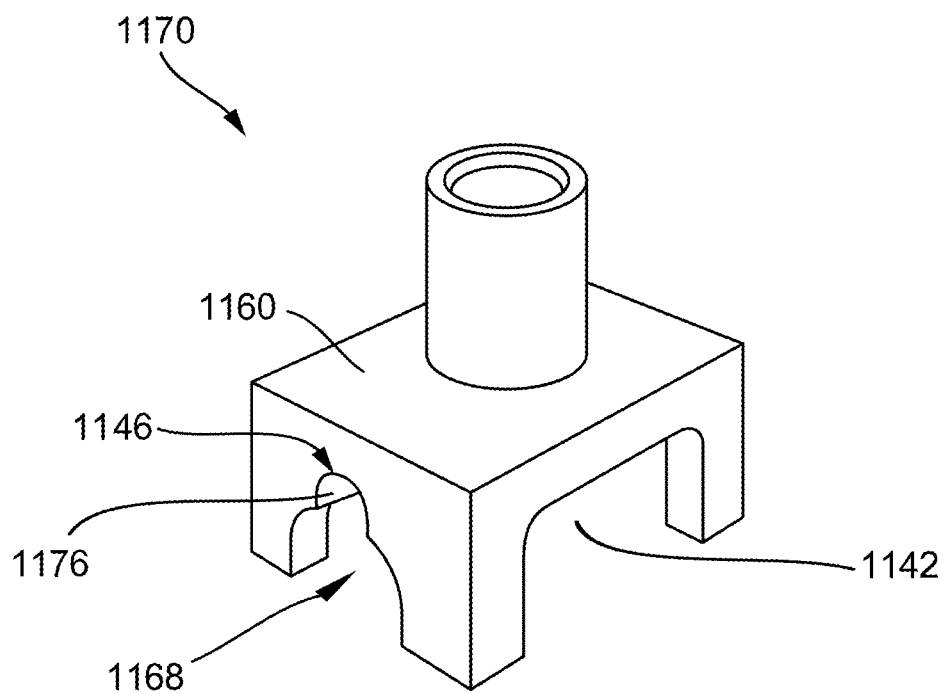
FIG. 11 show another embodiment of a venting vaporization chamber element including at least one molded vent joined with and extending parallel to a wick passageway.

FIG. 11 show another embodiment of a venting vaporization chamber element 1170 including a wick housing 1160 and another embodiment of a vent 1146. The vent 1146 illustrated in FIG. 11 includes a vent passageway 1176 molded into the wick housing 1060. Additionally, the vent passageway 1076 extends parallel to and merges with the wick passageway 1168 configured to allow a wick to extend therealong. As such, when the wick is coupled to and extends along the wick passageway 1168, the vent passageway 1176 can extend along the side of the wick and extend between the reservoir and vaporization chamber 1142.

In some implementations, a flattened wick design may be used. Flat surface sides can have an increased surface area over traditional cylindrical-shaped wicks, thereby providing increased vapor delivery from the reservoir to the vaporization chamber. A flattened wick design may have favorable wicking properties based on geometry, and may also improve manufacturing (e.g., based on ease of insertion, ability for di-cutting, etc.). In some implementations, a heating element, such as a coil or wire, can be placed along one or more of the sides of the wick. In some implementations, the heating element can be wrapped around the wick. The wick can be formed of one or more of a variety of materials, such as silica, cotton, fiberglass, etc. In some aspects, cotton wicks can provide higher capillary action compared to wicks made of other materials, thereby assisting with providing increased vapor delivery from the reservoir to the vaporization chamber.

Figure 12A:
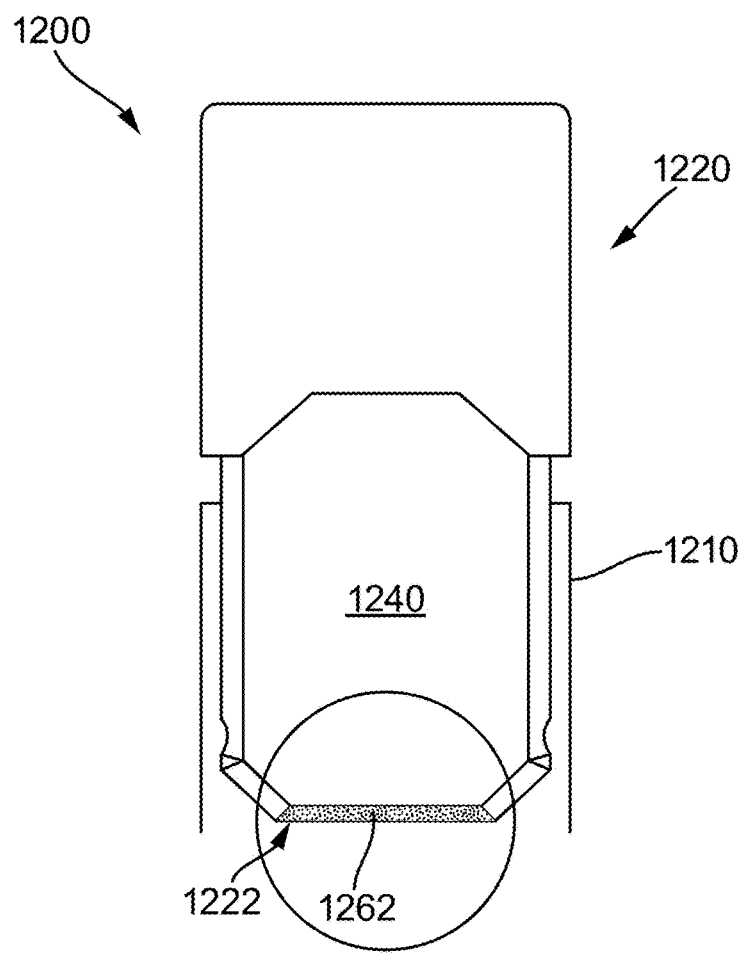
FIG. 12A shows a schematic diagram illustrating features of a vaporizer cartridge having a flattened wick.
Figure 12B:
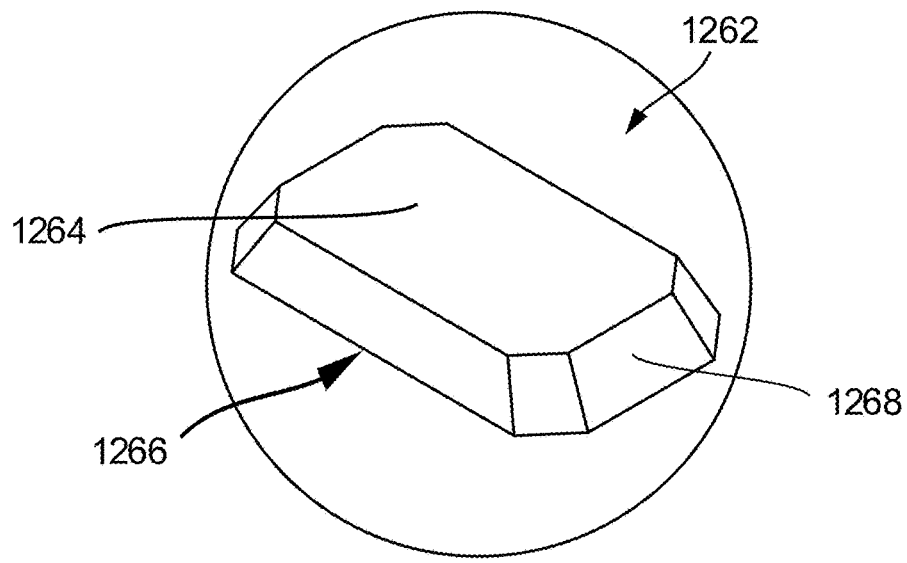
FIG. 12B illustrates a top perspective view of the flattened wick of FIG. 12A.

FIG. 12A shows a cartridge 1220 inserted in a vaporizer device 1200, with the cartridge including an embodiment of a flattened wick 1262. In some implementations, the flattened wick 1262 may be disposed proximate to an insertable end 1222 of the cartridge 1220 and in fluid communication with the reservoir 1240. FIG. 12B illustrates a perspective close-up view of the flattened wick 1262, consistent with implementations of the current subject matter. As shown in FIG. 12B, the flattened wick 1262 can include a top surface 1264 and a bottom surface 1266 that are flat and parallel to each other. The sides 1268 of the flattened wick 1262 can be angled or parallel relative to each other. One or more corners of the flattened wick can be angled relative to the top or bottom surface, and can be chamfered, as shown in FIG. 12B. Other implementations of the flattened wick 1262 are within the scope of this disclosure.

Controlling and/or encouraging airflow throughout the airflow passageway of the cartridge and/or controlling air pressure in certain portions of the cartridge can assist with drawing vaporizable material into the vaporization chamber to thereby ensure a desired amount of aerosol production by the vaporizer device. Some implementations of the current subject matter described herein include one or more air control features that passively and/or actively allow air to enter the reservoir to replace the vaporizable material exiting the reservoir. Such configurations can be enabled and/or assisted by negative pressure created by a user puffing on the vaporizer device, as will be explained in greater detail below.

In some implementations, one or more parts of a cartridge (e.g., reservoir) can include one or more airflow control features, which can include one or more of the various vent embodiments described herein. The airflow control feature can help to control airflow using various mechanisms, such as through passive systems, passively powered but actively controlled systems, and/or active systems, among others. Various airflow control feature embodiments are described in greater detail below.

Figure 13A:
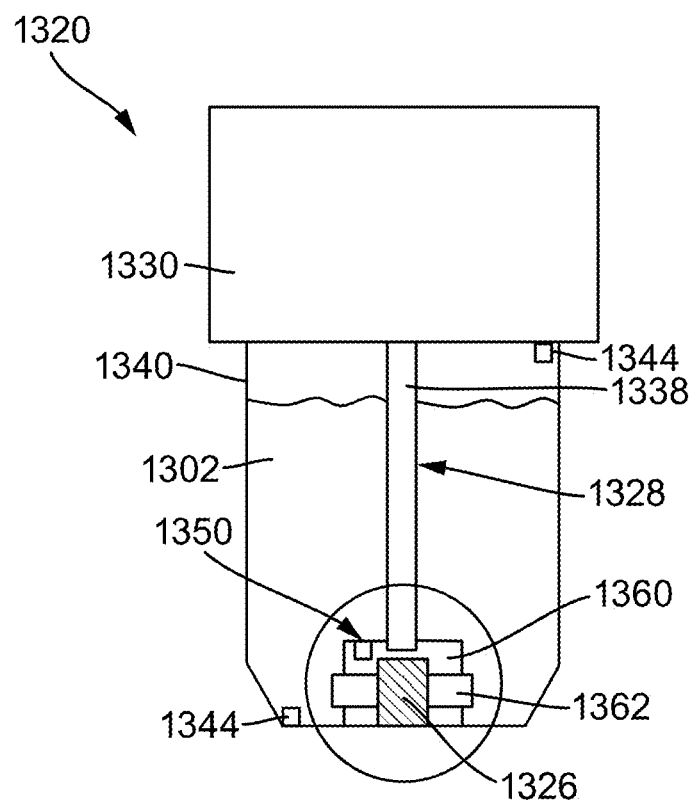
FIG. 13A illustrates another embodiment of a vaporizer cartridge consistent with implementations of the current subject matter.
Figure 13B:
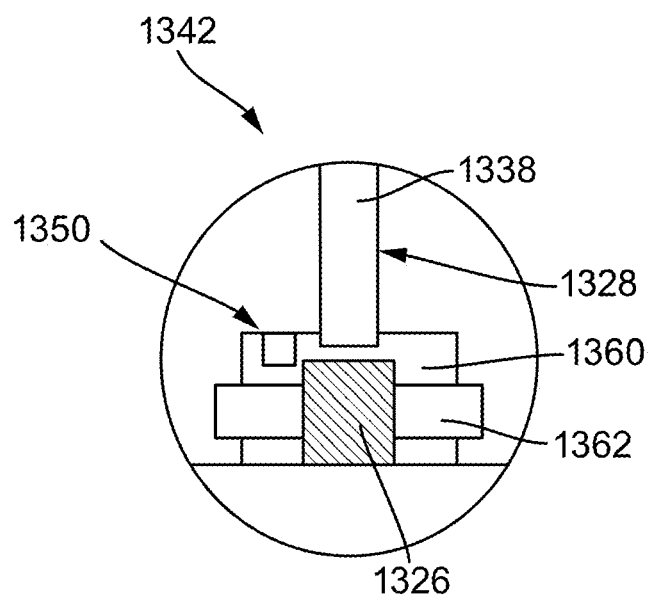
FIG. 13B illustrates a front partial view of the vaporizer cartridge of FIG. 13A.

FIG. 13A illustrates a cartridge 1320 consistent with implementations of the current subject matter and FIG. 13B illustrates a close-up view of a schematic of a vaporization chamber 1342 of the cartridge 1320 consistent with implementations of the current subject matter. The cartridge 1320 includes a reservoir 1340 for holding a vaporizable material 1302, a mouthpiece 1330, an airflow passageway 1338 (defined by a cannula 1328) through the reservoir 1340, a wick housing 1360, and/or a wicking element (e.g., a wick) 1362. The wick 1362 is coupled to a resistive heating element (e.g., a coil) that is connected to one or more electrical contacts (e.g., plates 1326) and power source. A vaporization chamber or heater 1350 of the cartridge 1320 can include the wick 1362 extending between the plates 1326, as well as the resistive heating element in contact with the plates 1326 and the wick 1362. The wick housing 1360 can surround at least a portion of the heater 1350 and/or at least a portion of the cannula 1328 of the airflow passageway 1338.

The wick 1362 can draw the vaporizable material 1302 from the reservoir 1340, from one or both ends of the wick 1362 and/or radially along a length of the wick 1362 due at least in part to a material of the wick 1362 and/or perforations in the wick 1362. When a user puffs on the mouthpiece 1330 of the cartridge 1320, air flows into the cartridge 1320 through an inlet. The heating element may be activated, e.g., by a pressure sensor, pushbutton, motion sensor, flow sensor, or other approach capable of detecting that a user is taking a puff or otherwise inhaling through a flow path of the vaporizer device. When the heating element is activated, the coil may have a temperature increase as a result of current flowing through the heating element to generate heat. The heat is transferred to at least a portion of the vaporizable material in the wick 1362 through conductive, convective, and/or radiative heat transfer such that at least a portion of the vaporizable material vaporizes. The incoming air into the vaporizer device flows over the heated wick/heating element, stripping away the vaporized vaporizable material, where it is condensed and exits as an aerosol via the mouthpiece 1330 to a user.

A wick 1362 consistent with implementations of the current subject matter can provide a capillary pathway, for vaporizable material within the reservoir 1340, through and/or into the wick 1362. The capillary pathway is generally large enough to permit wicking to replace vaporized liquid transferred from the reservoir by capillary action during use of the vaporizer device, but may be small enough to prevent leakage of the vaporizable fluid material out of the vaporizer cartridge during normal operation, such as when applying pressure to (e.g., squeezing) the vaporizer cartridge. The wick housing 1360 and/or the wick 1362 may be treated to prevent leakage. For example, the wick 1362 and/or the wick housing 1360 may be coated after filling to prevent leakage and/or evaporation through the wick 1362 until activated by connecting to a vaporizer body and/or applying current through the plates 1326 (e.g., operation in a vaporizer device), or otherwise using the vaporizer cartridge. Any appropriate coating may be used, including a heat-vaporizable coating (e.g., a wax or other material) or the like.

A wick consistent with implementations of the current subject matter may have an orientation other than that shown in the exemplary cartridge illustrations of FIGS. 13A and 13B. For example, the wick 1362 shown in FIGS. 13A and 13B extends horizontally between two side portions of the vaporizer cartridge. However, the wick is not limited to this orientation and may, for example, extend internally along a length of the vaporizer cartridge with the heating element at one end of the wick. Other orientations and configurations are also possible.

The passive systems to control airflow via the airflow control feature 1344 can include a pore and/or a check valve, among other configurations. For example, the airflow control feature 1344 can include a pore that includes an opening extending through a wall of the reservoir and/or the cartridge. The wall can include a wall thickness that extends from an inner surface of the reservoir and/or the cartridge body to an outer surface of the reservoir and/or cartridge body. The airflow control feature 1344 can be shaped and/or sized such that surface tension can hold the vaporizable material in the reservoir 1340. For example, the airflow control feature 1344 can be circular in shape. Other shapes and configurations are within the scope of this disclosure.

In some implementations, positioning the airflow control feature 1344 in certain locations along the cartridge can improve and/or otherwise enhance the efficiency and/or effectiveness of vaporization of the vaporizable material. For example, placement of the pore away from the ends of the wick 1362 can prevent or limit either end of the wick 1362 from drying out by providing an alternate air inlet path.

In such configurations, the airflow control feature 1344 can be positioned in a location such that an exterior side of the airflow control feature 1344 is exposed to a higher pressure (e.g., closer to atmospheric pressure) than the wick 1362 during a puff. In some implementations, the airflow control feature 1344 can be positioned upstream of the wick 1362 (for example above the wick 1362 as shown in the orientation of FIGS. 13A and 13B). In some implementations, at least one flow restriction, such as a microperforation and/or an electrical contact pad positioned at the lower portion of the vaporizer cartridge can be positioned between the wick and the pore.

Positioning the airflow control feature 1344 upstream of the wick 1362 along the airflow passageway 1338 can force air outside of the pore into the reservoir 1340 during and/or after a puff. In such configurations, at least during the puff, the air positioned exterior to the pore has a higher pressure than the air positioned inside the reservoir 1340. The pressure differential between the air outside of the reservoir 1340 and the air inside of the reservoir 1340 can cause the pore to define a primary air inlet, as the air passes into the reservoir 1340 through the pore. Such configurations can desirably create a strong and/or tunable amount of additional pressure to force vaporizable material into the wick 1362 beyond that which would naturally be conveyed by capillary pressure. Accordingly, the total rate of vaporization of the vaporizable material during a puff may not be limited by wick material properties alone. Rather, the total rate of vaporization of the vaporizable material during a puff can be desirably controlled and/or altered by incorporating an airflow control feature 1344 and/or placing the airflow control feature 1344 in a desired location.

As mentioned above, placement of the airflow control feature 1344 can improve and/or enhance the rate of vaporization of the vaporizable material at least during and/or after a puff. In some implementations, the airflow control feature 1344 can be placed close to and/or between the ends of the wick 1362. In certain situations, placing the airflow control feature 1344 a large distance from the wick 1362, such as at a top end portion of the reservoir 1340, a hydrostatic differential pressure between the airflow control feature 1344 and the wick 1362 can allow air to enter the reservoir 1340 and vaporizable material to drain out the wick 1362. The additional hydrostatic differential pressure can undesirably force too large of an amount of the vaporizable material to drain out of the wick, such as at a faster or much faster rate than the vaporizable material is being vaporized, depending on the orientation of the vaporizer cartridge. In some implementations, a large hydrostatic differential pressure can undesirably cause all of the vaporizable material in the reservoir to drain. If the distance between the airflow control feature 1344 and the wick is relatively small (such as compared with the distance between the ends of the wick) then the additional hydrostatic differential pressure can be negligible. Such configurations can help to limit or prevent leakage of the vaporizable material. Thus, it can be desirable for the airflow control feature 1344 to be positioned gravitationally close to the wick 1362, such as at and/or adjacent to the wick housing 1360, between the ends of the wick 1362, and/or upstream of the wick 1362 such as in the airflow passageway 1338.

In some implementations, the airflow control feature 1344 can include a valve, such as a duck bill or a check valve, among other valves. The airflow control feature 1344 including the valve can be desirably positioned in the same and/or similar locations as described above. The valve can allow air to enter the reservoir 1340, but limit or prevent air from exiting the reservoir 1340.

The valve of the airflow control feature 1344 can include a cracking pressure. The cracking pressure can be the minimum upstream pressure at which the valve will operate (e.g., allow air to pass through). Positioning the airflow control feature 1344 having the valve gravitationally close to the wick 1362, such as at and/or adjacent to the wick housing 1360, between the ends of the wick 1362, upstream of the wick 1362 such as in the airflow passageway 1338, and/or at an outer lower edge of the cartridge 1320, such as a lower corner of the vaporizer cartridge, among other positions, can cause the cracking pressure to be close to zero pressure or negligible. Such configurations can be desirable since the pressure differential created by the capillary pressure of the wick can be small. If the cracking pressure is too high, the valve of the airflow control feature 1344 may not crack (e.g., open) and may not allow air to pass through the valve.

In some implementations, the airflow control feature 1344 can include a venting material or membrane. The venting material or membrane can be positioned over an opening in the cartridge, such as an exterior surface of the pore. The venting material can include an expanded polytetrafluoroethylene (PTFE) surface, among other materials. The venting material or membrane can allow air to enter the reservoir and/or can help to limit or prevent vaporizable material from exiting the reservoir. The venting material can be desirably positioned in the same and/or similar location as described above. For example, in some embodiments, the venting material or membrane can act as a heat seal over the pore.

The passively powered but actively controlled systems to control airflow via the airflow control feature 1344 can include a magnetic diaphragm valve, a bent nose valve, and/or a passive septum system, among other configurations. At least a portion of the magnetic diaphragm valve, the bent nose valve, and/or the passive septum system can be positioned in the same and/or similar location as described above.

In some implementations, the passive septum system can include a septum, such as a re-sealing pierceable elastomer septum. The septum can be positioned at a lower portion, such as a bottom side of the vaporizer cartridge. In such configurations, the vaporizer device can include a needle that pierces the septum upon insertion of the vaporizer cartridge into the vaporizer device. The passive septum system can include a vent, among other components. The vent can be positioned under the needle when assembled. The vent can desirably direct airflow to the environment. Such configurations can allow venting directly to the environment even in situations in which the air pressure outside of the vaporizer cartridge is lower.

In some implementations, the passive septum system can include a valve. The valve can desirably control airflow into the reservoir. For example, the valve can be mechanically and/or electronically controlled. In some implementations, the passive septum system includes a microprocessor. The microprocessor can desirably open and/or close the valve. By controlling the operation of the valve, the microprocessor can control a flow rate of air and/or liquid into or out of the reservoir, such as an average flow rate of air and/or liquid. Such configurations can allow for easier estimation of the rate of vaporization by using power and/or temperature measurements from the heating element using one or more sensors, for example. Such configurations can desirably allow the valve to be closed when the vaporizer device is not in use, minimizing oxygen and/or moisture exchange with the environment. Such configurations can desirably prolong the lifespan of the cartridge.

The active systems to control airflow via the air control feature can include an active septum system, among other configurations. The active septum system can include a septum, such as a re-sealing pierceable elastomer septum. The septum can be positioned at a lower portion of the cartridge, such as a bottom side of the vaporizer cartridge. In such configurations, the vaporizer device can include a needle that pierces the septum upon insertion of the vaporizer cartridge into the vaporizer device.

In some implementations, the active septum system can include a pump. The pump can desirably control airflow into the reservoir. For example, the pump can be mechanically and/or electronically controlled. In some implementations, the active septum system includes a microprocessor. The microprocessor can desirably start and/or start the pump. The microcontroller can determine an appropriate amount of air to pump into the reservoir to achieve a desired rate of vaporization. In such configurations, the flow rate of air through the system desirably may not depend or may minimally depend on the negative pressure applied by the user during a puff. Rather, the pump can directly control the flow of air and allow more or less flow of air than would be passively driven by the user's puff and an open valve, for example. In some implementations, the pump can reduce mechanical complexity of the airflow control feature and/or can allow for a high-frequency and/or low stroke pump, such as a PCB scale piezo pump. The piezo pump can create a high flow rate and/or can maximize air pressure to desirably control the flow of air and/or liquid throughout the system.

Separated Vapor Path

It can be desirable to prevent leakage from the reservoir to the environment and/or to other portions of the vaporizer cartridge. The vaporizer cartridge can be pressurized by an air seal positioned at an opposite end of vaporizer cartridge from the heater. The air seal can create a back vacuum to help to limit or prevent leakage and retain the vaporizable material within the reservoir. In some embodiments, the vaporizer device includes a pressure sensor. The pressure sensor can determine whether the vaporizer device, such as the heater, should be activated, for example, by determining whether a user's puff is taking place. The pressure sensor may rely on a pressure signal caused by the flow of air in communication with the pressure sensor. The pressure signal may fail when liquid follows the same path, such as by damaging the pressure sensor and/or or reducing the sensitivity of the pressure sensor.

Some vaporizer cartridges include a single airflow pathway that extends across the vaporization chamber and directly out to the user, such as through a center of the reservoir. The air path may transfer the pressure signal caused by the user's breath to the pressure sensor, conveying vapor from the heater to the user, mixing vapor with cold air to condense the vapor into an aerosol, and/or providing the air that will be vented back into the reservoir during or after the puff. Some vaporizable material that exits the reservoir may not become vaporized and vaporizable material that re-condenses in the airflow passageway may be freely able to flow back to the pressure sensor, which can damage the pressure sensor. Surface tension of vaporizable material blocking the pressure sensor can undesirably reduce the pressure signal and/or reduce the likelihood that the vaporizer device will properly activate. The following disclosure includes vaporizer embodiments that include a separate pressure-sensing pathway that overcomes the above issues.

Figure 14A:
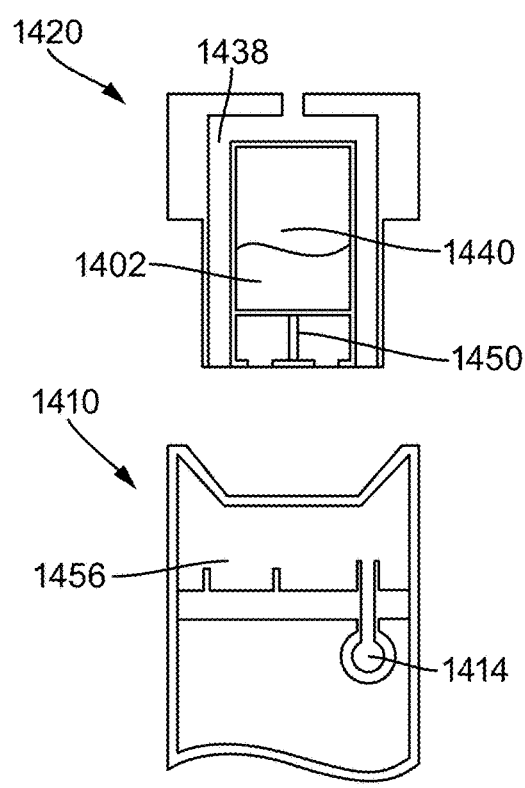
FIG. 14A illustrates another embodiment of a vaporizer cartridge being inserted into another embodiment of a vaporizer device body including a pressure sensor.
Figure 14B:
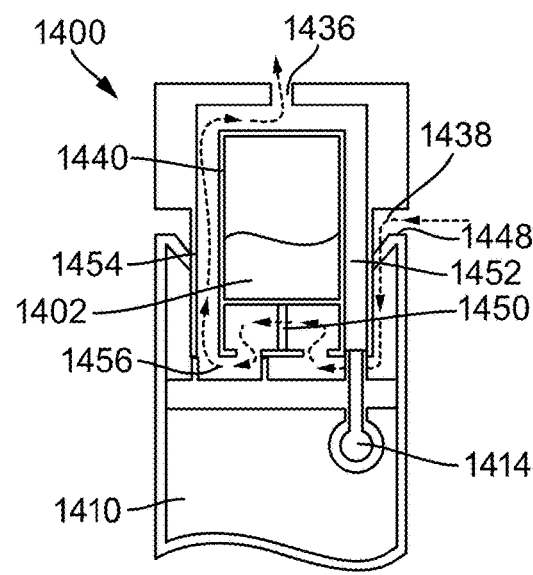
FIG. 14B illustrates a front view of the vaporizer cartridge inserted into the vaporizer device body of FIG. 14A.

FIG. 14A illustrates a schematic of a cartridge 1420 and a vaporizer device 1400 according to implementations of the current subject matter. FIG. 14B illustrates a schematic of the cartridge 1420 inserted into the vaporizer device 1400 according to implementations of the current subject matter. As shown in FIGS. 14A and 14B, the cartridge 1420 can include a reservoir 1440 and/or a vaporization chamber or heater 1450. The reservoir 1440 can be at least partially surrounded by an airflow passageway 1438. The airflow passageway 1438 can include a pressure path 1452 and/or a vapor path 1454. The vaporizer device 1400 can include a pressure sensor 1414 and/or a vapor routing gasket 1456.

FIG. 14B illustrates an example airflow that passes through the airflow passageway 1438 of the assembly of the cartridge 1420 and the vaporizer device 1400. The air can enter the assembly through an inlet 1448, pass through an airflow passageway 1438, pass through the heater 1450, pass through the vapor routing gasket 1456, pass through the vapor path 1454, and/or through an outlet 1436. Additionally, a pressure path 1452 is a separate air channel that extends between the outlet of the cartridge and the pressure sensor 1414, as shown in FIG. 14B. This allows the pressure sensor 1414 to measure the pressure signal as a static or nearly static measurement rather than a dynamic measurement. The static measurement can be more accurate than the dynamic measurement of the pressure signal.

Figure 14C:
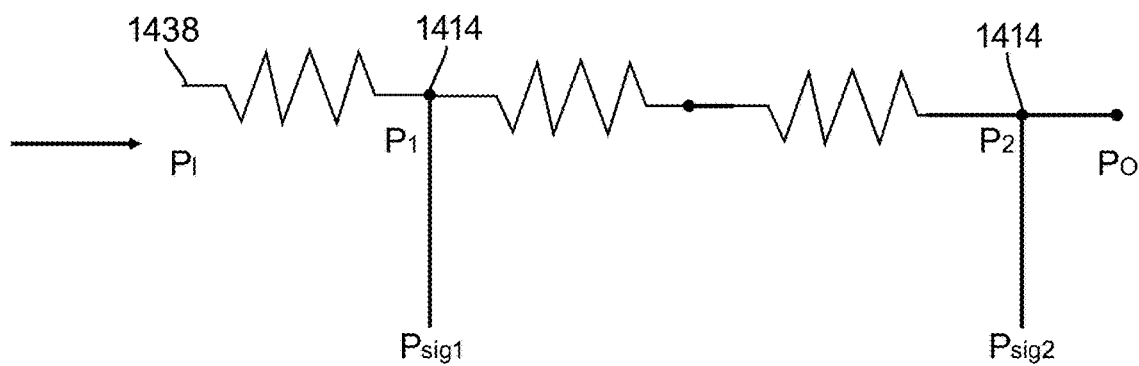
FIG. 14C illustrates an example schematic of the pressure sensor in the vaporizer device body of FIG. 14A positioned at various locations along an airpath.

FIG. 14C illustrates an example schematic of a pressure sensor 1414 positioned at various locations in the airflow passageway 1438 and various restrictions within the cartridge 1420. In some implementations, the pressure sensor 1414 can measure a pressure signal at $P_{sig1}$. The pressure signal at $P_{sig1}$ represents the pressure drop between a pressure $P_1$ at the inlet and a pressure $P_1$ at a first location along the airpath. The pressure signal measured by the pressure sensor 1414 can be small if the resultant resistance between the inlet (at $P_1$) and the first location (at $P_1$) is large relative to the strength of the user's puff. Thus, it can be undesirable to position the pressure sensor 1414 near the inlet. Instead, it may be desirable to position the pressure sensor 1414 further downstream in the airflow passageway 1438 at a second location (at $P_2$) to measure a pressure signal $P_{sig2}$. The pressure path 1452 can have a small diameter relative to a volume of the cartridge 1420 since the pressure path 1452 does not need to transmit a significant amount of airflow. The additional separate pressure path 1452 air channel may take up minimal space within the cartridge 1420, thereby reducing the overall size of the cartridge 1420. In some implementations, the pressure path 1452 includes a diameter that is smaller than a diameter of the vapor path 1454. In some implementations, the diameter of the pressure path 1452 is equal to or greater than the diameter of the vapor path 1454. The separate air channel can desirably separate the vaporized vaporizable material 1402 passing through the vapor path 1454 from the pressure path 1452 that leads to the pressure sensor 1414. Such configurations can desirably prolong the life of the pressure sensor and improve pressure readings, thus improving the functioning of the vaporizer device.

In some implementations, it can be desirable to position the inlet 1448 and the outlet 1436 on the same side of the cartridge 1420. Directing the air directly from the inlet 1448 to the outlet 1436 rather than through a reservoir can allow for the cartridge 1420 to be more easily sealed at the top portion of the reservoir 1440. In some implementations, the cartridge 1420 can include a seal, such as a face seal to seal the inlet 1448 and/or the outlet 1436.

Figure 14D:
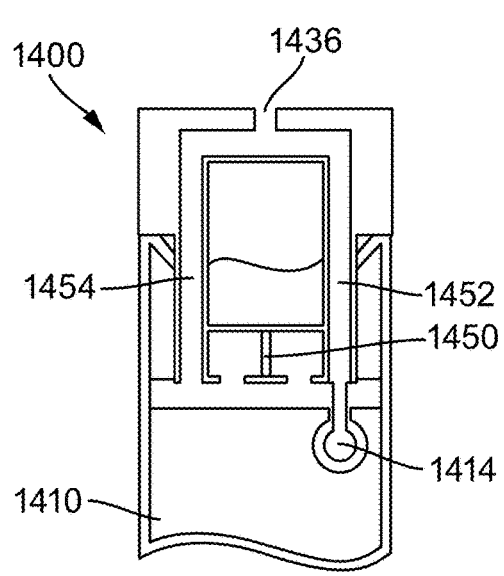
FIG. 14D illustrates an example coupling of the vaporizer cartridge and the vaporizer device body of FIG. 14A.

For example, FIG. 14D shows the cartridge 1420 and the vaporizer device 1400 in a first position where the inlet and outlet are sealed closed (e.g., prevent airflow therebetween). As shown in FIG. 14D, the cartridge 1420 is pushed further into the vaporizer device 1400 to seal the inlet 1448 and/or the outlet 1436, which are positioned along opposing sides of the cartridge 1420. Such configurations allow for a better seal when the cartridge 1420 is not in use, such as when the vaporizer device 1400 is being stored and/or between puffs or uses. Such configurations can prolong the usage life of the cartridge 1420. For example, the seal helps to limit or prevent moisture from entering and/or exiting the vaporizer cartridge. The seal can desirably help to limit or prevent leaks from the reservoir. The seal can desirably limit or prevent unwanted air from mixing with the vaporizable material. During use, the cartridge can be positioned in a second position (for example, as shown in FIG. 14E) where the inlet and outlet are open thereby allowing airflow therebetween.

FIG. 14D schematically illustrates an example of an assembly of the cartridge 1420 and the vaporizer device 1400 according to implementations of the current subject matter. The cartridge 1420 includes a reservoir 1440 and/or a heater 1450. The reservoir 1440 is at least partially surrounded by an airflow passageway 1438. The airflow passageway 1438 includes a pressure path 1452, a vapor path 1454, and/or a quenching path 1458. The vaporizer device 1400 includes a pressure sensor 1414 and/or a vapor routing gasket 1456.

Figure 14E:
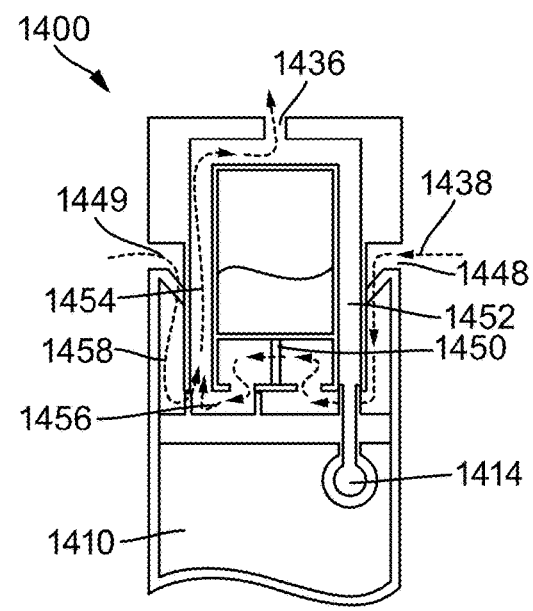
FIG. 14E illustrates an example quenching airflow pathway of the vaporizer cartridge and vaporizer device body of FIG. 14A.

FIG. 14E illustrates an example airflow that passes through an airflow passageway 1438 of the cartridge and vaporizer device assembly 1400. Air enters the cartridge and vaporizer device assembly 1400 through inlet 1448, passes through an airflow passageway 1438 and passes by the pressure sensor 1414 at one end of the pressure path 1452. The air then passes through the heater 1450, through the vapor routing gasket 1456, through the vapor path 1454, and finally out through an outlet 1436. The cartridge can include a secondary inlet and/or airflow passageway that includes airflow that does not pass through the heater or vaporization chamber and, instead, merges with the airflow-containing aerosol (e.g., merges with airflow that has already passed through the vaporization chamber). For example, air can enter the airflow passageway 1438 through a second inlet 1449, as shown in FIG. 14E. The air flowing through the second inlet 1449 can pass through the quenching path 1458 and into the vapor path 1454 to mix with the vaporized vaporizable material 1402 in the vapor path 1454.

The quenching path 1458 can desirably allow the vaporized vaporizable material to mix with a larger volume of quenching air before the mixed airflow reaches the user. The mixture of the vaporized vaporizable material with the volume of quenching air can cause the mixed air to condense and/or create a visible vapor. The quenching path 1458 can allow a separate amount of air to flow over the heater 1450 than an amount of air that the user draws in during a puff. For example, the user may prefer a certain flow rate and/or pressure drop during a puff. In some situations, the user may prefer a greater flow rate than is required to obtain a high rate of vaporization at the heater 1450. The quenching path 1458 can thus allow various flow rates and pressure drops for achieving desired user experiences.

Separating the quenching air from the airflow that travels over the heater can desirably provide design flexibility. In some implementations, the quenching air can be routed separately to allow the airflow over the heater to be routed through one or more valves, such as check valves (not shown). This can allow the vaporizable material in the reservoir to be sealed, except for during a puff, allowing the vaporizer device to have high moisture and/or oxygen barriers between uses. Such configurations can desirably regulate the air pressure at the heater, such as through the valves. Such configurations can desirably limit the amount of vaporizable material that is drawn from the reservoir so that the amount of drawn vaporizable material is less than or equal to the amount of vaporizable material that the heater can vaporize.

Exemplary Nicotine Liquid Formulations

Included herein are, inter alia, nicotine liquid formulations for use in electronic vaporizers, such as devices provided herein. In embodiments, a nicotine liquid formulation includes nicotine and an acid such as an organic acid. In embodiments, a nicotine liquid formulation includes a liquid carrier.

Nicotine is a chemical stimulant and increases, for example, heart rate and blood pressure when provided to an animal, e.g., a mammal such as a human. The stimulant effect of nicotine may be referred to herein as nicotine stimulant effect. In embodiments, the stimulant effect is correlated to the nicotine serum level. In embodiments, nicotine transfer to a subject is associated with a feeling of physical and/or emotional satisfaction. In embodiments, the devices and formulations provided herein are useful for reducing a user's craving for a traditional cigarette.

Aspects of the present disclosure relate to formulations and devices for eliciting a nicotine-related biological effect (e.g. a nicotine stimulant effect) in a user. In embodiments, the nicotine-related biological effect (e.g. a nicotine stimulant effect) is comparable to that of a traditional cigarette such as a Pall Mall® or Newport 100® cigarette. In embodiments the traditional cigarette is the type of cigarette preferred by the user. A "nicotine-related biological effect" is an effect that is detectable by the user (e.g. subject) and includes, but is not limited to, a stimulating effect (also referred to herein as a nicotine stimulant effect) or a relaxing effect (e.g., reduced anxiety or irritability). In embodiments, the nicotine-related biological effect is a stimulating effect (also referred to herein as a nicotine stimulant effect). In embodiments, a nicotine-related biological effect is improved concentration. In embodiments, a nicotine-related biological effect is increased alertness. A nicotine stimulant effect may manifest as, for example, an increase in heart rate, an increase in blood pressure, and/or a feeling of satisfaction (e.g., physical satisfaction or emotional satisfaction) of a user. In embodiments, an increased nicotine-related biological effect (e.g. a nicotine stimulation effect, such as a faster rise in heart rate) may be achieved, for example, within about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 220 seconds, about 240 seconds, about 260 seconds, about 280 seconds, about 300 seconds, about 320 seconds, about 340 seconds, about 360 seconds, about 7 minutes, about 8 minutes, about 9 minutes or about 10 minutes following delivery of nicotine or protonated nicotine in accordance with the teachings of the present disclosure. In embodiments, the nicotine stimulant effect is an increase in heart rate. The increase in heart rate may be achieved, for example, within about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 220 seconds, about 240 seconds, about 260 seconds, about 280 seconds, about 300 seconds, about 320 seconds, about 340 seconds, about 360 seconds, about 7 minutes, about 8 minutes, about 9 minutes or about 10 minutes following delivery of nicotine or protonated nicotine in accordance with the teachings of the present disclosure. In embodiments, the effective amount of nicotine (e.g., protonated nicotine) raises the heart rate of a user by about 10%, or about 15%, or about 20%, or about 25%, or about 30%, or about 35%, or about 40%, or about 45%, or about 50%, or about 55%, or about 60% relative to the heart rate of the user prior to the delivery of nicotine (e.g., protonated nicotine) in accordance with the teachings of the present disclosure. In embodiments, the effective amount of protonated nicotine raises the heart rate of a user by about 10%, or about 15%, or about 20%, or about 25%, or about 30%, or about 35%, or about 40%, or about 45%, or about 50%, or about 55%, or about 60% relative to the heart rate of a corresponding user who receives an the same amount of nicotine in free base form. In embodiments, the heart rate is resting heart rate. In embodiments, the nicotine-related biological effect is reduced craving for a cigarette. In embodiments, the reduced craving is experienced within about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 220 seconds, about 240 seconds, about 260 seconds, about 280 seconds, about 300 seconds, about 320 seconds, about 340 seconds, about 360 seconds, about 7 minutes, about 8 minutes, about 9 minutes or about 10 minutes following delivery of nicotine or protonated nicotine in accordance with the teachings of the present disclosure. In embodiments, the nicotine-related biological effect is an enjoyable sensation in the throat or chest. In embodiments, the nicotine-related biological effect is any combination of 2, 3, 4, 5, or more effects associated with nicotine disclosed herein or known in the art. Such effects are not limited to what a user can perceive, and thus can include both objective and subjective effects.

In embodiments, use of a nicotine liquid formulation provided herein mimics the peak nicotine delivery of a traditional cigarette. In embodiments, the $C_{max}$ and/or $T_{max}$ value(s) for a user's plasma nicotine levels are comparable to those of a traditional cigarette (or are approaching that of a traditional cigarette, e.g., are 90-100% or at least about 80%, 85%, 90%, or 95% the $C_{max}$ and/or $T_{max}$ value of the traditional cigarette). In embodiments, the rate of nicotine uptake in the plasma of blood of users is about the same as that of a traditional cigarette (e.g., the $C_{max}$ and $T_{max}$ values are at least about 90% of the $C_{max}$ and $T_{max}$ values of a traditional cigarette). In embodiments, the rate of nicotine uptake in the plasma or blood of users is less than that of the traditional cigarette, but sufficient to, e.g., reduce craving for the traditional cigarette. In embodiments, formulations (e.g., nicotine-organic acid formulations) that demonstrate the quickest rate of nicotine uptake in the plasma are more preferred in satisfaction evaluations, and are rated more equivalent to cigarette satisfaction than the formulations showing the slower rates of rise of nicotine in plasma. In embodiments, a user rates his or her satisfaction level as at least a 3 on a scale ranging from 1 to 7, where 1=not at all, 2=very little, 3=a little, 4=moderately, 5=a lot, 6=quite a lot and 7=extremely. In embodiments, the user rates his or her satisfaction level a 4 on the scale. In embodiments, the user rates his or her satisfaction level a 5 on the scale. In embodiments, the user rates his or her satisfaction level as a 6 on the scale. In embodiments, the user rates his or her satisfaction level a 7 on the scale.

In an aspect, a nicotine liquid formulation is provided including nicotine, an acid (such as an organic acid), and a liquid carrier. In embodiments, when heating the formulation, an inhalable aerosol is formed comprising an effective amount of nicotine and/or protonated nicotine. In embodiments, when heating the formulation, an inhalable aerosol is formed comprising an effective amount of protonated nicotine. In embodiments, the formulation is in a cartridge. In embodiments, the cartridge is in an electronic nicotine delivery system. An "effective amount" of a compound (such as nicotine) is an amount sufficient for the compound to accomplish a stated purpose relative to the absence of the compound (e.g. achieve the effect for which it is administered). The term "effective amount" also includes an amount that is more sufficient to accomplish the stated purpose, provided the stated purpose is accomplished without undue adverse side effects (such as toxicity or irritation) commensurate with a reasonable benefit/risk ratio when used in the manner of this disclosure. In embodiments, an effective amount of nicotine (such as protonated nicotine, free base nicotine, or a combination thereof) is an amount of nicotine that is sufficient to result in a nicotine-related biological effect (e.g., a nicotine stimulant effect) in a user.

In an aspect, a method of providing nicotine to a user (also referred to herein as a subject) of an electronic nicotine delivery system is provided. "Providing" nicotine to a user includes making nicotine available (such as via an electronic nicotine delivery system) or administering nicotine (such as via an electronic nicotine delivery system) to a user. In embodiments, the administration is self-administration. In embodiments, "providing" nicotine to a user may include making available to, selling to, and/or delivering to a user who wishes to self-administer nicotine a device that is configured to be operated by the user. In embodiments, nicotine is self-administered by inhaling aerosol comprising the nicotine, wherein the nicotine is produced by the device when the device is operated.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the aerosol includes protonated nicotine in an amount such that the user experiences a nicotine-related biological effect.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the aerosol includes the organic acid in an amount such that the user experiences a nicotine-related biological effect.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the aerosol includes nicotine and an amount of organic acid sufficient to, subsequent to inhalation by a user, cause an increased nicotine-related biological effect in the user relative to the absence of the organic acid.

In embodiments, the method includes (a) (the user) operating an electronic nicotine delivery system as disclosed herein including a nicotine liquid formulation, the formulation including nicotine, an organic acid, and a liquid carrier, wherein the electronic nicotine delivery system heats the formulation to an operating temperature, such that an inhalable aerosol including an effective amount of protonated nicotine is produced; and (b) (the user) inhaling the inhalable aerosol. Operating an electronic nicotine delivery system includes activating the essential electronic components of the electronic nicotine delivery system to allow for the heating and inhalation. In embodiments, operating an electronic nicotine delivery system comprises, consists essentially of, or consists of the user holding the electronic nicotine delivery system and drawing from on a mouthpiece of the electronic nicotine delivery system. In embodiments, the effective amount is an amount such that the user experiences a nicotine-related biological effect upon inhalation.

In embodiments, an effective amount of nicotine is effective to reduce a user's craving for a traditional cigarette. In embodiments, the craving is completely reduced such that the user has no craving for the traditional cigarette. In embodiments, the nicotine-related biological effect is a physiological response that is similar or equivalent to the response from nicotine provided by smoking traditional cigarette. In embodiments, the nicotine-related biological effect is nicotine stimulation that mimics (e.g., is equivalent to) that of a traditional cigarette. In embodiments, the nicotine-related biological effect is increased heart rate that mimics the increased heart rate of a user who is smoking a traditional cigarette. The heart rate of a user who is smoking a traditional cigarette may be referred to herein as the "heart rate of a traditional cigarette." An increased heart rate "mimics" that of a traditional cigarette if the heart rate is about the same as, has about the same magnitude as, or has the about same rate of increase compared to the heart rate of a traditional cigarette.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the organic acid is present in an amount such that the user has reduced or no craving for a traditional cigarette.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the organic acid is present in an amount such that the user has a physiological response that is similar or equivalent to the response from nicotine provided by smoking traditional cigarette.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the organic acid is present in an amount such that the user experiences increased nicotine-related biological effect (e.g. a faster rise in heart rate) that mimics that of a traditional cigarette.

In embodiments, the method includes (a) heating a nicotine liquid formulation in an electronic nicotine delivery system to produce an inhalable aerosol, wherein the formulation includes nicotine and an organic acid in a liquid carrier; and (b) inhalation of the aerosol by the user, wherein the organic acid is present in an amount sufficient to provide nicotine stimulation that mimics that of a traditional cigarette.

In embodiments, the aerosol includes protonated nicotine sufficient to, subsequent to inhalation by a user, cause a rise in the level of plasma nicotine in the user that mimics a traditional cigarette.

In embodiments, the method includes (a) heating a nicotine liquid formulation in an electronic nicotine delivery system to produce an inhalable aerosol, wherein the formulation includes nicotine and benzoic acid in a liquid carrier, wherein the formulation includes an amount of protonated nicotine of about 0.5% to about 5% or about 1.5% to about 2.5%; and (b) inhalation of the aerosol by the user. In embodiments, most or all of the nicotine is protonated in the formulation. In embodiments, at least 85-95%, 85-90%, 85-99%, 90-95%, 90-99%, or 95-99% of the nicotine in the formulation is protonated. In embodiments, at least about 85%, 86%, 87%, 88%, 89%, 90%, 91%, 92%, 93%, 94%, 95%, 96%, 97%, 98%, or 99% of the nicotine is protonated. In embodiments, from about 85%, 86%, 87%, 88%, 89%, or 90% to about 91%, 92%, 93%, 94%, 95%, 96%, 97%, 98%, or 99% of the nicotine is protonated. In embodiments, 100% of the nicotine is protonated. In embodiments, at least 85% of the nicotine is protonated. In embodiments, at least 90% of the nicotine is protonated. In embodiments, at least 91% of the nicotine is protonated. In embodiments, at least 92% of the nicotine is protonated. In embodiments, at least 93% of the nicotine is protonated. In embodiments, at least 94% of the nicotine is protonated. In embodiments, at least 95% of the nicotine is protonated. In embodiments, at least 96% of the nicotine is protonated. In embodiments, at least 97% of the nicotine is protonated. In embodiments, at least 98% of the nicotine is protonated. In embodiments, at least 99% of the nicotine is protonated.

In embodiments, more or all of the nicotine in an aerosol produced (e.g., in a device, or according to a method provided herein) is protonated. In embodiments, at least 85-95%, 85-90%, 85-99%, 90-95%, 90-99%, or 95-99% of the nicotine in the aerosol is protonated. In embodiments, at least about 85%, 86%, 87%, 88%, 89%, 90%, 91%, 92%, 93%, 94%, 95%, 96%, 97%, 98%, or 99% of the nicotine is protonated. In embodiments, from about 85%, 86%, 87%, 88%, 89%, or 90% to about 91%, 92%, 93%, 94%, 95%, 96%, 97%, 98%, or 99% of the nicotine is protonated. In embodiments, 100% of the nicotine is protonated. In embodiments, at least 85% of the nicotine is protonated. In embodiments, at least 90% of the nicotine is protonated. In embodiments, at least 91% of the nicotine is protonated. In embodiments, at least 92% of the nicotine is protonated. In embodiments, at least 93% of the nicotine is protonated. In embodiments, at least 94% of the nicotine is protonated. In embodiments, at least 95% of the nicotine is protonated. In embodiments, at least 96% of the nicotine is protonated. In embodiments, at least 97% of the nicotine is protonated. In embodiments, at least 98% of the nicotine is protonated. In embodiments, at least 99% of the nicotine is protonated.

In embodiments, the method includes (a) heating a nicotine liquid formulation in an electronic nicotine delivery system to produce an inhalable aerosol, wherein the formulation includes nicotine and benzoic acid in a liquid carrier; and (b) inhalation of the aerosol by the user.

In embodiments, the method includes (a) heating a nicotine liquid formulation in an electronic nicotine delivery system to produce an inhalable aerosol, wherein the formulation includes nicotine and lactic acid in a liquid carrier; and (b) inhalation of the aerosol by the user.

In embodiments, the method includes (a) heating a nicotine liquid formulation in an electronic nicotine delivery system to produce an inhalable aerosol, wherein the formulation includes nicotine, benzoic acid, and lactic acid in a liquid carrier; and (b) inhalation of the aerosol by the user.

In an aspect, a method of producing an inhalable aerosol comprising nicotine and benzoic acid is provided. In embodiments, the method includes heating nicotine and benzoic acid in an electronic inhaler to produce the aerosol, wherein the aerosol includes nicotine and an amount of benzoic acid sufficient to, subsequent to inhalation by a user, cause an increased nicotine-related biological effect (e.g. a faster rise in heart rate) in the user relative to the absence of the benzoic acid. In an aspect, a method of producing an inhalable aerosol comprising nicotine and lactic acid is provided. In embodiments, the method includes heating nicotine and lactic acid in an electronic inhaler to produce the aerosol, wherein the aerosol includes nicotine and an amount of lactic acid sufficient to, subsequent to inhalation by a user, cause an increased nicotine-related biological effect (e.g. a faster rise in heart rate) relative to the absence of the lactic acid. In an aspect, a method of producing an inhalable aerosol comprising nicotine, benzoic acid, and lactic acid is provided. In embodiments, the method includes heating nicotine and benzoic acid and lactic acid in an electronic inhaler to produce the aerosol, wherein the aerosol includes nicotine and an amount of benzoic acid and lactic acid sufficient to, subsequent to inhalation by a user, cause an increased nicotine-related biological effect (e.g. a faster rise in heart rate) in the user relative to the absence of the benzoic acid and the lactic acid.

In embodiments, the method includes heating a nicotine liquid formulation in an electronic nicotine delivery system to produce an inhalable aerosol, the formulation comprising nicotine and one or more organic acids in a liquid carrier, wherein the one or more organic acids include a keto acid, an aliphatic monocarboxylic acid, an aliphatic dicarboxylic acid, an aromatic acid, and/or a hydroxyacid.

In embodiments, the method includes heating a nicotine liquid formulation in an electronic nicotine delivery system to produce an inhalable aerosol, the formulation comprising nicotine and a carboxylic acid in a liquid carrier, wherein the carboxylic acid is a beta-keto acid, an aliphatic monocarboxylic acid, an aromatic acid, or a hydroxyacid. In embodiments, the formulation includes an amount of the carboxylic acid sufficient to, subsequent to inhalation, cause an increased nicotine-related biological effect (e.g. a faster rise in heart rate) in the user relative to the absence of the carboxylic acid. In embodiments, the formulation includes an amount of the carboxylic acid sufficient to, subsequent to inhalation, cause a faster rise in heart rate in the user relative to the absence of the carboxylic acid.

In embodiments, the method includes heating a nicotine liquid formulation in an electronic nicotine delivery system to produce an inhalable aerosol, the formulation comprising nicotine and an organic acid in a liquid carrier, wherein (a) the formulation includes an amount of the organic acid sufficient to, subsequent to inhalation, cause an increased nicotine-related biological effect (e.g. a faster rise in heart rate) in the user relative to the absence of the organic acid; and (b) the electronic nicotine delivery system includes a cartridge, wherein the cartridge serves as a reservoir that holds the formulation and as a mouthpiece for the electronic nicotine delivery system.

In embodiments, the method includes heating a nicotine liquid formulation in an electronic nicotine delivery system to produce an inhalable aerosol, the formulation comprising nicotine and an organic acid in a liquid carrier, wherein (a) the pH of the liquid formulation is sufficiently acidic to, subsequent to inhalation, cause an increased nicotine-related biological effect (e.g. a faster rise in heart rate) in the user relative to the absence of the organic acid; and (b) the electronic nicotine delivery system includes a cartridge, wherein the cartridge serves as a reservoir that holds the formulation and as a mouthpiece for the electronic nicotine delivery system. In embodiments, the pH of the formulation is less than 7.0. In embodiments, the pH of the formulation is from about 2.5 to about 6.5. In embodiments, the pH of the formulation is from about 3 to about 6.5. In embodiments, the pH of the formulation is from about 4 to about 6.5. In embodiments, the pH of the formulation is from about 5 to about 6.5. In embodiments, the pH of the formulation is from about 6 to about 6.5. In embodiments, the pH of the formulation is from about 3 to about 5.5. In embodiments, the pH of the formulation is from about 3.5 to about 5.5. In embodiments, the pH of the formulation is about 2.5, 3, 3.5, 4, 4.5, 5, 5.5, 6, or 6.5.

In embodiments, the aerosol includes level of protonated nicotine such that the user has about 80-100% or at least about 80%, 85%, 86%, 87%, 88%, 89%, 90%, 91%, 92%, 93%, 94%, 95%, 96%, 97%, 98%, or 99% the plasma nicotine $C_{max}$ value of a traditional cigarette. In embodiments, the aerosol includes level of protonated nicotine such that the user has about 80-100% or at least about 80%, 85%, 86%, 87%, 88%, 89%, 90%, 91%, 92%, 93%, 94%, 95%, 96%, 97%, 98%, or 99% the plasma nicotine $T_{max}$ value of a traditional cigarette.

In embodiments, the aerosol includes an amount of nicotine in combination with organic acid such that the user has about 80-100% or at least about 80%, 85%, 86%, 87%, 88%, 89%, 90%, 91%, 92%, 93%, 94%, 95%, 96%, 97%, 98%, or 99% the plasma nicotine $C_{max}$ value of a traditional cigarette. In embodiments, the aerosol includes an amount of nicotine in combination with organic acid such that the user has about 80-100% or at least about 80%, 85%, 86%, 87%, 88%, 89%, 90%, 91%, 92%, 93%, 94%, 95%, 96%, 97%, 98%, or 99% the plasma nicotine $T_{max}$ value of a traditional cigarette.

In an aspect, provided herein is a device (e.g., an electronic nicotine delivery system such as an electronic nicotine delivery system disclosed herein) comprising a nicotine liquid formulation disclosed herein.

In an aspect, provided herein is an electronic nicotine delivery system cartridge comprising a nicotine liquid formulation disclosed herein. In embodiments, the cartridge is in a package such as a blister pack. In embodiments, the cartridge is in an electronic nicotine delivery system. In embodiments, the cartridge serves as a mouthpiece and a reservoir for the formulation. In embodiments, the cartridge is a cartomizer.

In embodiments, the aerosol produced from an electronic nicotine delivery system is produced from a single nicotine liquid formulation that is in a single reservoir contained within an electronic nicotine delivery system or a cartridge thereof.

Non-limiting examples of nicotine liquid formulations comprising one or more organic acids are disclosed in U.S. Pat. No. 9,215,895; U.S. Patent Application Publication No. 2016/0302471; and PCT International Application Publication No. WO 2018/031600, the entire contents of each of which are incorporated herein by reference.

Unless specified and depending on context, the term "nicotine" means "free base nicotine and/or protonated nicotine" (regardless of the counterion). In embodiments, the nicotine in a nicotine liquid formulation provided herein is either naturally occurring nicotine (e.g., from extract of nicotineous species such as tobacco), or synthetic nicotine. In embodiments, the nicotine is (−)-nicotine, (+)-nicotine, or a mixture thereof. In embodiments, the nicotine is employed in relatively pure form (e.g., greater than about 80% pure, 85% pure, 90% pure, 95% pure, 99% pure, 99.5% pure, or 99.9% pure by weight before it is combined with one or more other ingredients of a formulation). In embodiments, the nicotine for a formulation provided herein is "water clear" in appearance in order to avoid or minimize the formation of tarry residues during the subsequent formulation steps. In embodiments, 90-100% or at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% of the nicotine in a formulation is (−)-nicotine.

In embodiments, a nicotine liquid formulation includes an organic acid.

The term "organic acid" refers to an organic compound with acidic properties (e.g., by Brønsted-Lowry definition, or Lewis definition). Common organic acids are the carboxylic acids, whose acidity is associated with their carboxyl group (—COOH). A dicarboxylic acid possesses two carboxylic acid groups. The relative acidity of an organic is measured by its $pK_a$ value and one of skill in the art knows how to determine the acidity of an organic acid based on its given pKa value. The term "keto acid" as used herein, refers to organic compounds that contain a carboxylic acid group and a ketone group. Common types of keto acids include alpha-keto acids, or 2-oxoacids, such as pyruvic acid or oxaloacetic acid, having the keto group adjacent to the carboxylic acid; beta-keto acids, or 3-oxoacids, such as acetoacetic acid, having the ketone group at the second carbon from the carboxylic acid; and gamma-keto acids, or 4-oxoacids, such as levulinic acid, having the ketone group at the third carbon from the carboxylic acid. In embodiments, the organic acid is benzoic acid, oxalic acid, salicylic acid, succinic acid, sorbic acid, pyruvic acid, levulinic acid, or lactic acid.

In embodiments, the organic acid is a carboxylic acid. In embodiments, the carboxylic acid is an aliphatic acid. In embodiments, the aliphatic acid is a straight-chain aliphatic acid. In embodiments, the aliphatic acid is a branched-chain aliphatic acid. In embodiments, the aliphatic acid is an aliphatic monocarboxylic acid. In embodiments, the aliphatic acid is an aliphatic dicarboxylic acid. In embodiments, the aliphatic dicarboxylic acid is malonic acid or succinic acid. In embodiments, the carboxylic acid is an aromatic acid. In embodiments, the aromatic acid is benzoic acid or phenylacetic acid.

In embodiments, the carboxylic acid is a hydroxyacid. In embodiments, the hydroxyacid is lactic acid.

In embodiments, the organic acid is a keto acid. In embodiments, the keto acid is an alpha-keto acid. In embodiments, the alpha-keto acid is pyruvic acid or oxaloacetic acid. In embodiments, the keto acid is a beta-keto acid. In embodiments, the beta-keto acid is acetoacetic acid. In embodiments, the keto acid is a gamma-keto acid. In embodiments, the gamma-keto acid is levulinic acid.

In embodiments, the organic acid is any one or more of 2-furoic acid, acetic acid, acetoacetic acid, alpha-methylbutyric acid, ascorbic acid, benzoic acid, beta-methylvaleric acid, butyric acid, caproic acid, citric acid, formic acid, fumaric acid, glycolic acid, heptanoic acid, isobutyric acid, isovaleric acid, lactic acid, levulinic acid, malic acid, malonic acid, myristic acid, nonanoic acid, octanoic acid, oxalic acid, oxaloacetic acid, phenylacetic acid, propionic acid, pyruvic acid, succinic acid, and tartaric acid.

Non-limiting examples of organic acids in dude aromatic acids such as optionally substituted benzoic acids, hydroxy-acids, heterocyclic acids, terpenoid acids, sugar acids such as the pectic acids, amino acids, cycloaliphatic acids, dicarboxylic acids, aliphatic acids, keto acids, and the like. In embodiments, a formulation includes one or more organic acids that are aliphatic acids (e.g., straight-chain and/or branched-chain aliphatic acids). In embodiments, t a formulation includes one or more organic acids that are aliphatic monocarboxylic acids such as acetic acid, propionic acid, isobutyric acid, butyric acid, or the like. In embodiments, a formulation includes one or more organic acids that are keto carboxylic acids. In embodiments, a formulation includes formic, acetic, propionic, isobutyric, butyric, alpha-methylbutyric, isovaleric, beta-methylvaleric, caproic, 2-furoic, phenylacetic, heptanoic, octanoic, nonanoic, malic, citric, oxalic, malonic, glycolic, succinic, ascorbic, tartaric, fumaric, and/or pyruvic acid. In embodiments, a formulation includes one or more $C_4$ to $C_{28}$ fatty acids, and other such acids.

In embodiments, a formulation includes one or more carboxylic acids. Non-limiting examples of carboxylic acids include monocarboxylic acids, dicarboxylic acids (organic acid containing two carboxylic acid groups), and carboxylic acids containing an aromatic group such as benzoic acids, hydroxycarboxylic acids, heterocyclic carboxylic acids, terpenoid acids, and sugar acids; such as the pectic acids, amino acids, cycloaliphatic acids, aliphatic carboxylic acids, keto carboxylic acids, and the like. In embodiments, a formulation includes one or more of formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, gluconic acid, saccharic acid, salicyclic acid, sorbic acid, malonic acid, and malic acid. In embodiments, a formulation includes one or more of benzoic acid, pyruvic acid, salicylic acid, levulinic acid, malic acid, succinic acid, and citric acid. In embodiments, a formulation includes one or more of benzoic acid, pyruvic acid, and salicylic acid. In embodiments, a formulation includes benzoic acid. In embodiments, a formulation includes lactic acid. In embodiments, a formulation includes benzoic acid and lactic acid. In embodiments, a formulation includes at least one of benzoic acid, oxalic acid, salicylic acid, succinic acid, sorbic acid, pyruvic acid, levulinic acid, or lactic acid.

In embodiments, an organic acid used in a nicotine liquid formulation does not decompose at the operating temperature of the electronic nicotine delivery system.

In embodiments, the formulation does not include citric acid. In embodiments, the formulation does not include pyruvic acid. In embodiments, the formulation does not include malic acid. In embodiments, the formulation includes no more than 10, 9, 8, 7, 6, 5, 4, 3, 2, or 1 acid(s). In embodiments, the formulation includes no more than 10, 9, 8, 7, 6, 5, 4, 3, 2, or 1 organic acid(s). In embodiments, the formulation includes no more than 10 organic acids. In embodiments, the formulation includes no more than 9 organic acids. In embodiments, the formulation includes no more than 8 organic acids. In embodiments, the formulation includes no more than 7 organic acids. In embodiments, the formulation includes no more than 6 organic acids. In embodiments, the formulation includes no more than 5 organic acids. In embodiments, the formulation includes no more than 4 organic acids. In embodiments, the formulation includes no more than 3 organic acids. In embodiments, the formulation includes no more than 2 organic acids. In embodiments, the formulation includes only 1 organic acid. In embodiments, the formulation includes no more than 10 carboxylic acids. In embodiments, the formulation includes no more than 9 carboxylic acids. In embodiments, the formulation includes no more than 8 carboxylic acids. In embodiments, the formulation includes no more than 7 carboxylic acids. In embodiments, the formulation includes no more than 6 carboxylic acids. In embodiments, the formulation includes no more than 5 carboxylic acids. In embodiments, the formulation includes no more than 4 carboxylic acids. In embodiments, the formulation includes no more than 3 carboxylic acids. In embodiments, the formulation includes no more than 2 carboxylic acids. In embodiments, the formulation includes only 1 carboxylic acid.

In embodiments, a formulation includes an organic compound that exhibits an acid character and is capable of forming a counter ion with nicotine when in its conjugate base form. Exemplary compounds include the phenolics such as guaiacol, vanillin, protocatechualdehyde, and the like.

In embodiments, the concentration of nicotine in the nicotine liquid formulation is from about 0.5% to about 25%, wherein the concentration is of nicotine weight to total solution weight, i.e. (w/w). In embodiments, a nicotine liquid formulation has a nicotine concentration of about 1% (w/w) to about 20% (w/w). In embodiments, a nicotine liquid formulation has a nicotine concentration of about 1% (w/w) to about 18% (w/w). In embodiments, a nicotine liquid formulation has a nicotine concentration of about 1% (w/w) to about 15% (w/w). In embodiments, a nicotine liquid formulation has a nicotine concentration of about 4% (w/w) to about 12% (w/w). In embodiments, a nicotine liquid formulation has a nicotine concentration of about 1% (w/w) to about 18% (w/w), about 3% (w/w) to about 15% (w/w), or about 4% (w/w) to about 12% (w/w). In embodiments, a nicotine liquid formulation has a nicotine concentration of about 0.5% (w/w) to about 10% (w/w). In embodiments, a nicotine liquid formulation has a nicotine concentration of about 0.5% (w/w) to about 5% (w/w). In embodiments, a nicotine liquid formulation has a nicotine concentration of about 0.5% (w/w) to about 4% (w/w). In embodiments, a nicotine liquid formulation has a nicotine concentration of about 0.5% (w/w) to about 3% (w/w). In embodiments, a nicotine liquid formulation has a nicotine concentration of about 0.5% (w/w) to about 2% (w/w). In embodiments, a nicotine liquid formulation has a nicotine concentration of about 0.5% (w/w) to about 1% (w/w). In embodiments, a nicotine liquid formulation has a nicotine concentration of about 1% (w/w) to about 10% (w/w). In embodiments, a nicotine liquid formulation has a nicotine concentration of about 1% (w/w) to about 5% (w/w). In embodiments, a nicotine liquid formulation has a nicotine concentration of about 1% (w/w) to about 4% (w/w). In embodiments, a nicotine liquid formulation has a nicotine concentration of about 1% (w/w) to about 3% (w/w). In embodiments, a nicotine liquid formulation has a nicotine concentration of about 1% (w/w) to about 2% (w/w). In embodiments, a nicotine liquid formulation has a nicotine concentration of about 2% (w/w) to about 10% (w/w). In embodiments, a nicotine liquid formulation has a nicotine concentration of about 2% (w/w) to about 5% (w/w). In embodiments, a nicotine liquid formulation has a nicotine concentration of about 2% (w/w) to about 4% (w/w). In embodiments, a nicotine liquid formulation has a nicotine concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, or 20% (w/w), or more, including any increments therein. In embodiments, a nicotine liquid formulation has a nicotine liquid formulation having a nicotine concentration of about 5% (w/w). In embodiments, a nicotine liquid formulation has a nicotine concentration of about 4% (w/w). In embodiments, a nicotine liquid formulation has a nicotine concentration of about 3% (w/w). In embodiments, a nicotine liquid formulation has a nicotine concentration of about 2% (w/w). In embodiments, a nicotine liquid formulation has a nicotine concentration of about 1% (w/w). In embodiments, a nicotine liquid formulation has a nicotine concentration of about 0.5% (w/w).

In embodiments, a nicotine liquid formulation has a nicotine concentration of about 0.5% (w/w), 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), or about 20% (w/w). In embodiments, a nicotine liquid formulation has a nicotine concentration from about 0.5% (w/w) to about 20% (w/w), from about 0.5% (w/w) to about 18% (w/w), from about 0.5% (w/w) to about 15% (w/w), from about 0.5% (w/w) to about 12% (w/w), from about 0.5% (w/w) to about 10% (w/w), from about 0.5% (w/w) to about 8% (w/w), from about 0.5% (w/w) to about 7% (w/w), from about 0.5% (w/w) to about 6% (w/w), from about 0.5% (w/w) to about 5% (w/w), from about 0.5% (w/w) to about 4% (w/w), from about 0.5% (w/w) to about 3% (w/w), or from about 0.5% (w/w) to about 2% (w/w). In embodiments, a nicotine liquid formulation has a nicotine concentration from about 1% (w/w) to about 20% (w/w), from about 1% (w/w) to about 18% (w/w), from about 1% (w/w) to about 15% (w/w), from about 1% (w/w) to about 12% (w/w), from about 1% (w/w) to about 10% (w/w), from about 1% (w/w) to about 8% (w/w), from about 1% (w/w) to about 7% (w/w), from about 1% (w/w) to about 6% (w/w), from about 1% (w/w) to about 5% (w/w), from about 1% (w/w) to about 4% (w/w), from about 1% (w/w) to about 3% (w/w), or from about 1% (w/w) to about 2% (w/w). In embodiments, a nicotine liquid formulation has a nicotine concentration from about 2% (w/w) to about 20% (w/w), from about 2% (w/w) to about 18% (w/w), from about 2% (w/w) to about 15% (w/w), from about 2% (w/w) to about 12% (w/w), from about 2% (w/w) to about 10% (w/w), from about 2% (w/w) to about 8% (w/w), from about 2% (w/w) to about 7% (w/w), from about 2% (w/w) to about 6% (w/w), from about 2% (w/w) to about 5% (w/w), from about 2% (w/w) to about 4% (w/w), or from about 2% (w/w) to about 3% (w/w). In embodiments, a nicotine liquid formulation has a nicotine concentration from about 3% (w/w) to about 20% (w/w), from about 3% (w/w) to about 18% (w/w), from about 3% (w/w) to about 15% (w/w), from about 3% (w/w) to about 12% (w/w), from about 3% (w/w) to about 10% (w/w), from about 3% (w/w) to about 8% (w/w), from about 3% (w/w) to about 7% (w/w), from about 3% (w/w) to about 6% (w/w), from about 3% (w/w) to about 5% (w/w), or from about 3% (w/w) to about 4% (w/w). In embodiments, a nicotine liquid formulation has a nicotine concentration from about 4% (w/w) to about 20% (w/w), from about 4% (w/w) to about 18% (w/w), from about 4% (w/w) to about 15% (w/w), from about 4% (w/w) to about 12% (w/w), from about 4% (w/w) to about 10% (w/w), from about 4% (w/w) to about 8% (w/w), from about 4% (w/w) to about 7% (w/w), from about 4% (w/w) to about 6% (w/w), or from about 4% (w/w) to about 5% (w/w). In embodiments, a nicotine liquid formulation has a nicotine concentration from about 5% (w/w) to about 20% (w/w), from about 5% (w/w) to about 18% (w/w), from about 5% (w/w) to about 15% (w/w), from about 5% (w/w) to about 12% (w/w), from about 5% (w/w) to about 10% (w/w), from about 5% (w/w) to about 8% (w/w), from about 5% (w/w) to about 7% (w/w), or from about 5% (w/w) to about 6% (w/w). In embodiments, a nicotine liquid formulation has a nicotine concentration from about 6% (w/w) to about 20% (w/w), from about 6% (w/w) to about 18% (w/w), from about 6% (w/w) to about 15% (w/w), from about 6% (w/w) to about 12% (w/w), from about 6% (w/w) to about 10% (w/w), from about 6% (w/w) to about 8% (w/w), or from about 6% (w/w) to about 7% (w/w). In embodiments, a nicotine liquid formulation has a nicotine concentration from about 2% (w/w) to about 6% (w/w). In embodiments, a nicotine liquid formulation has a nicotine concentration of about 5% (w/w).

In embodiments, the concentration of nicotine in the nicotine liquid formulation is from about 1%, 1.1%, 1.2%, 1.3%, 1.4%, 1.5%, 1.6%, or 1.7% to about 2.5%, 2.4%, 2.3%, 2.2%, 2.1%, 2.0%, 1.9%, or 1.8% (w/w). In embodiments, the concentration of nicotine in the nicotine liquid formulation is about 1%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5% (w/w).

In embodiments, the concentration of protonated nicotine in the nicotine liquid formulation is from about 0.5% (w/w) to about 25% (w/w). In embodiments, the concentration of protonated nicotine in the nicotine liquid formulation is from about 1% (w/w) to about 20% (w/w). In embodiments, the concentration of protonated nicotine in the nicotine liquid formulation is from about 1% (w/w) to about 18% (w/w). In embodiments, the concentration of protonated nicotine in the nicotine liquid formulation is from about 1% (w/w) to about 15% (w/w). In embodiments, the concentration of protonated nicotine in the nicotine liquid formulation is from about 4% (w/w) to about 12% (w/w). In embodiments, the concentration of protonated nicotine in the nicotine liquid formulation is from about 2% (w/w) to about 6% (w/w). In embodiments, the concentration of protonated nicotine in the nicotine liquid formulation is about 5% (w/w). In embodiments, the concentration of protonated nicotine in the nicotine liquid formulation is about 4% (w/w). In embodiments, the concentration of protonated nicotine in the nicotine liquid formulation is about 3% (w/w). In embodiments, the concentration of protonated nicotine in the nicotine liquid formulation is about 2% (w/w). In embodiments, the concentration of protonated nicotine in the nicotine liquid formulation is about 1% (w/w).

In embodiments, the concentration of protonated nicotine in the nicotine liquid formulation is from about 1%, 1.1%, 1.2%, 1.3%, 1.4%, 1.5%, 1.6%, or 1.7% to about 2.5%, 2.4%, 2.3%, 2.2%, 2.1%, 2.0%, 1.9%, or 1.8% (w/w). In embodiments, the concentration of protonated nicotine in the the nicotine liquid formulation is about 1%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5% (w/w).

In embodiments, the concentration of organic acid in the nicotine liquid formulation is from about 0.5% to about 25%, wherein the concentration is of organic acid weight to total solution weight, i.e. (w/w). In embodiments, a nicotine liquid formulation has a organic acid concentration of about 1% (w/w) to about 20% (w/w). In embodiments, a nicotine liquid formulation has a organic acid concentration of about 1% (w/w) to about 18% (w/w). In embodiments, a nicotine liquid formulation has a organic acid concentration of about 1% (w/w) to about 15% (w/w). In embodiments, a nicotine liquid formulation has a organic acid concentration of about 4% (w/w) to about 12% (w/w). In embodiments, a nicotine liquid formulation has a organic acid concentration of about 1% (w/w) to about 18% (w/w), about 3% (w/w) to about 15% (w/w), or about 4% (w/w) to about 12% (w/w). In embodiments, a nicotine liquid formulation has a organic acid concentration of about 0.5% (w/w) to about 10% (w/w). In embodiments, a nicotine liquid formulation has a organic acid concentration of about 0.5% (w/w) to about 5% (w/w). In embodiments, a nicotine liquid formulation has a organic acid concentration of about 0.5% (w/w) to about 4% (w/w). In embodiments, a nicotine liquid formulation has a organic acid concentration of about 0.5% (w/w) to about 3% (w/w). In embodiments, a nicotine liquid formulation has a organic acid concentration of about 0.5% (w/w) to about 2% (w/w). In embodiments, a nicotine liquid formulation has a organic acid concentration of about 0.5% (w/w) to about 1% (w/w). In embodiments, a nicotine liquid formulation has a organic acid concentration of about 1% (w/w) to about 10% (w/w). In embodiments, a nicotine liquid formulation has a organic acid concentration of about 1% (w/w) to about 5% (w/w). In embodiments, a nicotine liquid formulation has a organic acid concentration of about 1% (w/w) to about 4% (w/w). In embodiments, a nicotine liquid formulation has a organic acid concentration of about 1% (w/w) to about 3% (w/w). In embodiments, a nicotine liquid formulation has a organic acid concentration of about 1% (w/w) to about 2% (w/w). In embodiments, a nicotine liquid formulation has a organic acid concentration of about 2% (w/w) to about 10% (w/w). In embodiments, a nicotine liquid formulation has a organic acid concentration of about 2% (w/w) to about 5% (w/w). I In embodiments, a nicotine liquid formulation has a organic acid concentration of about 2% (w/w) to about 4% (w/w). In embodiments, a nicotine liquid formulation has a organic acid concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, or 20% (w/w), or more, including any increments therein. In embodiments, a nicotine liquid formulation has a nicotine liquid formulation having a organic acid concentration of about 5% (w/w). In embodiments, a nicotine liquid formulation has a organic acid concentration of about 4% (w/w). In embodiments, a nicotine liquid formulation has a organic acid concentration of about 3% (w/w). In embodiments, a nicotine liquid formulation has a organic acid concentration of about 2% (w/w). In embodiments, a nicotine liquid formulation has a organic acid concentration of about 1% (w/w). In embodiments, a nicotine liquid formulation has a organic acid concentration of about 0.5% (w/w).

In embodiments, a nicotine liquid formulation has a organic acid concentration of about 0.5% (w/w), 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), or about 20% (w/w). In embodiments, a nicotine liquid formulation has a organic acid concentration from about 0.5% (w/w) to about 20% (w/w), from about 0.5% (w/w) to about 18% (w/w), from about 0.5% (w/w) to about 15% (w/w), from about 0.5% (w/w) to about 12% (w/w), from about 0.5% (w/w) to about 10% (w/w), from about 0.5% (w/w) to about 8% (w/w), from about 0.5% (w/w) to about 7% (w/w), from about 0.5% (w/w) to about 6% (w/w), from about 0.5% (w/w) to about 5% (w/w), from about 0.5% (w/w) to about 4% (w/w), from about 0.5% (w/w) to about 3% (w/w), or from about 0.5% (w/w) to about 2% (w/w). In embodiments, a nicotine liquid formulation has a organic acid concentration from about 1% (w/w) to about 20% (w/w), from about 1% (w/w) to about 18% (w/w), from about 1% (w/w) to about 15% (w/w), from about 1% (w/w) to about 12% (w/w), from about 1% (w/w) to about 10% (w/w), from about 1% (w/w) to about 8% (w/w), from about 1% (w/w) to about 7% (w/w), from about 1% (w/w) to about 6% (w/w), from about 1% (w/w) to about 5% (w/w), from about 1% (w/w) to about 4% (w/w), from about 1% (w/w) to about 3% (w/w), or from about 1% (w/w) to about 2% (w/w). In embodiments, a nicotine liquid formulation has a organic acid concentration from about 2% (w/w) to about 20% (w/w), from about 2% (w/w) to about 18% (w/w), from about 2% (w/w) to about 15% (w/w), from about 2% (w/w) to about 12% (w/w), from about 2% (w/w) to about 10% (w/w), from about 2% (w/w) to about 8% (w/w), from about 2% (w/w) to about 7% (w/w), from about 2% (w/w) to about 6% (w/w), from about 2% (w/w) to about 5% (w/w), from about 2% (w/w) to about 4% (w/w), or from about 2% (w/w) to about 3% (w/w). In embodiments, a nicotine liquid formulation has a organic acid concentration from about 3% (w/w) to about 20% (w/w), from about 3% (w/w) to about 18% (w/w), from about 3% (w/w) to about 15% (w/w), from about 3% (w/w) to about 12% (w/w), from about 3% (w/w) to about 10% (w/w), from about 3% (w/w) to about 8% (w/w), from about 3% (w/w) to about 7% (w/w), from about 3% (w/w) to about 6% (w/w), from about 3% (w/w) to about 5% (w/w), or from about 3% (w/w) to about 4% (w/w). In embodiments, a nicotine liquid formulation has a organic acid concentration from about 4% (w/w) to about 20% (w/w), from about 4% (w/w) to about 18% (w/w), from about 4% (w/w) to about 15% (w/w), from about 4% (w/w) to about 12% (w/w), from about 4% (w/w) to about 10% (w/w), from about 4% (w/w) to about 8% (w/w), from about 4% (w/w) to about 7% (w/w), from about 4% (w/w) to about 6% (w/w), or from about 4% (w/w) to about 5% (w/w). In embodiments, a nicotine liquid formulation has a organic acid concentration from about 5% (w/w) to about 20% (w/w), from about 5% (w/w) to about 18% (w/w), from about 5% (w/w) to about 15% (w/w), from about 5% (w/w) to about 12% (w/w), from about 5% (w/w) to about 10% (w/w), from about 5% (w/w) to about 8% (w/w), from about 5% (w/w) to about 7% (w/w), or from about 5% (w/w) to about 6% (w/w). In embodiments, a nicotine liquid formulation has a organic acid concentration from about 6% (w/w) to about 20% (w/w), from about 6% (w/w) to about 18% (w/w), from about 6% (w/w) to about 15% (w/w), from about 6% (w/w) to about 12% (w/w), from about 6% (w/w) to about 10% (w/w), from about 6% (w/w) to about 8% (w/w), or from about 6% (w/w) to about 7% (w/w). In embodiments, a nicotine liquid formulation has a organic acid concentration from about 2% (w/w) to about 6% (w/w). In embodiments, a nicotine liquid formulation has a organic acid concentration of about 5% (w/w).

In embodiments, the concentration of organic acid in the nicotine liquid formulation is from about 1%, 1.1%, 1.2%, 1.3%, 1.4%, 1.5%, 1.6%, or 1.7% to about 2.5%, 2.4%, 2.3%, 2.2%, 2.1%, 2.0%, 1.9%, or 1.8% (w/w). In embodiments, the concentration of organic acid in the nicotine liquid formulation is about 1%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5% (w/w).

Unless specified otherwise with respect to concentrations of nicotine (e.g., total nicotine, free base nicotine, and/or protonated nicotine) in a nicotine liquid formulation, the term "about" in the context of a numerical value or range means ±10% of the numerical value or range recited or claimed, unless the context requires a more limited range. In each instance in which a numerical value or range is preceded by the term "about" in this description, the specific numerical value or range without the term "about" is also disclosed. For example, a disclosure of "about 1%" is also a disclosure of "1%." Where a numerical range is provided, all integers within that range, and tenths thereof, are also disclosed. For example, "0.5% to 5%" is a disclosure of 0.5%, 0.6%, 0.7%, 0.8%, 0.9%, 1%, 1.1%, etc. up to and including 5%.

In embodiments, the pH of the nicotine liquid formulation is less than 7.0. In embodiments, the pH of the formulation is from about 2.5 to about 6.5. In embodiments, the pH of the formulation is from about 3 to about 6.5. In embodiments, the pH of the formulation is from about 4 to about 6.5. In embodiments, the pH of the formulation is from about 5 to about 6.5. In embodiments, the pH of the formulation is from about 6 to about 6.5. In embodiments, the pH of the formulation is from about 3 to about 5.5. In embodiments, the pH of the formulation is from about 3.5 to about 5.5. In embodiments, the pH of the formulation is about 2.5, 3, 3.5, 4, 4.5, 5, 5.5, 6, or 6.5.

In embodiments, a formulation may include various stoichiometric ratios and/or molar ratios of acid to nicotine, acidic functional groups to nicotine, and acidic functional group hydrogens to nicotine. In embodiments, the molar ratio of the nicotine to acid (nicotine:acid) is 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In embodiments, the molar ratio of the acid to nicotine (acid:nicotine) is 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In embodiments, the ratio is the ratio of nicotine to one acid in a formulation. In embodiments, the ratio is the ratio of nicotine to all acids in a formulation. In embodiments, the ratio is the ratio of nicotine to all organic acids in a formulation. In embodiments, the molar ratio of the nicotine to acid in the formulation is 1:1, 1:2, 1:3, or 1:4. In embodiments, the molar ratio of acid to nicotine in the formulation is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional groups to nicotine in the formulation is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional group hydrogens to nicotine in the formulation is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acid to nicotine in the aerosol is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional groups to nicotine in the aerosol is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional group hydrogens to nicotine in the aerosol is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1.

In embodiments, the nicotine is protonated. In embodiments, the number or moles of organic acid functional groups is equal to or greater than the molar amount of nicotine. In embodiments, the number or moles of organic acid functional groups is equal to the molar amount of nicotine.

In embodiments, the number or moles of organic acid functional groups is greater than the molar amount of nicotine.

In embodiments, the number or moles of organic acid functional groups is from about 1.1 times greater to about 3.0 times greater than the molar amount of nicotine. In embodiments, the number of organic acid functional groups is from about 1.5 times greater to about 2.2 times greater than the molar amount of nicotine.

In embodiments, the amount of or moles of excess organic acid functional groups is about 1.1 times greater, or about 1.2 times greater, or about 1.3 times greater, or about 1.4 times greater, or about 1.5 times greater, or about 1.6 times greater, or about 1.7 times greater, or about 1.8 times greater, or about 2 times greater, or about 2.1 times greater, or about 2.2 times greater, or about 2.3 times greater, or about 2.4 times greater, or about 2.5 times greater, or about 2.6 times greater, or about 2.7 times greater, or about 2.8 times greater, or about 2.9 times greater, or about 3.0 times greater, etc., than the molar amount of nicotine present in the formulation. In embodiments, the excess amount or moles of organic acid functional groups, provide less harshness upon inhalation to a user relative to a control formulation.

In embodiments, the molar ratio of organic acid to nicotine is about 0.5:1. In embodiments, the molar ratio of organic acid to nicotine is about 0.6:1. In embodiments, the molar ratio of organic acid to nicotine is about 0.7:1. In embodiments, the molar ratio of organic acid to nicotine is about 0.8:1. In embodiments, the molar ratio of organic acid to nicotine is about 0.9:1. In embodiments, the molar ratio of organic acid to nicotine is about 1.0:1. In embodiments, the molar ratio of organic acid to nicotine is about 1.1:1. In embodiments, the molar ratio of organic acid to nicotine is about 1.2:1. In embodiments, the molar ratio of organic acid to nicotine is about 1.3:1. In embodiments, the molar ratio of organic acid to nicotine is about 1.4:1. In embodiments, the molar ratio of organic acid to nicotine is about 1.5:1. In embodiments, the molar ratio of organic acid to nicotine is about 1.6:1. In embodiments, the molar ratio of organic acid to nicotine is about 1.7:1. In embodiments, the molar ratio of organic acid to nicotine is about 1.8:1. In embodiments, the molar ratio of organic acid to nicotine is about 1.9:1. In embodiments, the molar ratio of organic acid to nicotine is about 2.0:1. In embodiments, the molar ratio of organic acid to nicotine is about 3:1. In embodiments, the molar ratio of organic acid to nicotine is about 4:1. In embodiments, the molar ratio of organic acid to nicotine is about 5:1. In embodiments, the molar ratio of organic acid to nicotine is about 6:1. In embodiments, the molar ratio of organic acid to nicotine is about 7:1. In embodiments, the molar ratio of organic acid to nicotine is about 8:1. In embodiments, the molar ratio of organic acid to nicotine is about 9:1. In embodiments, the molar ratio of organic acid to nicotine is about 10:1. In embodiments, the molar ratio of organic acid to nicotine is about 11:1. In embodiments, the molar ratio of organic acid to nicotine is about 12:1. In embodiments, the molar ratio of organic acid to nicotine is about 13:1. In embodiments, the molar ratio of organic acid to nicotine is about 14:1. In embodiments, the molar ratio of organic acid to nicotine is about 15:1. In embodiments, the molar ratio of organic acid to nicotine is about 16:1. In embodiments, the molar ratio of organic acid to nicotine is about 17:1. In embodiments, the molar ratio of organic acid to nicotine is about 18:1. In embodiments, the molar ratio of organic acid to nicotine is about 19:1. In embodiments, the molar ratio of organic acid to nicotine is about 20:1.

In embodiments, the molar ratio of organic acid to nicotine is at least 0.5:1. In embodiments, the molar ratio of organic acid to nicotine is at least 0.6:1. In embodiments, the molar ratio of organic acid to nicotine is at least 0.7:1. In embodiments, the molar ratio of organic acid to nicotine is at least 0.8:1. In embodiments, the molar ratio of organic acid to nicotine is at least 0.9:1. In embodiments, the molar ratio of organic acid to nicotine is at least 1.0:1. In embodiments, the molar ratio of organic acid to nicotine is at least 1.1:1. In embodiments, the molar ratio of organic acid to nicotine is at least 1.2:1. In embodiments, the molar ratio of organic acid to nicotine is at least 1.3:1. In embodiments, the molar ratio of organic acid to nicotine is at least 1.4:1. In embodiments, the molar ratio of organic acid to nicotine is at least 1.5:1. In embodiments, the molar ratio of organic acid to nicotine is at least 1.6:1. In embodiments, the molar ratio of organic acid to nicotine is at least 1.7:1. In embodiments, the molar ratio of organic acid to nicotine is at least 1.8:1. In embodiments, the molar ratio of organic acid to nicotine is at least 1.9:1. In embodiments, the molar ratio of organic acid to nicotine is at least 2.0:1. In embodiments, the molar ratio of organic acid to nicotine is at least 3:1. In embodiments, the molar ratio of organic acid to nicotine is at least 4:1. In embodiments, the molar ratio of organic acid to nicotine is at least 5:1. In embodiments, the molar ratio of organic acid to nicotine is at least 6:1. In embodiments, the molar ratio of organic acid to nicotine is at least 7:1. In embodiments, the molar ratio of organic acid to nicotine is at least 8:1. In embodiments, the molar ratio of organic acid to nicotine is at least 9:1. In embodiments, the molar ratio of organic acid to nicotine is at least 10:1. In embodiments, the molar ratio of organic acid to nicotine is at least 11:1. In embodiments, the molar ratio of organic acid to nicotine is at least 12:1. In embodiments, the molar ratio of organic acid to nicotine is at least 13:1. In embodiments, the molar ratio of organic acid to nicotine is at least 14:1. In embodiments, the molar ratio of organic acid to nicotine is at least 15:1. In embodiments, the molar ratio of organic acid to nicotine is at least 16:1. In embodiments, the molar ratio of organic acid to nicotine is at least 17:1. In embodiments, the molar ratio of organic acid to nicotine is at least 18:1. In embodiments, the molar ratio of organic acid to nicotine is at least 19:1. In embodiments, the molar ratio of organic acid to nicotine is at least 20:1.

Nicotine is an alkaloid molecule that has two basic nitrogens. It may occur in different states of protonation. Nicotine is "protonated" if at least one of the two nitrogens is covalently bound to a proton. Protonated nicotine includes monoprotonated nicotine, diprotonated nicotine, and combinations thereof. If one nitrogen is protonated, then the nicotine is "monoprotonated" nicotine. If two nitrogens are protonated, then the nicotine is "diprotonated" nicotine. If no protonation exists, nicotine is referred to as the "free base" nicotine. In embodiments, when nicotine is combined with a sufficient amount of acid, the nicotine becomes protonated. Once protonated, the nicotine positively charged and the formulation may further include a counter ion. In embodiments, the counter ion is the conjugate base of the acid. For example, where the acid is benzoic acid, the counter ion may be benzoate, thereby forming nicotine benzoate.

In embodiments, different nicotine liquid formulations produce varying degrees of increase in a nicotine-related biological effect (e.g. a faster rise in heart rate). In embodiments, different nicotine liquid formulations produce varying degrees of satisfaction, stimulation, nicotine delivery, and/or heart rate increase in an individual. In embodiments, the extent of protonation of the nicotine effects satisfaction, stimulation, nicotine delivery, and/or heart rate such that more protonation is more satisfying as compared to less protonation. In embodiments, nicotine, for example in the formulation, and/or aerosol is monoprotonated. In embodiments, nicotine, for example in the formulation, and/or aerosol is diprotonated. In embodiments, nicotine, for example in the formulation, and/or aerosol is exists in more than one protonation state, e.g., an equilibrium of monoprotonated and diprotonated nicotine. In embodiments, the extent of protonation of nicotine is dependent upon the ratio of nicotine:acid used in the formulation. In embodiments, the extent of protonation of nicotine is dependent upon the solvent. In embodiments, the extent of protonation of nicotine has not been determined.

In embodiments, a liquid carrier includes a liquid solvent or medium in which a protonated nicotine is soluble (e.g. at ambient conditions, such as 25 degrees Celsius) such that the protonated nicotine does not form a solid precipitate. Examples include, but are not limited to, glycerol, propylene glycol, trimethylene glycol, water, ethanol and the like, as well as combinations thereof. In embodiments, the liquid carrier includes a ratio of propylene glycol and vegetable glycerin. In embodiments, the liquid carrier includes 10% to 70% of propylene glycol and 90% to 30% of vegetable glycerin. In embodiments, the liquid carrier includes 20% to 50% of propylene glycol and 80% to 50% of vegetable glycerin. In embodiments, the liquid carrier includes 30% propylene glycol and 70% vegetable glycerin. In embodiments, the liquid carrier is completely propylene glycol or vegetable glycerin. In embodiments, the liquid carrier includes another aerosol forming agent similar to propylene glycol, glycerin, or other glycols or the like, or any combination thereof.

In embodiments, heating an amount of a nicotine liquid formulation produces a aerosol, wherein at least about 50% of acid in the amount is in the aerosol. In embodiments, at least about 90% of the nicotine in the amount is in the aerosol. In embodiments, at least about 50%, at least about 60%, at least about 70%, at least about 80%, at least about 90%, at least about 95%, or at least about 99% of the acid in the amount is in the aerosol. In embodiments, at least about 50% to about 99% of the acid in the amount is in the aerosol. In embodiments, at least about 50% to about 95% of the acid in the amount is in the aerosol. In embodiments, at least about 50% to about 90% of the acid in the amount is in the aerosol. In embodiments, at least about 50% to about 80% of the acid in the amount is in the aerosol. In embodiments, at least about 50% to about 70% of the acid in the amount is in the aerosol. In embodiments, at least about 50% to about 60% of the acid in the amount is in the aerosol. In embodiments, at least about 60% to about 99% of the acid in the amount is in the aerosol. In embodiments, at least about 60% to about 95% of the acid in the amount is in the aerosol. In embodiments, at least about 60% to about 90% of the acid in the amount is in the aerosol. In embodiments, at least about 60% to about 80% of the acid in the amount is in the aerosol. In embodiments, at least about 60% to about 70% of the acid in the amount is in the aerosol. In embodiments, at least about 70% to about 99% of the acid in the amount is in the aerosol. In embodiments, at least about 70% to about 95% of the acid in the amount is in the aerosol. In embodiments, at least about 70% to about 90% of the acid in the amount is in the aerosol. In embodiments, at least about 70% to about 80% of the acid in the amount is in the aerosol. In embodiments, at least about 50%, at least about 60%, at least about 70%, at least about 80%, at least about 90%, at least 95%, or at least about 99% of the nicotine in the amount is in the aerosol. In embodiments, at least about 50% to about 99% of the nicotine in the amount is in the aerosol. In embodiments, at least about 50% to about 95% of the nicotine in the amount is in the aerosol. In embodiments, at least about 50% to about 90% of the nicotine in the amount is in the aerosol. In embodiments, at least about 50% to about 80% of the nicotine in the amount is in the aerosol. In embodiments, at least about 50% to about 70% of the nicotine in the amount is in the aerosol. In embodiments, at least about 50% to about 60% of the nicotine in the amount is in the aerosol. In embodiments, at least about 60% to about 99% of the nicotine in the amount is in the aerosol. In embodiments, at least about 60% to about 95% of the nicotine in the amount is in the aerosol. In embodiments, at least about 60% to about 90% of the nicotine in the amount is in the aerosol. In embodiments, at least about 60% to about 80% of the nicotine in the amount is in the aerosol. In embodiments, at least about 60% to about 70% of the nicotine in the amount is in the aerosol. In embodiments, at least about 70% to about 99% of the nicotine in the amount is in the aerosol. In embodiments, at least about 70% to about 95% of the nicotine in the amount is in the aerosol. In embodiments, at least about 70% to about 90% of the nicotine in the amount is in the aerosol. In embodiments, at least about 70% to about 80% of the nicotine in the amount is in the aerosol.

In embodiments, the aerosol is delivered in particles small enough to be delivered through the oral or nasal cavity and to a user's lungs, for example the alveoli of a user's lungs. In embodiments, the aerosol particles are sized (e.g., have a diameter of) from about 0.1 microns to about 5 microns, from about 0.1 microns to about 4.5 microns, from about 0.1 microns to about 4 microns, from about 0.1 microns to about 3.5 microns, from about 0.1 microns to about 3 microns, from about 0.1 microns to about 2.5 microns, from about 0.1 microns to about 2 microns, from about 0.1 microns to about 1.5 microns, from about 0.1 microns to about 1 microns, from about 0.1 microns to about 0.9 microns, from about 0.1 microns to about 0.8 microns, from about 0.1 microns to about 0.7 microns, from about 0.1 microns to about 0.6 microns, from about 0.1 microns to about 0.5 microns, from about 0.1 microns to about 0.4 microns, from about 0.1 microns to about 0.3 microns, from about 0.1 microns to about 0.2 microns, from about 0.2 microns to about 5 microns, from about 0.2 microns to about 4.5 microns, from about 0.2 microns to about 4 microns, from about 0.2 microns to about 3.5 microns, from about 0.2 microns to about 3 microns, from about 0.2 microns to about 2.5 microns, from about 0.2 microns to about 2 microns, from about 0.2 microns to about 1.5 microns, from about 0.2 microns to about 1 microns, from about 0.2 microns to about 0.9 microns, from about 0.2 microns to about 0.8 microns, from about 0.2 microns to about 0.7 microns, from about 0.2 microns to about 0.6 microns, from about 0.2 microns to about 0.5 microns, from about 0.2 microns to about 0.4 microns, from about 0.2 microns to about 0.3 microns, from about 0.3 microns to about 5 microns, from about 0.3 microns to about 4.5 microns, from about 0.3 microns to about 4 microns, from about 0.3 microns to about 3.5 microns, from about 0.3 microns to about 3 microns, from about 0.3 microns to about 2.5 microns, from about 0.3 microns to about 2 microns, from about 0.3 microns to about 1.5 microns, from about 0.3 microns to about 1 microns, from about 0.3 microns to about 0.9 microns, from about 0.3 microns to about 0.8 microns, from about 0.3 microns to about 0.7 microns, from about 0.3 microns to about 0.6 microns, from about 0.3 microns to about 0.5 microns, from about 0.3 microns to about 0.4, from about 0.4 microns to about 5 microns, from about 0.4 microns to about 4.5 microns, from about 0.4 microns to about 4 microns, from about 0.4 microns to about 3.5 microns, from about 0.4 microns to about 3 microns, from about 0.4 microns to about 2.5 microns, from about 0.4 microns to about 2 microns, from about 0.4 microns to about 1.5 microns, from about 0.4 microns to about 1 microns, from about 0.4 microns to about 0.9 microns, from about 0.4 microns to about 0.8 microns, from about 0.4 microns to about 0.7 microns, from about 0.4 microns to about 0.6 microns, from about 0.4 microns to about 0.5 microns, from about 0.5 microns to about 5 microns, from about 0.5 microns to about 4.5 microns, from about 0.5 microns to about 4 microns, from about 0.5 microns to about 3.5 microns, from about 0.5 microns to about 3 microns, from about 0.5 microns to about 2.5 microns, from about 0.5 microns to about 2 microns, from about 0.5 microns to about 1.5 microns, from about 0.5 microns to about 1 microns, from about 0.5 microns to about 0.9 microns, from about 0.5 microns to about 0.8 microns, from about 0.5 microns to about 0.7 microns, from about 0.5 microns to about 0.6 microns, from about 0.6 microns to about 5 microns, from about 0.6 microns to about 4.5 microns, from about 0.6 microns to about 4 microns, from about 0.6 microns to about 3.5 microns, from about 0.6 microns to about 3 microns, from about 0.6 microns to about 2.5 microns, from about 0.6 microns to about 2 microns, from about 0.6 microns to about 1.5 microns, from about 0.6 microns to about 1 microns, from about 0.6 microns to about 0.9 microns, from about 0.6 microns to about 0.8 microns, from about 0.6 microns to about 0.7 microns, from about 0.8 microns to about 5 microns, from about 0.8 microns to about 4.5 microns, from about 0.8 microns to about 4 microns, from about 0.8 microns to about 3.5 microns, from about 0.8 microns to about 3 microns, from about 0.8 microns to about 2.5 microns, from about 0.8 microns to about 2 microns, from about 0.8 microns to about 1.5 microns, from about 0.8 microns to about 1 microns, from about 0.8 microns to about 0.9 microns, from about 0.9 microns to about 5 microns, from about 0.9 microns to about 4.5 microns, from about 0.9 microns to about 4 microns, from about 0.9 microns to about 3.5 microns, from about 0.9 microns to about 3 microns, from about 0.9 microns to about 2.5 microns, from about 0.9 microns to about 2 microns, from about 0.9 microns to about 1.5 microns, from about 0.9 microns to about 1 microns, from about 1 microns to about 5 microns, from about 1 microns to about 4.5 microns, from about 1 microns to about 4 microns, from about 1 microns to about 3.5 microns, from about 1 microns to about 3 microns, from about 1 microns to about 2.5 microns, from about 1 microns to about 2 microns, from about 1 microns to about 1.5 microns.

In embodiments, an amount of nicotine liquid formulation provided to the heater includes a volume or a mass. In embodiments, the amount is quantified "per puff." In embodiments, the amount includes a volume of about 1 µL, about 2 µL, about 3 µL, about 4 µL, about 5 µL, about 6 µL, about 7 µL, about 8 µL, about 9 µL, about 10 µL, about 15 µL, about 20 µL, about 25 µL, about 30 µL, about 35 µL, about 40 µL, about 45 µL, about 50 µL, about 60 µL, about 70 µL, about 80 µL, about 90 µL, about 100 µL, or greater than about 100 µL. In embodiments, the amount includes a mass of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, or greater than about 100 mg.

In embodiments, nicotine in aerosol from a device provided herein is delivered (e.g., absorbed) faster than nicotine in the smoke from a traditional cigarette, such that less nicotine is needed in the aerosol. In embodiments, one puff of the aerosol has less nicotine than one puff from a traditional cigarette. In embodiments, the one puff of the aerosol is the first, second, third, fourth, fifth, sixth, seventh, eighth, ninth, or tenth puff from a cartridge-containing device disclosed herein when the device is fully charged and a new cartridge is used. In embodiments, the one puff from the traditional cigarette is the first, second, third, fourth, fifth, sixth, seventh, eighth, ninth, or tenth puff from the traditional cigarette after the cigarette is first lit. In embodiments, a "puff" is about a 40 ml, 45 ml, 50 ml, 55 ml, 60 ml, 65 ml, 70 ml, 75 ml, or 80 ml volume of aerosol (in the case of a device disclosed herein) or smoke (in the case of a traditional cigarette). In embodiments, the puff is drawn from the device or traditional cigarette over a 1-5 second period of time. In embodiments, the puff is drawn from the device or traditional cigarette over a 2-3 second period of time. In embodiments, the puff is drawn from the device or traditional cigarette over a 2-3 second period of time. In embodiments, the puff is drawn from the device or traditional cigarette over a period of about 1, 2, 3, 4, or 5 seconds. In embodiments, the puff is drawn from the device or traditional cigarette over a period of about 1 seconds. In embodiments, the puff is drawn from the device or traditional cigarette over a period of about 2 seconds. In embodiments, the puff is drawn from the device or traditional cigarette over a period of about 3 seconds. In embodiments, the puff is drawn from the device or traditional cigarette over a period of about 4 seconds. In embodiments, the puff is drawn from the device or traditional cigarette over a period of about 5 seconds. In embodiments, less nicotine is in a puff from a device disclosed herein compared to a traditional cigarette, wherein the puff from the device has a volume of about 70 ml and is drawn from the device over about a 3 second period of time, and wherein the puff from the traditional cigarette has a volume of about 55 ml and is drawn from the traditional cigarette over about a 2 second period of time. In embodiments, a 40-80 ml puff (e.g., 40 ml, 45 ml, 50 ml, 55 ml, 60 ml, 65 ml, 70 ml, 75 ml, or 80 ml) drawn from a device disclosed herein over a period of about 1-5 seconds (e.g., about 1, 1.5, 2, 2.5, 3, 3.5, 4, 4.5, 5, 2-5, 2-4, 2-3, or 1-3 seconds) has about 0.5-1 mg of nicotine. In embodiments, the puff has about 0.5, 0.55, 0.6, 0.65, 0.75, 0.80, 0.85, 0.95, or 1 mg of nicotine. In embodiments, the puff has 0.5-0.75 mg of nicotine. In embodiments, the puff has about 0.75-1 mg nicotine. In embodiments, the puff has 0.65-0.85 mg nicotine.

In embodiments, more of the nicotine in aerosol from a device provided herein is delivered (e.g., absorbed) by a user compared to nicotine in the smoke from a traditional cigarette, such that less nicotine is exhaled by the user. As used herein, the "exhaled nicotine amount" is the amount of nicotine that exit's a user's airways when the user first exhales after inhaling a puff. In embodiments, a user's exhaled nicotine amount is less when using a device disclosed herein compared to when using a traditional cigarette. In embodiments, the exhaled nicotine amount when using a device as disclosed herein is at least about 5%, 10%, 15%, 20%, 25%, 30%, 35%, 40%, 45%, 50%, 55%, 60%, 65%, 70%, 75%, 80%, or 95% less than when using a traditional cigarette. In embodiments, when a user inhales aerosol produced by a device provided herein, at least about 75, 80, 85, 90, 95, 96, 97, 98, or 99% of the nicotine remains within the user (i.e., is not exhaled). In embodiments, when a user inhales aerosol produced by a device provided herein, about 80-100%, 80-90%, 85-95%, 90-100%, 95-100%, 90-95%, 90-99%, 95-99% of the nicotine is not exhaled. In embodiments, when a user inhales aerosol produced by a device provided herein, none of the nicotine is exhaled. In embodiments, a device provided herein is more effective at controlling the dose of nicotine per puff than a traditional cigarette.

In embodiments, a nicotine liquid formulation may comprise one or more flavorants.

In embodiments, the flavor of the constituent acid used in the formulation is a consideration in choosing the acid. In embodiments, a suitable acid has minimal or no toxicity to humans in the concentrations used. In embodiments, a suitable acid is compatible with the electronic nicotine delivery system components it contacts or could contact at the concentrations used. That is, such acid does not degrade or otherwise react with the electronic nicotine delivery system components it contacts or could contact. In embodiments, the odor of the constituent acid used to protonate nicotine is a consideration in choosing a suitable acid. In embodiments, the concentration of protonated nicotine in the carrier may affect the satisfaction of the user. In embodiments, the flavor of the formulation is adjusted by changing the acid. In embodiments, the flavor of the formulation is adjusted by adding exogenous flavorants. In embodiments, an unpleasant tasting or smelling acid is used in minimal quantities to mitigate such characteristics. In embodiments, exogenous pleasant smelling or tasting acid is added to the formulation. Non-limiting examples of organic acids that can provide flavor and aroma to the aerosol at certain levels include acetic acid, oxalic acid, malic acid, isovaleric acid, lactic acid, citric acid, phenylacetic acid, and myristic acid.

In embodiments, the amount of nicotine aerosol (e.g. comprising protonated nicotine) inhaled may be user-determined. In embodiments, the user may, for example, modify the amount of nicotine by adjusting his or her inhalation strength.

In embodiments, the electronic nicotine delivery system does not deliver an increased level of oxygen to the user, e.g., compared to ambient oxygen levels. In embodiments, the electronic nicotine delivery system does not comprise pressurized oxygen gas, or a chemical store of oxygen for inclusion in the aerosol. In embodiments, the aerosol comprises, consists essentially of, or consists of aerosolized nicotine liquid formulation, optionally in combination with ambient air.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge for a vaporizer device, the cartridge comprising:
    a reservoir chamber defined by a reservoir barrier, the reservoir chamber being configured to contain a liquid vaporizable material;
    a vaporization chamber in fluid communication with the reservoir chamber and including a wicking element configured to draw the liquid vaporizable material from the reservoir chamber to the vaporization chamber to be vaporized by a heating element;
    an airflow passageway that extends through the vaporization chamber and between an airflow restrictor and an outlet; and
    an airflow control feature positioned between the airflow restrictor and the outlet, the airflow control feature controlling a reservoir pressure in the reservoir chamber.

2. The cartridge of claim 1, wherein the airflow control feature comprises a fluid passageway extending between the reservoir chamber and the airflow passageway.

3. The cartridge of claim 2, wherein a diameter of the fluid passageway is sized to allow a surface tension of the liquid vaporizable material to prevent passage of the liquid vaporizable material through the fluid passageway when the reservoir pressure is approximately the same as a second pressure along the airflow passageway.

4. The cartridge of claim 3, wherein the diameter is sized to allow the surface tension of the liquid vaporizable material to be disrupted when the reservoir pressure is less than the second pressure along the airflow passageway thereby allowing a volume of air to pass through the airflow control feature and into the reservoir chamber.

5. The cartridge of claim 1, wherein the airflow control feature comprises a check valve or a duck bill valve.

6. The cartridge of claim 2, wherein the airflow control feature comprises a coating including a venting material extending over an opening of the fluid passageway.

7. The cartridge of claim 6, wherein the coating includes a polytetrafluoroethylene (PTFE) material.

8. The cartridge of claim 1, wherein the airflow control feature includes one or more of a septum, a valve, and a pump.

9. The cartridge of claim 1, wherein the airflow control feature includes a vent passageway extending along at least one side of a wick housing containing the vaporization chamber, wherein the vent passageway extends between the reservoir chamber and the vaporization chamber.

10. The cartridge of claim 1, wherein the airflow control feature includes a vent passageway extending through a wick housing containing the vaporization chamber, wherein the vent passageway extends between the reservoir chamber and the vaporization chamber.

11. The cartridge of claim 1, further comprising a pressure sensor configured to sense a pressure along the airflow passageway.

12. The cartridge of claim 1, further comprising a secondary passageway configured to draw air through a part of the cartridge, the secondary passageway configured to merge with the airflow passageway downstream from the vaporization chamber.

13. The cartridge of claim 1, further comprising a pressure-sensing passageway that extends between an outlet of the cartridge and a pressure sensor, the pressure-sensing passageway being separate from the airflow passageway.

14. The cartridge of claim 1, further comprising an inlet positioned along a first side of the cartridge and the outlet being positioned along a second side of the cartridge, the airflow passageway extending between the inlet and the outlet, the inlet and the outlet being positioned along the first side and second side, respectively, such that the inlet and the outlet are open when the cartridge is inserted in a vaporizer device body in a first position and are closed when the cartridge is inserted in the vaporizer device body in a second position.

15. The cartridge of claim 1, wherein the wicking element includes a flat configuration including at least one pair of opposing sides that extend parallel to each other.

16. The cartridge of claim 1, wherein the airflow restrictor restricts a passage of airflow to cause a decrease in pressure downstream from the airflow restrictor compared to upstream from the airflow restrictor, the decrease in pressure assisting with drawing the vaporizable material from the reservoir to the vaporization chamber.

17. The cartridge of claim 1, wherein the airflow restrictor is positioned upstream from the vaporization chamber and upstream from the airflow control feature.

* * * * *